(12) United States Patent
Nam et al.

(10) Patent No.: US 11,524,937 B2
(45) Date of Patent: Dec. 13, 2022

(54) INDIRUBIN DERIVATIVES, AND USES THEREOF

(71) Applicants: CITY OF HOPE, Duarte, CA (US); THE NATIONAL AND KAPODISTRIAN UNIVERSITY OF ATHENS, Athens (GR)

(72) Inventors: Sangkil Nam, Duarte, CA (US); Richard Jove, Duarte, CA (US); Leandros Skaltsounis, Athens (GR)

(73) Assignees: City of Hope, Duarte, CA (US); The National and Kapodistrian University of Athens, Athens (GR)

( * ) Notice: Subject to any disclaimer, the term of this patent is extended or adjusted under 35 U.S.C. 154(b) by 99 days.

(21) Appl. No.: 16/594,894

(22) Filed: Oct. 7, 2019

(65) Prior Publication Data

US 2020/0247750 A1    Aug. 6, 2020

Related U.S. Application Data

(63) Continuation of application No. 13/826,204, filed on Mar. 14, 2013, now Pat. No. 10,435,367, which is a continuation of application No. 13/758,921, filed on Feb. 4, 2013, now Pat. No. 9,512,076.

(60) Provisional application No. 61/676,267, filed on Jul. 26, 2012, provisional application No. 61/594,934, filed on Feb. 3, 2012.

(51) Int. Cl.
*C07D 209/40* (2006.01)
*C07D 401/14* (2006.01)

(52) U.S. Cl.
CPC ........ *C07D 209/40* (2013.01); *C07D 401/14* (2013.01)

(58) Field of Classification Search
CPC .......................... A61K 31/454; A61K 31/445
See application file for complete search history.

(56) References Cited

FOREIGN PATENT DOCUMENTS

WO          93/15722         8/1993
WO        2007/099402        9/2007

OTHER PUBLICATIONS

Aichberger, K. J., et al., "Identification of mcl-1 as a BCR/ABL-Dependent Target in Chronic Myeloid Leukemia (CML): Evidence for Cooperative Antileukemic Effects of Imatinib and mcl-1 Antisense Oligonucleotides," Blood 105:3303-3311 (2005).
Benekli, M., et al., "Signal Transducer and Activator of Transcription Proteins in Leukemias," Blood 101:2940-2954 (2003).
Bromann, P. A., et al., "The Interplay Between Src Family Kinases and Receptor Tyrosine Kinases," Oncogene 23:7957-7968 (2004).
Bromberg, J. F., et al., "Stat3 as an Oncogene," Cell 98:295-303 (1999).

(Continued)

*Primary Examiner* — Savitha M Rao
*Assistant Examiner* — Andrew P Lee
(74) *Attorney, Agent, or Firm* — Perkins Coie LLP; Yingli Wang

(57) ABSTRACT

Indirubin is the major active anti-tumor component of a traditional Chinese herbal medicine used for treatment of chronic myelogenous leukemia (CML). Indirubin derivatives (IRDs) potently reduce the viabilities of various cancer cells and affect kinase activities. IRDs disclosed herein provide new therapeutics for cancer and conditions regulated by the kinase activities.

14 Claims, 65 Drawing Sheets

(56) References Cited

OTHER PUBLICATIONS

Buettner, R., et al., "Activated STAT Signaling in Human Tumors Provides Novel Molecular Targets for Therapeutic Intervention," Clin. Cancer Res. 8:945-954 (2002).
Carlesson., et al., "Tyrosyl Phosphorylation and DNA Binding Activity of Signal Transducers and Activators of Transcription (STAT) Proteins in Hematopoietic Cell Lines Transformed by Bcr/Abl," J. Exp. Med. 183:811-820 (1996).
Donato, N. J., et al., "BCR-ABL Independence and LYN Kinase Overexpression in Chronic Myelogenoud Leukemia Cells Selected for Resistance to STI571," Blood 101:690-698 (2003).
Eisenbrand, G., et al., "Molecular Mechanisms of Indirubin and Its Derivatives: Novel Anticancer Moleculres with Their Origin in Traditional Chinese Phytomedicine," J. Cancer Res. Clin. Oncol. 130:627-635 (2004).
Gesbert, F., et al., "Bcr/Abl Activates Transcription of the Bcl-X Gene Through STAT5," Blood 96:2269-2276 (2000).
Haura, E. B., et al., "Mechanisms of Disease: Insights into the Emerging Role of Signal Transducers and Activators of Transcription in Cancer," Nat. Clin. Pract. Oncol. 2(6):315-324 (2005).
Herrington, J., et al., "The Role of STAT Proteins in Growth Hormone Signaling," Oncogene 19:2585-2597 (2000).
Hoessel, R., et al., "Indirubin, the Active Constituent of a Chinese Antileukaemia Medicine, Inhibits Cyclin-Dependent Kinases," Nat. Cell Biol. 1:60-67 (1999).
Holtz, M. S., et al., "Imatinib Mesylate (STI571) Inhibits Growth of Primitive Malignant Progenitors in Chronic Myelogenous Leukemia Through Reversal of Abnormally Increased Proliferation," Blood 99:3792-3800 (2002).
Horita, M., et al., "Blockade of the Bcr-Abl Kinase Activity Induces Apoptosis of Chronic Myelogenous Leukemia Cells by Suppressing Signal Transducer and Activator of Transcription 5-Dependent Expression of Bcl-xL," J. Exp. Med. 191(6):977-984 (2000).
Huang, M., et al., "Inhibition of Bcr-Abl Kinase Activity by PD180970 Blocks Constitutive Activation of Stat5 and Growth of CML Cells," Oncogene 21:8804-8816 (2002).
Klejman, A., et al., "The Src Family Kinase Hck Couples BCR/ABL to STAT5 Activation in Myeloid Leukemia Cells," EMBO J. 21(21):5766-5774 (2002).
Konig, H., et al., "Effects of Dasatinib on Src Kinase Activity and Downstream Intracellular Signaling in Primitive Chronic Myelogenous Leukemia Hematopoietic Cells," Cancer Res. 68:9624-9633 (2008).
Lionberger, J. M., et al., "Transformation of Myeloid Leukemia Cells to Cytokine Independence by Bcr-Abl is Suppressed by Kinase-Defective Hck," J. Biol. Chem. 275(24):18581-18585 (2000).
Marko, D., et al., "Inhibition of Cyclin-Dependent Kinase 1 (CDK1) by Indirubin Derivatives in Human Tumour Cells," British J. Cancer 84(2):283-289 (2001).
Nam, S., et al., "Indirubin Derivatives Inhibit Stat3 Signaling and Induce Apoptosis in Human Cancer Cells," PNAS 102(17):5998-6003 (2005).
Nam, S., et al., "Action of the Src Family Kinase Inhibitor, Dasatinib (BMS-354825), on Human Prostate Cancer Cells," Cancer Res. 65:9185-9189 (2005).
Nam, S., et al., "Dasatinib (BMS-354825) Inhibits Stat5 Signaling Associated with Apoptosis in Chronic Myelogenous Leukemia Cells," Mol. Cancer Ther. 6:1400-1405 (2007).
Nelson, E. A., et al., "Identification of Human STAT5-Dependent Gene Regulatory Elements Based on Interspecies Homology," J. Biol. Chem. 281(36):26216-26224 (2006).
Nieborowska-Skorska, M., et al., "Signal Transducer and Activator of Transcription (STAT)5 Activation by BCR/ABL is Dependent on Intact Src Homology (SH)3 and SH2 Domains of BCR/ABL and Is Required for Leukemogenesis," J. Exp. Med. 189(8):1229-1242 (1999).
Parsons, S. J., et al., "Src Family Kinases, Key Regulators of Signal Transduction," Oncogene 23:7906-7909 (2004).
Patani, G. A., et al., "Bioisosterism: A Rational Approach in Drug Design," Chem. Rev. 96:3147-3176 (1996).
Ptasznik, A., et al., "Short Interfering RNA (siRNA) Targeting the Lyn Kinase Induces Apoptosis in Primary, and Drug-Resistant, BCR-ABL1 (+) Leukemia Cells," Nat. Med. 10(11):1187-1189 (2004).
Quintas-Cardama, A., et al., "Dasatinib (BMS-354825) is Active in Philidelphia Chromosome-Positive Chronic Myelogenous Leukemia After Imatinib and Nilotinib (AMN107) Therapy Failure," Blood 109:497-499 (2007).
Shah, N. P., et al., "Overriding Imatinib Resistance with a Novel ABL Kinase Inhibitor," Science 305:399-401 (2004).
Silva, C. M., et al., "Role of STATs as Downstream Signal Transducers in Src Family Kinase-Mediated Tumorigenesis," Oncogene 23:8017-8023 (2004).
Simone, J. V., Oncology: Introduction. Cecil Textbook of Medicine. 20th Edition. 1996. vol. 1. pp. 1004-1010.
Vougogiannopoulou, K., et al., "Soluble 3', 6-Substituted Indirubins with Enhanced Selectivity Towards Glycogen Synthase Kinase -3 Alter Circadian Period," J. Med. Chem. 51(20):6421-6431 (2008).
Wilson, M. B., et al., "Selective Pyrrolo-Pyrimidine Inhibitors Reveal a Necessary Role for Src Family Kinases in Bcr-Abl Signal Transduction and Oncogenesis," Oncogene 21:8075-8088 (2002).
Wu, J., et al., "Lyn Regulates BCR-ABL and Gab2 Tyrosine Phosphorylation and c-Cbl Protein Stability in Imatinib-Resistant Chronic Myelogenous Leukemia Cells," Blood 111:3821-3829 (2008).
Xiao, Z., et al., "Indirubin and Meisoindigo in the Treatment of Chronic Myelogenous Leukemia in China," Leuk. Lymphoma 43(9):1763-1768 (2002).
Yu, H., et al., "The STATs of Cancer—New Molecular Targets Come of Age," Nat. Rev. Cancer 4:97-105 (2004).
Yu, H., et al., "STATs in Cancer Inflammation and Immunity: A Leading Role for STAT3," Nat. Rev. Cancer 9:798-809 (2009).
Yuan, H., et al., "BCR-ABL Gene Expression Is Required for Its Mutations in a Novel KCL-22 Cell Culture Model for Acquired Resistance of Chronic Myelogenous Leukemia," J. Biol. Chem. 285(7):5085-5096 (2010).
Zhou, J., et al., "Enhanced Activation of STAT Pathways and Overexpression of Survivin Confer Resistance of FLT3 Inhibitors and Could be Therapeutic Targets in AML," Blood 113:4052-4062 (2009).

Fig. 1A
| IRD No. | ID #. | Structure | MW | [C] DMSO | DS Quantity |
|---|---|---|---|---|---|
| 3 | 673 | 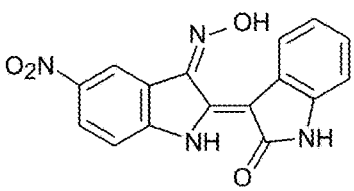 | 322.28 | 10mM | 200µl |
| 4 | 675 | 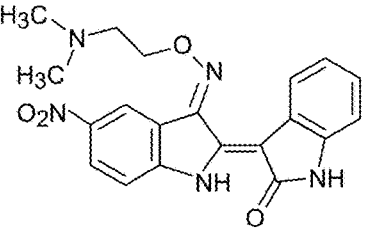 | 393.40 | 10mM | 200µl |
| 5 | 676 | 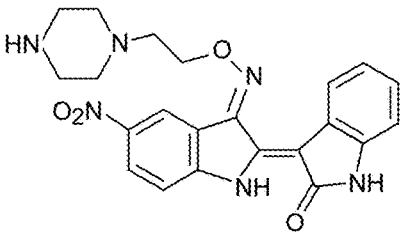 | 434.45 | 10mM | 200µl |
| 6 | 677 | 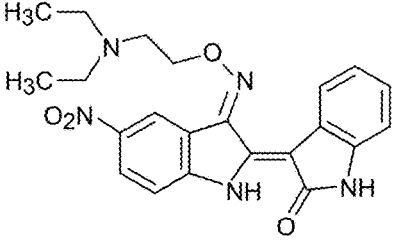 | 421.45 | 5mM | 400µl |
| 7 | 678 | 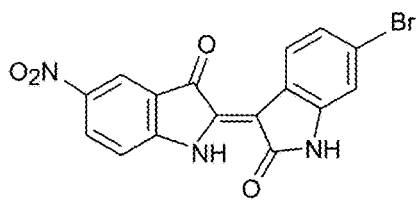 | 386.16 | 10mM | 200µl |

Fig. 1B
| IRD No. | ID #. | Structure | MW | [C] DMSO | DS Quantity |
|---|---|---|---|---|---|
| 8 | 679 | 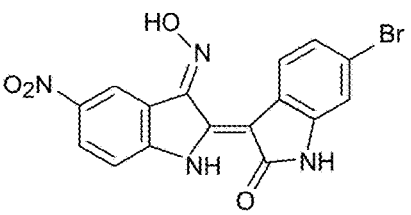 | 401.17 | 10mM | 200µl |
| 9 | 680 | 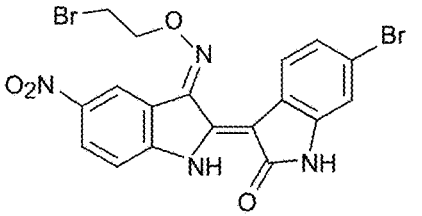 | 508.12 | 5mM | 400µl |
| 10 | 681 | 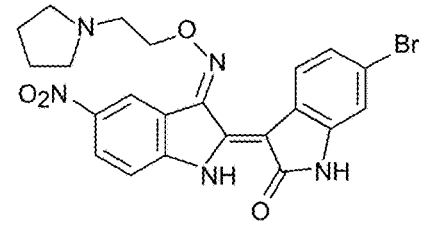 | 498.33 | 5mM | 400µl |
| 11 | 682 | 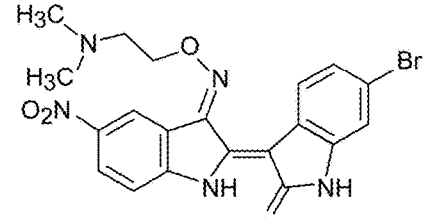 | 472.29 | 5mM | 400µl |
| 12 | 683 | 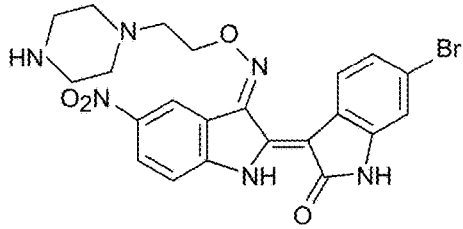 | 513.34 | 10mM | 200µl |

Fig. 1C
| IRD No. | ID #. | Structure | MW | [C] DMSO | DS Quantity |
|---|---|---|---|---|---|
| 13 | 684 | 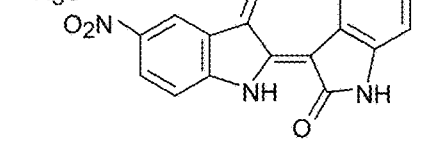 | 500.35 | 5mM | 400µl |
| 14 | 685 | 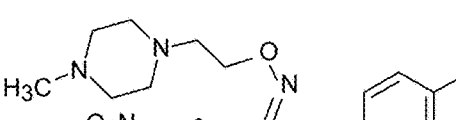 | 527.37 | 5mM | 200µl |
| 15 | 686 | 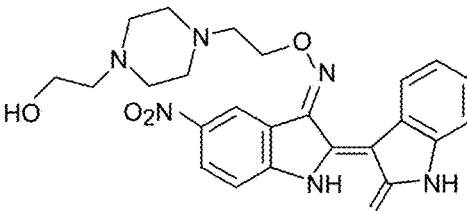 | 557.40 | 10mM | 200µl |
| 16 | 687 | 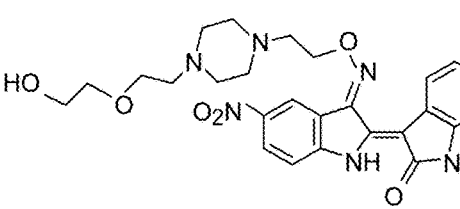 | 601.45 | 10mM | 200µl |
| 17 | 688 | 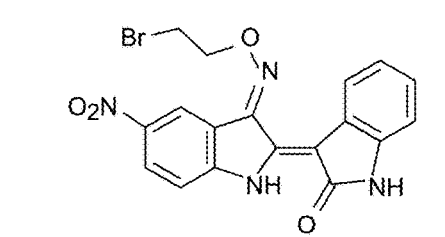 | 429.22 | 5mM | 200µl |

Fig. 1D
| IRD No. | ID #. | Structure | MW | [C] DMSO | DS Quantity |
|---|---|---|---|---|---|
| 18 | 689 | 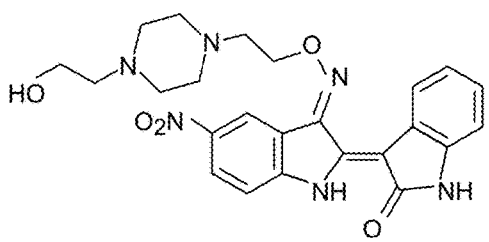 | 478.50 | 10mM | 200μl |
| 19 | 690 | 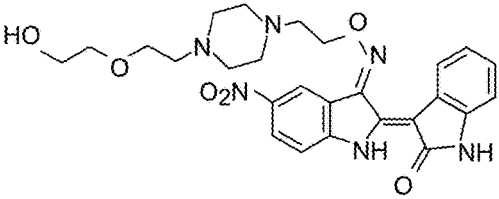 | 522.55 | 10mM | 200μl |
| 20 | 691 | 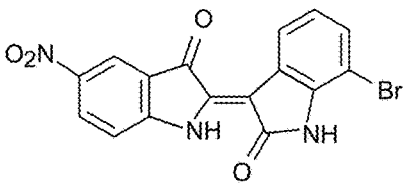 | 386.16 | 5mM | 400μl |
| 21 | 692 | 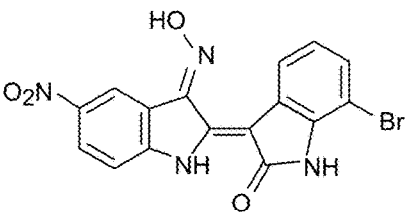 | 401.17 | 10mM | 200μl |
| 22 | 693 | 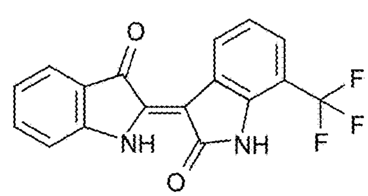 | 330.26 | 10mM | 200μl |

Fig. 1E

| IRD No. | ID #. | Structure | MW | [C] DMSO | DS Quantity |
|---|---|---|---|---|---|
| 23 | 694 | 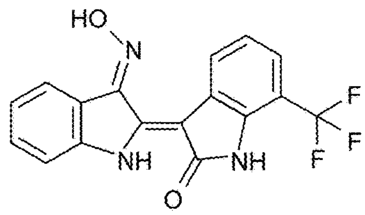 | 345.28 | 10mM | 200µl |
| 24 | 695 | 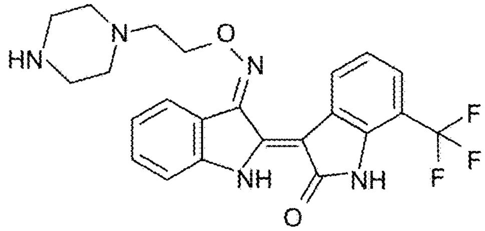 | 457.45 | 10mM | 200µl |
| 25 | 696 | 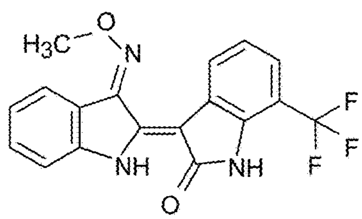 | 359.30 | 10mM | 100µl |
| 26 | 697 | 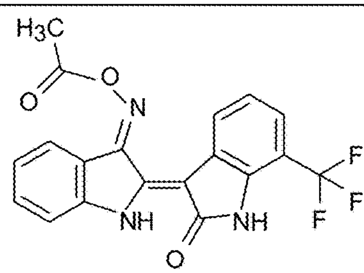 | 387.31 | 10mM | 200µl |
| 27 | 698 | 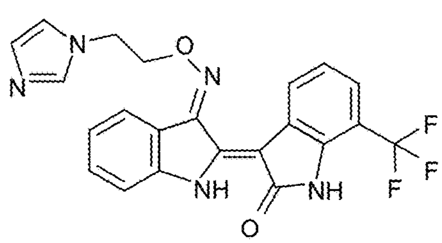 | 439.39 | 10mM | 200µl |

Fig. 1F

| IRD No. | ID #. | Structure | MW | [C] DMSO | DS Quantity |
|---|---|---|---|---|---|
| 28 | 699 | 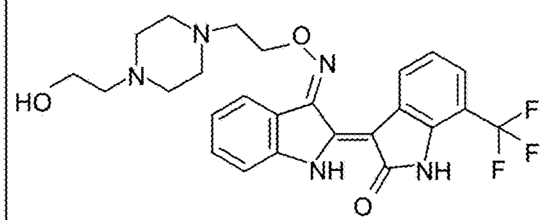 | 501.50 | 10mM | 200µl |
| 29 | 700 | 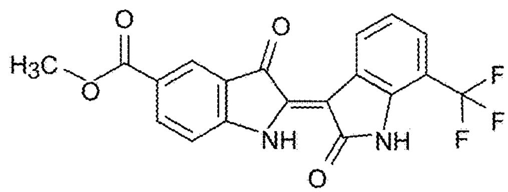 | 388.30 | 10mM | 200µl |
| 30 | 701 | 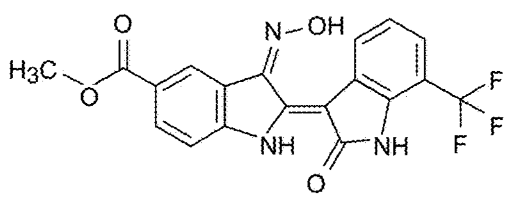 | 403.31 | 10mM | 200µl |
| 31 | 702 | 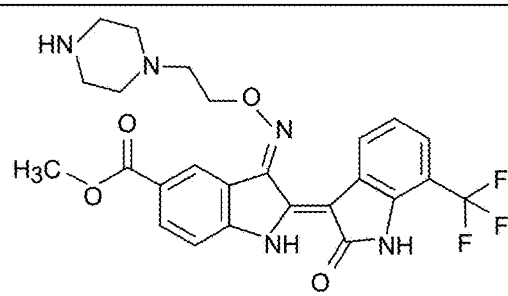 | 515.48 | 10mM | 200µl |
| 32 | 703 | 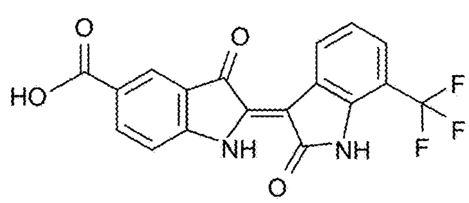 | 374.27 | 10mM | 200µl |

Fig. 1G

| IRD No. | ID #. | Structure | MW | [C] DMSO | DS Quantity |
|---|---|---|---|---|---|
| 34 | 705 | 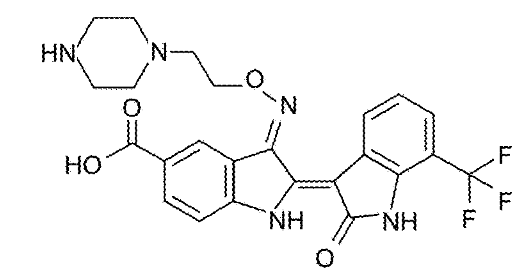 | 501.46 | 10mM | 200µl |
| 35 | 706 | 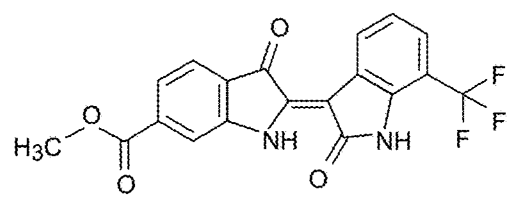 | 388.30 | 10mM | 200µl |
| 36 | 707 | 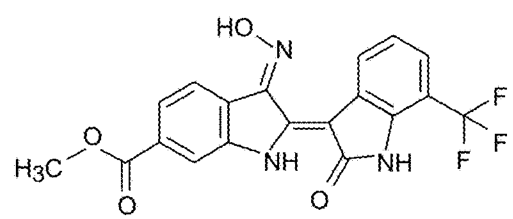 | 403.31 | 10mM | 200µl |
| 37 | 708 | 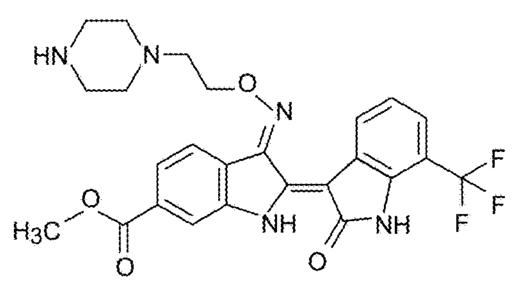 | 515.48 | 10mM | 200µl |
| 38 | 709 | 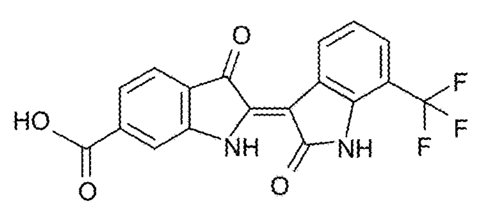 | 374.27 | 10mM | 200µl |

Fig. 1H

| IRD No. | ID #. | Structure | MW | [C] DMSO | DS Quantity |
|---|---|---|---|---|---|
| 39 | 710 | 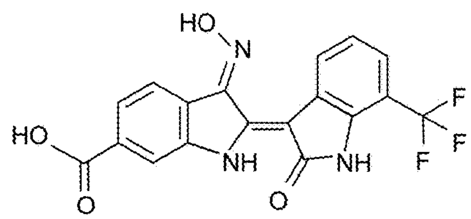 | 389.28 | 10mM | 100μl |
| 40 | 711 | 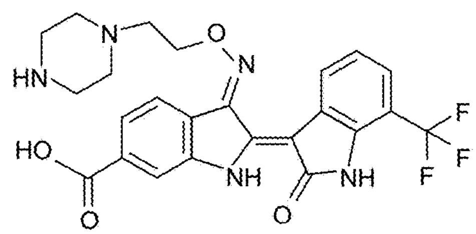 | 501.46 | 10mM | 100μl |
| 41 | 712 | 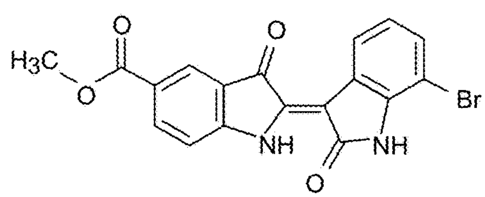 | 399.20 | 10mM | 200μl |
| 42 | 713 | 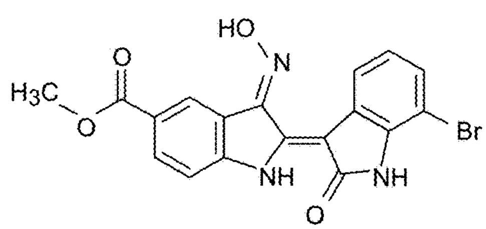 | 414.21 | 10mM | 200μl |
| 43 | 714 | 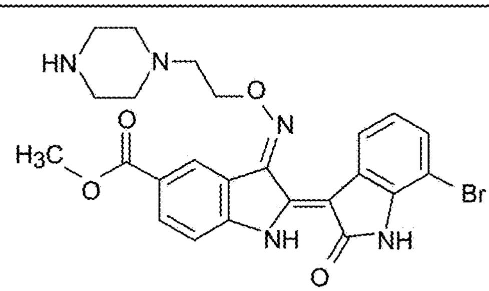 | 526.38 | 10mM | 200μl |

Fig. 1I

| IRD No. | ID #. | Structure | MW | [C] DMSO | DS Quantity |
|---|---|---|---|---|---|
| 44 | 715 | 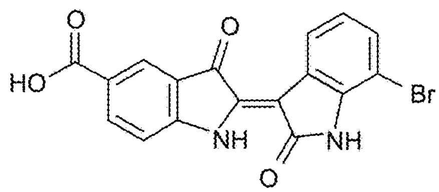 | 385.17 | 10mM | 200µl |
| 50 | 721 | 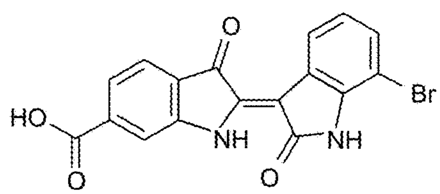 | 385.17 | 10mM | 200µl |
| 51 | 722 | 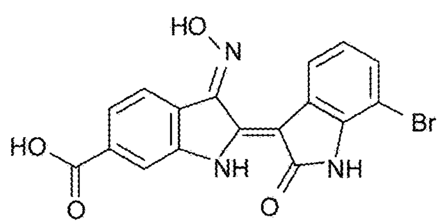 | 400.18 | 10mM | 200µl |
| 52 | 723 | 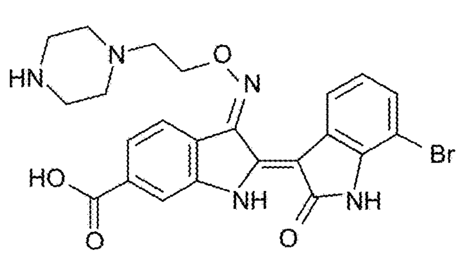 | 512.36 | 10mM | 200µl |

Fig. 1J

| IRD No. | ID #. | Structure | MW | [C] DMSO | DS Quantity |
|---|---|---|---|---|---|
| 54 | 725 | 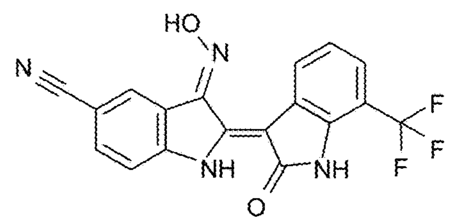 | 370.28 | 10mM | 100µl |
| 55 | 726 | 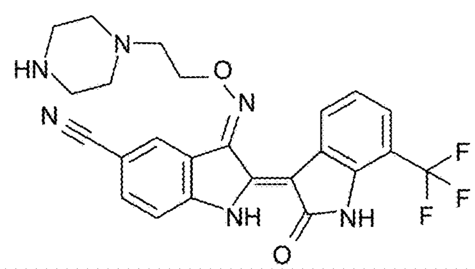 | 482.46 | 5mM | 200µl |
| 56 | 727 | 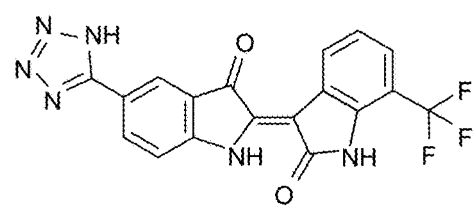 | 398.30 | 10mM | 200µl |
| 57 | 728 | 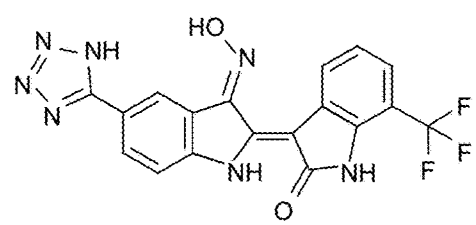 | 413.31 | 10mM | 200µl |
| 58 | 772 | 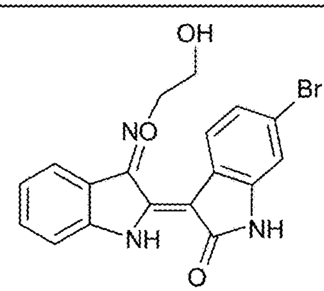 | 400.23 | 10mM | 200µl |

Fig. 1K

| IRD No. | ID #. | Structure | MW | [C] DMSO | DS Quantity |
|---|---|---|---|---|---|
| 59 | 773 | (structure with HO, OH, Br, N-O, NH, O) | 430.25 | 10mM | 200μl |
| 60 | 774 | (structure with NOH, NO2, NMe2, NH, O) | 365.34 | 10mM | 200μl |
| 61 | 775 | (structure with piperazine, Br, N-O, NH, O) | 468.35 | 10mM | 200μl |
| 62 | 776 | (structure with Cl⁻, *H3N, Br, NOH, NH, O) | 407.65 | 10mM | 200μl |
| 63 | 777 | (structure with H2N, Br, NOH, NH, O) | 371.19 | 10mM | 200μl |

Fig. 1L

| IRD No. | ID #. | Structure | MW | [C] DMSO | DS Quantity |
|---|---|---|---|---|---|
| 64 | 778 | (structure) | 455.31 | 10mM | 200µl |
| 65 | 779 | (structure) | 401.17 | 10mM | 200µl |
| 66 | 780 | (structure) | 356.17 | 10mM | 200µl |
| 68 | 788 | (structure) | 482.37 | 10mM | 200µl |
| 69 | 789 | (structure) | 555.30 | 10mM | 200µl |

Fig. 1M
| IRD No. | ID #. | Structure | MW | [C] DMSO | DS Quantity |
|---|---|---|---|---|---|
| 70 | 790 | 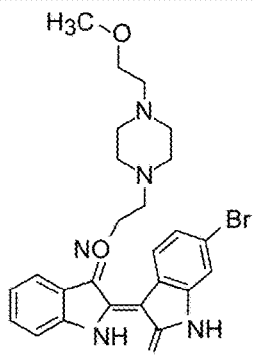 | 526.43 | 10mM | 200μl |
| 71 | 791 | 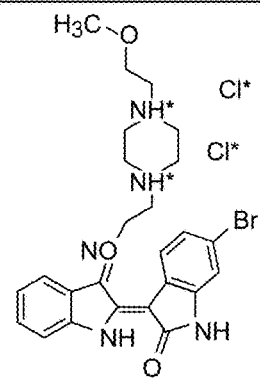 | 599.35 | 10mM | 200μl |
| 72 | 793 | 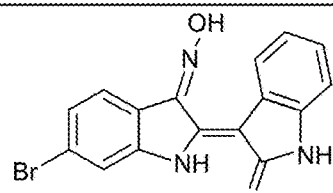 | 356.17 | 10mM | 200μl |
| 73 | 794 | 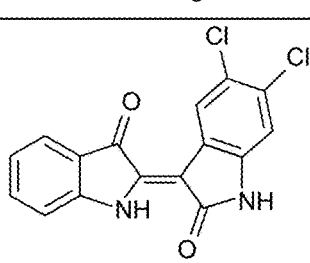 | 331.15 | 10mM | 200μl |
| 76 | 797 | 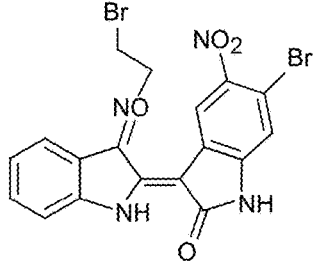 | 508.12 | 10mM | 200μl |

Fig. 1N

| IRD No. | ID #. | Structure | MW | [C] DMSO | DS Quantity |
|---|---|---|---|---|---|
| 77 | 798 | 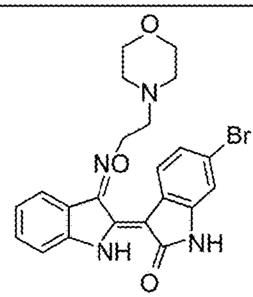 | 469.33 | 10mM | 200µl |
| 78 | 799 | 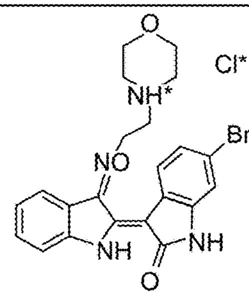 | 505.79 | 10mM | 200µl |
| 79 | 800 | 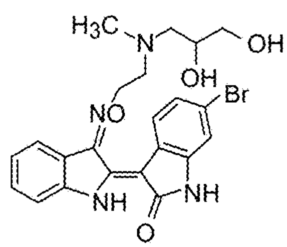 | 487.35 | 10mM | 200µl |
| 80 | 801 | 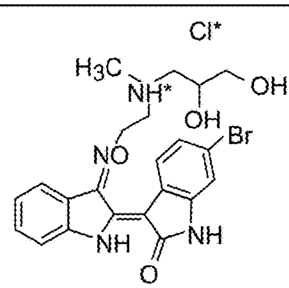 | 523.81 | 10mM | 200µl |
| 81 | 802 | 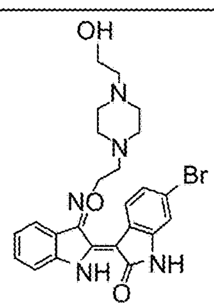 | 512.40 | 10mM | 200µl |

Fig. 1O
| IRD No. | ID #. | Structure | MW | [C] DMSO | DS Quantity |
|---|---|---|---|---|---|
| 82 | 803 | 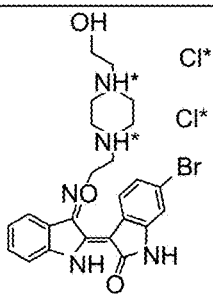 | 585.32 | 10mM | 200μl |
| 83 | 804 | 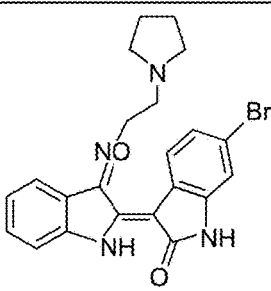 | 453.33 | 10mM | 200μl |
| 84 | 805 | 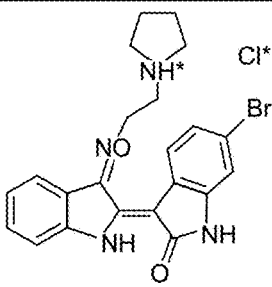 | 489.79 | 10mM | 200μl |
| 85 | 806 | 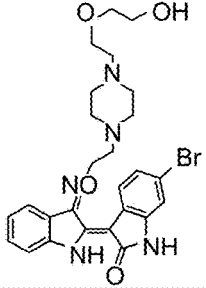 | 556.45 | 10mM | 200μl |
| 86 | 807 | 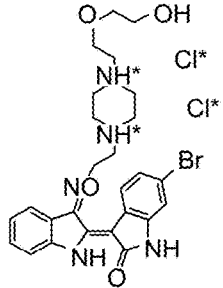 | 629.37 | 10mM | 200μl |

Fig. 1P
| IRD No. | ID #. | Structure | MW | [C] DMSO | DS Quantity |
|---|---|---|---|---|---|
| 87 | 810 | 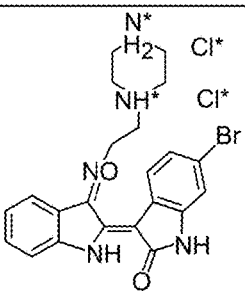 | 541.27 | 10mM | 200μl |
| 88 | 815 | 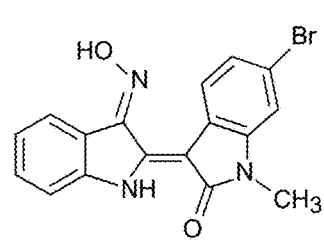 | 370.20 | 10mM | 200μl |
| 89 | 820 | 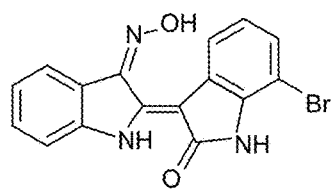 | 356.17 | 10mM | 200μl |
| 90 | 821 | 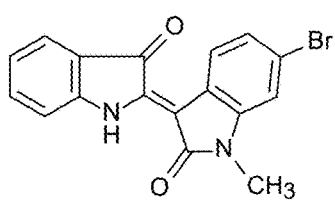 | 355.19 | 10mM | 200μl |
| 91 | 822 | 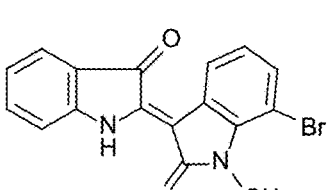 | 355.19 | 10mM | 200μl |

Fig. 1Q

| IRD No. | ID #. | Structure | MW | [C] DMSO | DS Quantity |
|---|---|---|---|---|---|
| 92 | 824 | 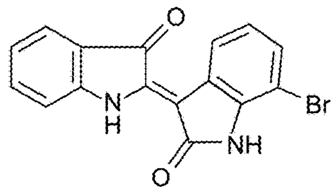 | 341.16 | 10mM | 200μl |
| 93 | 825 | 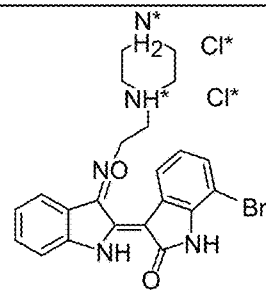 | 541.27 | 10mM | 200μl |
| 94 | 827 | 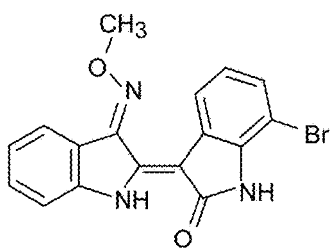 | 370.20 | 10mM | 200μl |
| 95 | 828 | 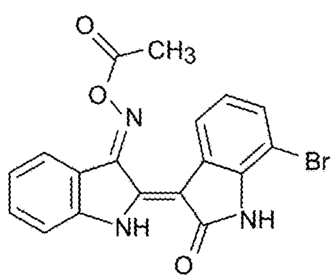 | 398.21 | 10mM | 200μl |
| 96 | 829 | 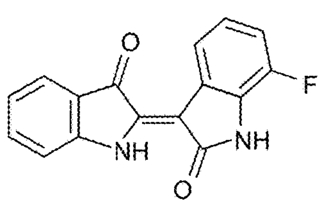 | 280.25 | 10mM | 200μl |

Fig. 1R
| IRD No. | ID #. | Structure | MW | [C] DMSO | DS Quantity |
|---|---|---|---|---|---|
| 97 | 830 | 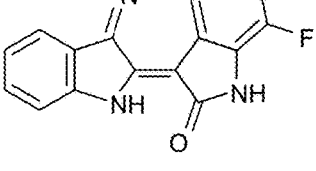 | 295.27 | 10mM | 200µl |
| 98 | 831 | 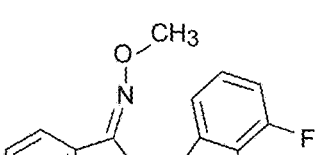 | 309.29 | 10mM | 200µl |
| 99 | 832 | 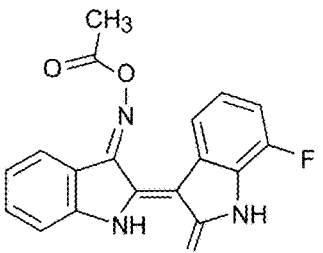 | 337.30 | 10mM | 200µl |
| 100 | 833 | 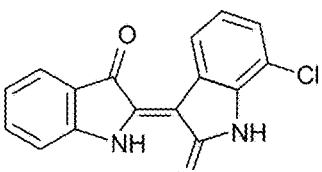 | 296.71 | 10mM | 200µl |
| 101 | 834 | 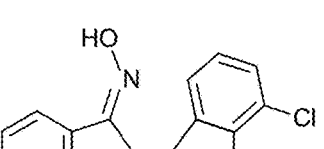 | 311.72 | 10mM | 200µl |

Fig. 1S

| IRD No. | ID #. | Structure | MW | [C] DMSO | DS Quantity |
|---------|-------|-----------|------|----------|-------------|
| 102 | 835 | 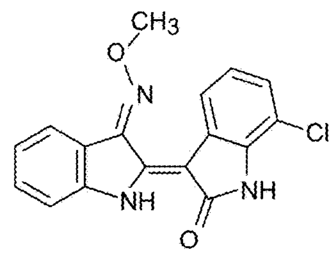 | 325.75 | 10mM | 200µl |
| 103 | 836 | 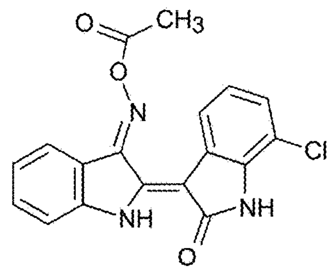 | 353.76 | 10mM | 200µl |
| 104 | 837 | 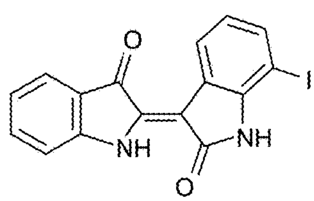 | 388.16 | 10mM | 200µl |
| 105 | 838 | 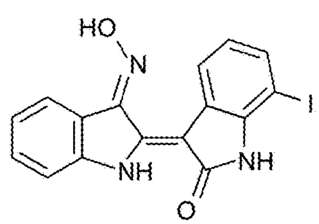 | 403.17 | 10mM | 200µl |
| 106 | 839 | 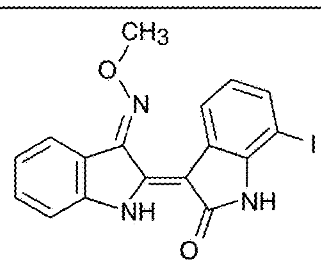 | 417.20 | 3mM | 400µl |

Fig. 1T

| IRD No. | ID #. | Structure | MW | [C] DMSO | DS Quantity |
|---|---|---|---|---|---|
| 107 | 840 | 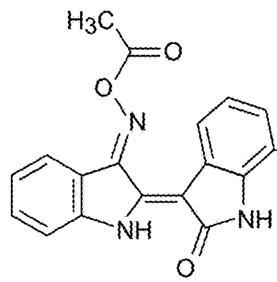 | 445.21 | 10mM | 200μl |
| 108 | 841 | 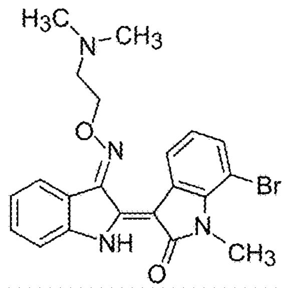 | 441.32 | 3,8mM | 400μl |
| 109 | 842 | 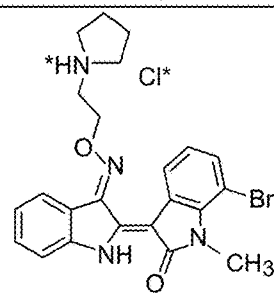 | 503.82 | 10mM | 100μl |
| 111 | 852 | 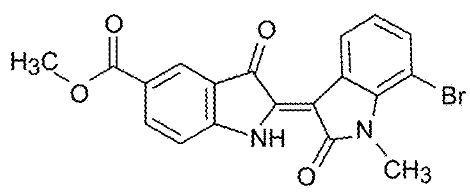 | 413.22 | 10mM | 200μl |
| 114 | 856 | 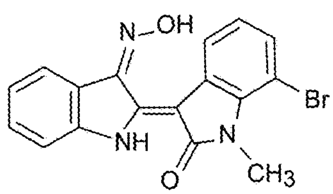 | 370.20 | 10mM | 200μl |

Fig. 1U

| IRD No. | ID #. | Structure | MW | [C] DMSO | DS Quantity |
|---|---|---|---|---|---|
| 115 | 857 | 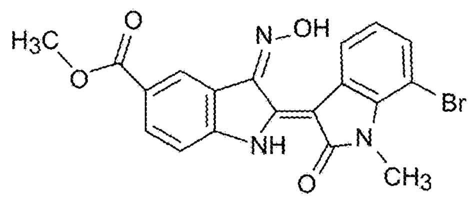 | 428.24 | 10mM | 200µl |
| 116 | 858 | 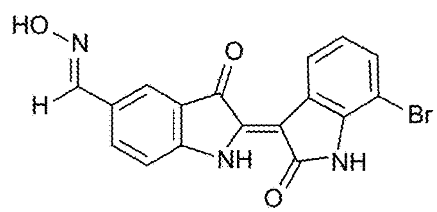 | 384.18 | 10mM | 200µl |
| 118 | 860 | 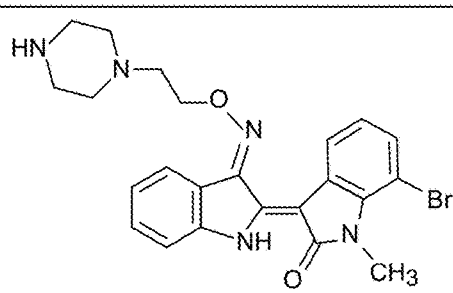 | 482.37 | 10mM | 100µl |
| 119 | 861 | 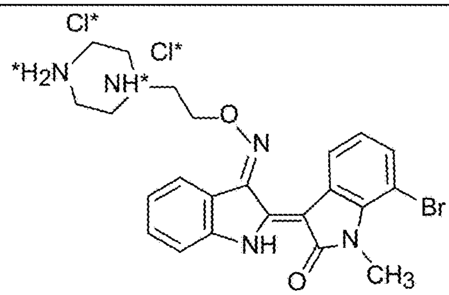 | 555.30 | 10mM | 200µl |
| 120 | 862 | 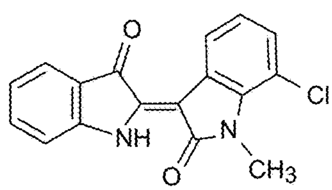 | 310.73 | 10mM | 200µl |

Fig. 1V
| IRD No. | ID #. | Structure | MW | [C] DMSO | DS Quantity |
|---|---|---|---|---|---|
| 121 | 863 | 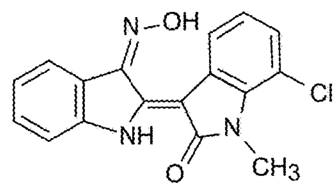 | 325.75 | 10mM | 200µl |
| 122 | 864 | 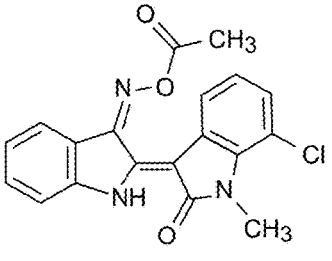 | 367.79 | 10mM | 200µl |
| 123 | 865 | 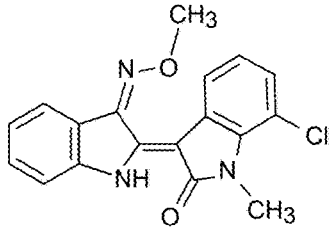 | 339.78 | 10mM | 200µl |
| 124 | 867 | 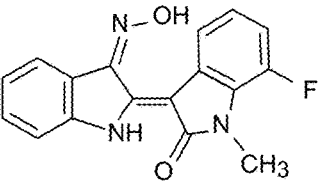 | 309.29 | 10mM | 200µl |
| 125 | 870 | 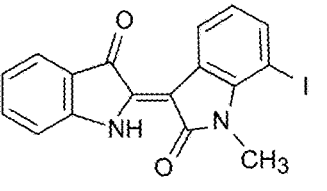 | 402.19 | 10mM | 200µl |

Fig. 1W

| IRD No. | ID #. | Structure | MW | [C] DMSO | DS Quantity |
|---|---|---|---|---|---|
| 126 | 871 | 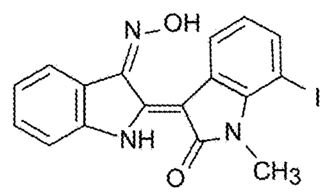 | 417.20 | 10mM | 200µl |
| 127 | 872 | 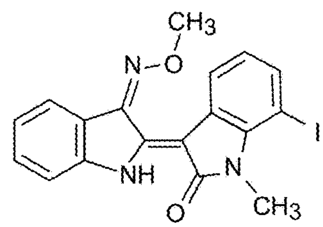 | 431.23 | 10mM | 200µl |
| 128 | 873 | 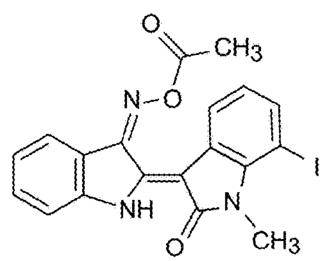 | 459.24 | 10mM | 200µl |
| 129 | 874 | 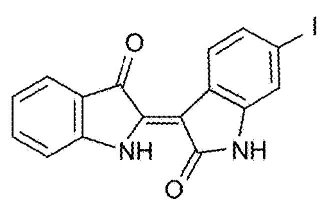 | 388.16 | 10mM | 200µl |
| 130 | 876 | 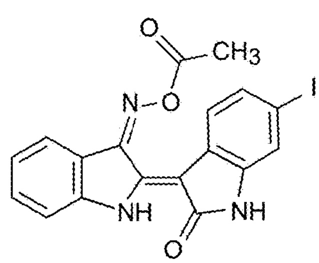 | 445.21 | 10mM | 200µl |

Fig. 1X

| IRD No. | ID #. | Structure | MW | [C] DMSO | DS Quantity |
|---------|-------|-----------|------|----------|-------------|
| 131 | 877 | 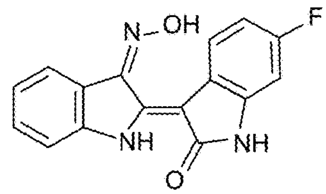 | 295.27 | 10mM | 200µl |
| 132 | 878 | 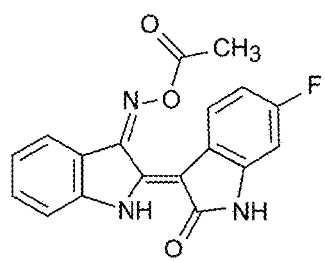 | 337.30 | 10mM | 100µl |
| 133 | 879 | 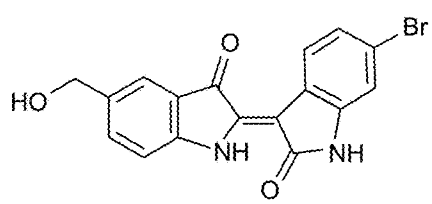 | 371.19 | 10mM | 200µl |
| 148 | 899 | 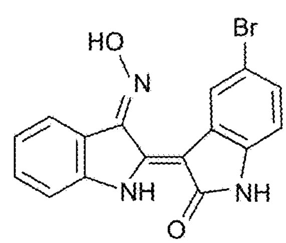 | 356.17 | 10mM | 200µl |
| 149 | 900 | 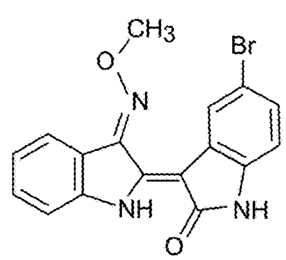 | 370.20 | 10mM | 200µl |

| IRD No. | ID #. | Structure | MW | [C] DMSO | DS Quantity |
|---|---|---|---|---|---|
| 150 | 901 | 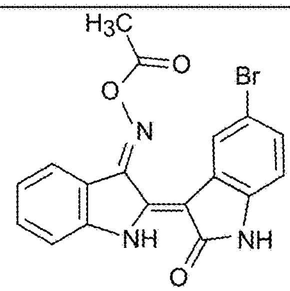 | 398.21 | 10mM | 200µl |

Fig. 2A

| IRD No. | ID #. | Structure | MW | [C] DMSO | DS Quantity |
|---|---|---|---|---|---|
| 1 | 235 | 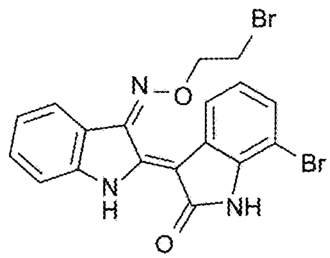 | 463.12 | 10mM | 200µl |
| 2 | 351 | 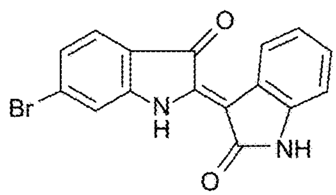 | 341.16 | 10mM | 200µl |
| 33 | 704 | 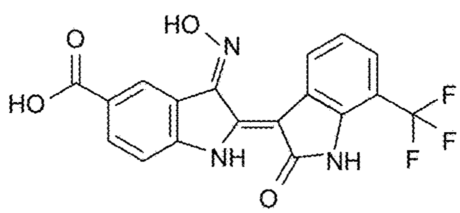 | 389.28 | 10mM | 50µl |
| 45 | 716 | 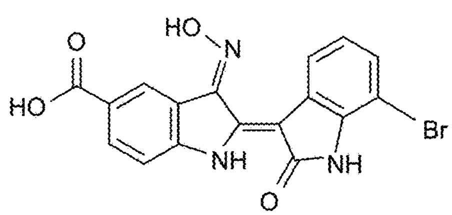 | 400.18 | 10mM | 150µl |

Fig. 2B
| IRD No. | ID #. | Structure | MW | [C] DMSO | DS Quantity |
|---|---|---|---|---|---|
| 47 | 718 | 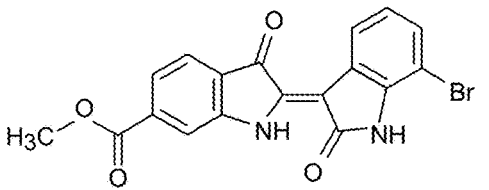 | 399.20 | 5mM | 400μl |
| 48 | 719 | 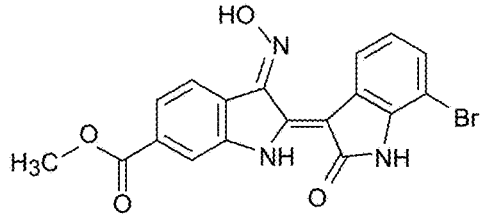 | 414.21 | 10mM | 50μl |
| 49 | 720 | 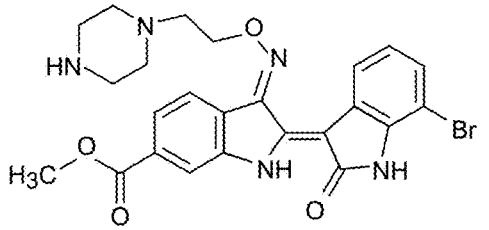 | 526.38 | 10mM | 50μl |
| 53 | 724 | 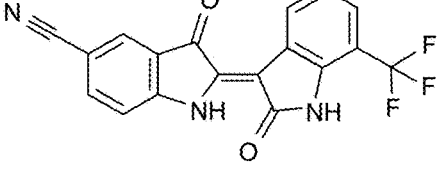 | 355.27 | 10mM | 50μl |
| 67 | 787 | 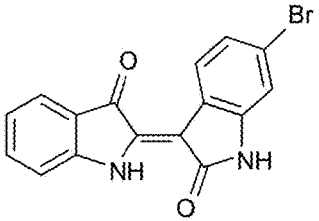 | 341.16 | 10mM | 200μl |

Fig. 2C

| IRD No. | ID #. | Structure | MW | [C] DMSO | DS Quantity |
|---|---|---|---|---|---|
| 74 | 795 | (structure) | 386.16 | 5mM | 400µl |
| 75 | 796 | (structure) | 443.21 | 10mM | 100µl |
| 110 | 843 | (structure) | 477.78 | 5mM | 150µl |
| 112 | 853 | (structure) | 369.17 | 10mM | 200µl |
| 113 | 855 | (structure) | 371.19 | 5mM | 200µl |

Fig. 2D

| IRD No. | ID #. | Structure | MW | [C] DMSO | DS Quantity |
|---|---|---|---|---|---|
| 114 | 859 | 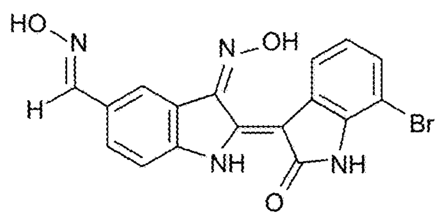 | 399.20 | 10mM | 100µl |
| 134 | 880 | 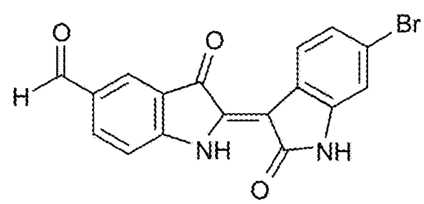 | 369.17 | 10mM | 100µl |
| 135 | 881 | 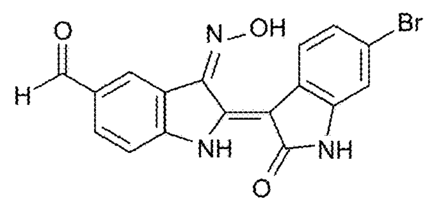 | 384.18 | 10mM | 100µl |
| 136 | 882 | 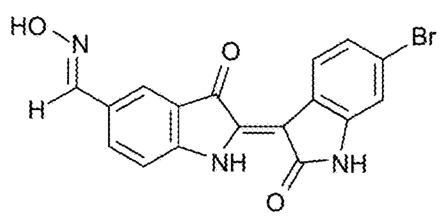 | 384.18 | 10mM | 100µl |
| 137 | 884 | 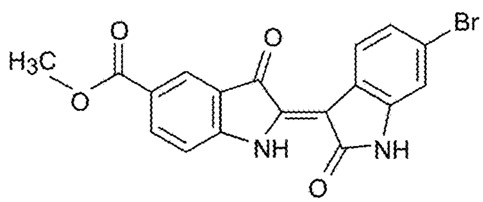 | 399.20 | 5mM | 200µl |

Fig. 2E

| IRD No. | ID #. | Structure | MW | [C] DMSO | DS Quantity |
|---|---|---|---|---|---|
| 138 | 885 | 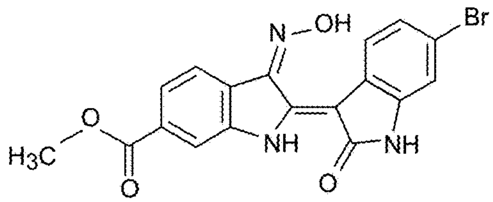 | 414.21 | 10mM | 200µl |
| 139 | 886 | 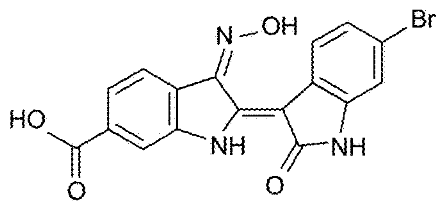 | 400.18 | 10mM | 50µl |
| 140 | 887 | 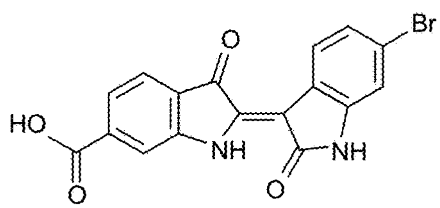 | 385.17 | 10mM | 200µl |
| 141 | 888 | 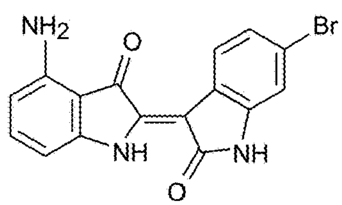 | 356.17 | 10mM | 100µl |
| 142 | 889 | 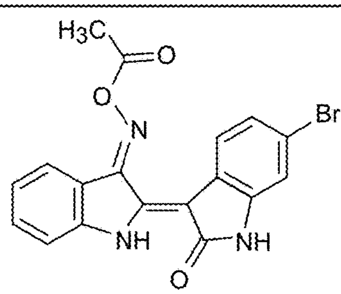 | 398.21 | 10mM | 100µl |

Fig. 2F

| IRD No. | ID #. | Structure | MW | [C] DMSO | DS Quantity |
|---|---|---|---|---|---|
| 143 | 891 | 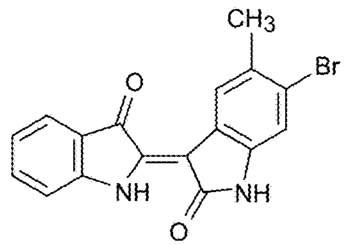 | 355.19 | 10mM | 200µl |
| 144 | 893 | 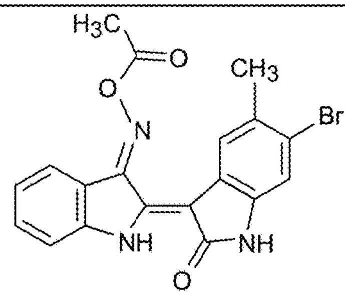 | 412.24 | 10mM | 100µl |
| 145 | 894 | 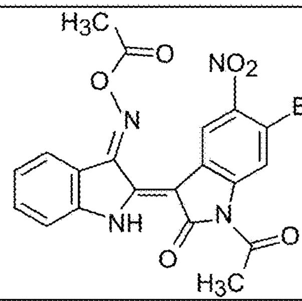 | 485.24 | 5mM | 400µl |
| 146 | 895 | 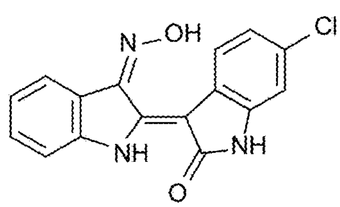 | 311.72 | 10mM | 50µl |
| 147 | 897 | 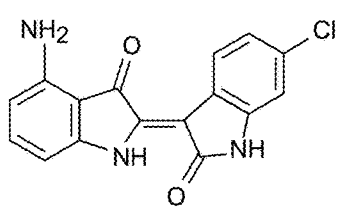 | 311.72 | 10mM | 50µl |

Fig. 2G

| IRD No. | ID #. | Structure | MW | [C] DMSO | DS Quantity |
|---|---|---|---|---|---|
| 158 | 1200 | 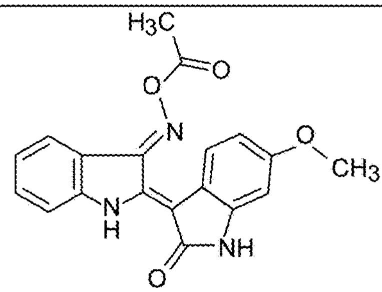 | 349.34 | 10mM | 100µl |
| 159 | 1202 | 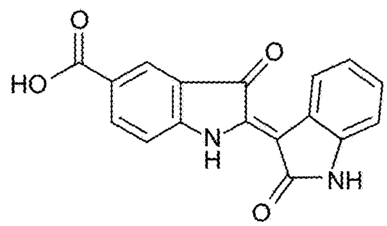 | 306.27 | 10mM | 200µl |
| 160 | 1203 | 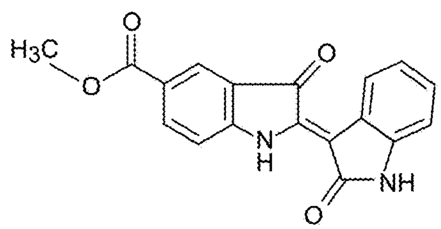 | 320.30 | 10mM | 200µl |
| 161 | 1204 | 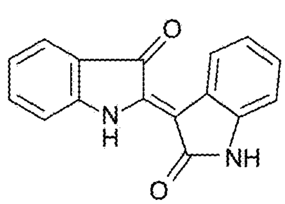 | 262.26 | 10mM | 200µl |
| 162 | 1205 | 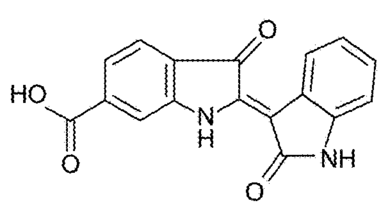 | 306.27 | 10mM | 200µl |

Fig. 2H
| IRD No. | ID #. | Structure | MW | [C] DMSO | DS Quantity |
|---|---|---|---|---|---|
| 163 | 1206 | 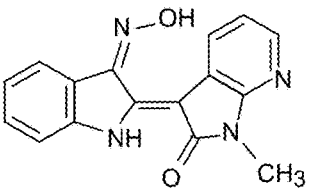 | 292.29 | 5mM | 200µl |
| 164 | 1207 | 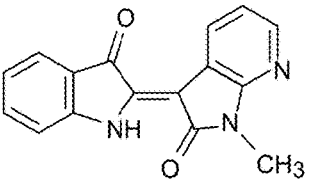 | 277.28 | 10mM | 200µl |
| 165 | 1208 | 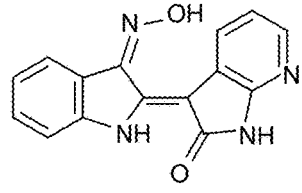 | 278.27 | 5mM | 150µl |
| 166 | 1210 | 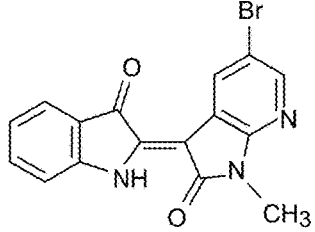 | 356.17 | 5mM | 200µl |
| 167 | 1211 | 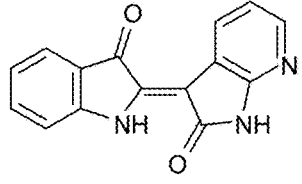 | 263.25 | 10mM | 100µl |

Fig. 2I

| IRD No. | ID #. | Structure | MW | [C] DMSO | DS Quantity |
|---|---|---|---|---|---|
| 168 | 1212 | 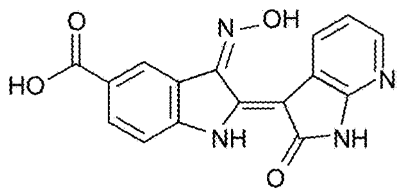 | 321.29 | 10mM | 200μl |
| 169 | 1214 | 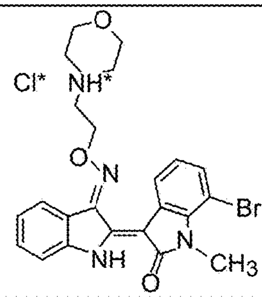 | 519.82 | 10mM | 200μl |
| 170 | 1215 | 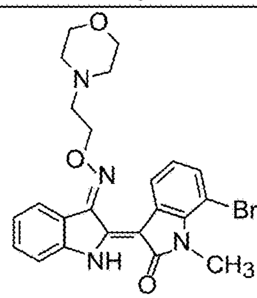 | 483.36 | 5mM | 200μl |
| 171 | 1216 | 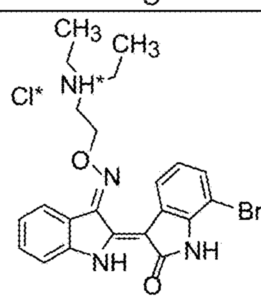 | 491.81 | 5mM | 200μl |
| 172 | 1217 | 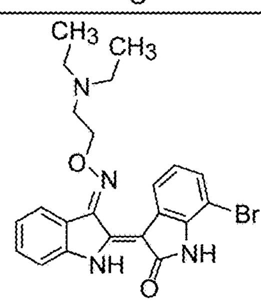 | 455.35 | 5mM | 200μl |

Fig. 2J

| IRD No. | ID #. | Structure | MW | [C] DMSO | DS Quantity |
|---|---|---|---|---|---|
| 173 | 1218 | 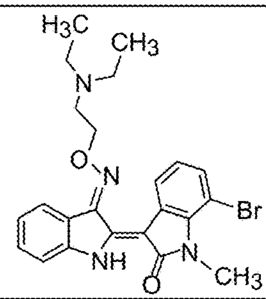 | 441.32 | 3mM | 200µl |
| 174 | 1220 | 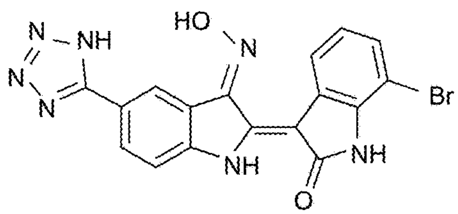 | 424.21 | 10mM | 100µl |
| 175 | 1221 | 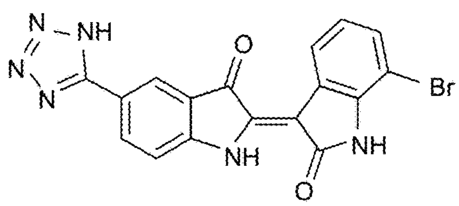 | 409.20 | 10mM | 100µl |
| 176 | 1222 | 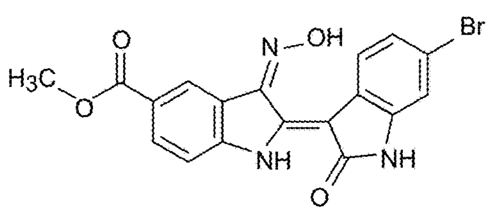 | 414.21 | 10mM | 48µl |
| 177 | 1223 | 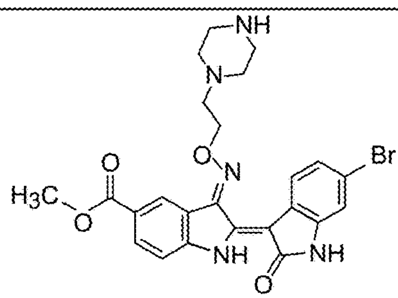 | 526.38 | 5mM | 130µl |

Fig. 2K

| IRD No. | ID #. | Structure | MW | [C] DMSO | DS Quantity |
|---|---|---|---|---|---|
| 178 | 1224 | 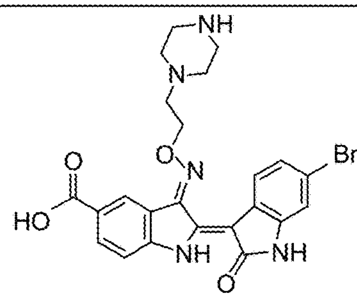 | 512.36 | 10mM | 150µl |
| 179 | 1225 | 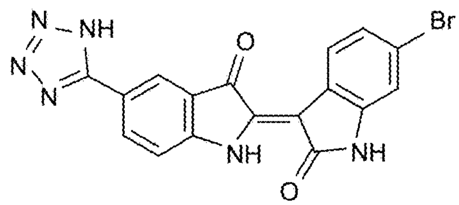 | 409.20 | 10mM | 200µl |
| 180 | 1226 | 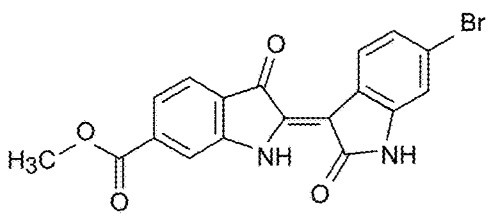 | 399.20 | 5mM | 200µl |
| 181 | 1227 | 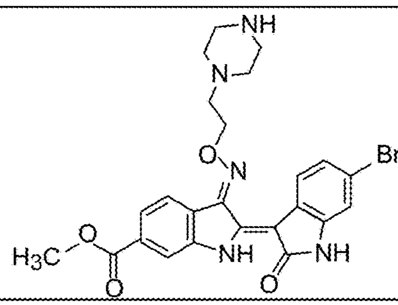 | 526.38 | 5mM | 180µl |
| 182 | 1228 | 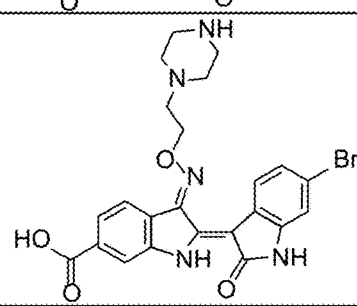 | 512.36 | 5mM | 200µl |

Fig. 2L

| IRD No. | ID #. | Structure | MW | [C] DMSO | DS Quantity |
|---|---|---|---|---|---|
| 183 | 1230 | 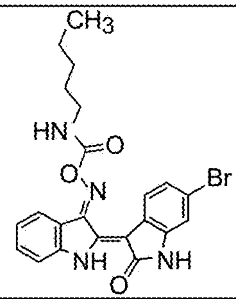 | 469.33 | 5mM | 200µl |
| 184 | 1231 | 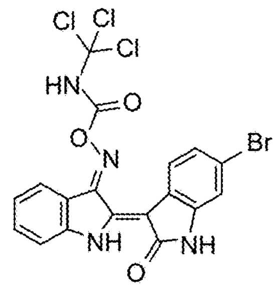 | 516.56 | 10mM | 200µl |
| 185 | 1232 | 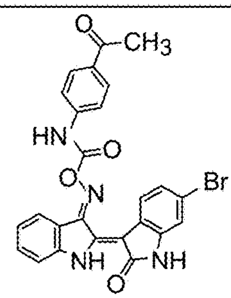 | 517.33 | 5mM | 200µl |
| 186 | 1233 | 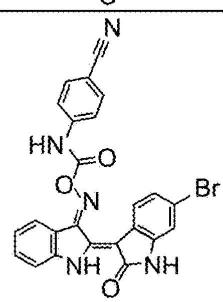 | 500.30 | 5mM | 200µl |
| 187 | 1234 | 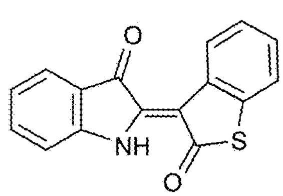 | 279.31 | 5mM | 400µl |

| IRD No. | ID #. | Structure | MW | [C] DMSO | DS Quantity |
|---|---|---|---|---|---|
| 188 | 1235 | 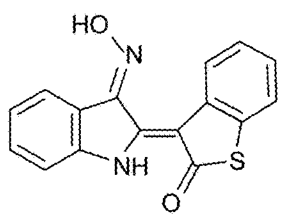 | 294.328 | 5mM | 400µl |

Fig. 3A-1

Plate 3

| | 1 | 2 | 3 | 4 | 5 | 6 | 7 | 8 | 9 | 10 | 11 | 12 |
|---|---|---|---|---|---|---|---|---|---|---|---|---|
| A | | 235 | 351 | 704 | 716 | 717 | 718 | 719 | 720 | 724 | 787 | 795 |
| B | | 796 | 843 | 853 | 855 | 859 | 880 | 881 | 882 | 884 | 885 | 886 |
| C | | 887 | 888 | 889 | 891 | 893 | 894 | 895 | 897 | | | |
| D | | 1204 | 1205 | 1206 | 1207 | 1208 | 1210 | 1211 | 1212 | 1214 | 1215 | 1216 |
| E | | 1217 | 1218 | 1220 | 1221 | 1222 | 1223 | 1224 | 1225 | 1226 | 1227 | 1228 |
| F | | 1230 | 1231 | 1232 | 1233 | 1234 | 1235 | | | | | |

Viability (% control) Experiments in duplicate. Average values

A2058 melanoma

Plate 1 — Screening at 1 uM

| | 2 | 3 | 4 | 5 | 6 | 7 | 8 | 9 | 10 | 11 | 12 |
|---|---|---|---|---|---|---|---|---|---|---|---|
| A | 108.303 | 113.3607 | 99.4581 | 97.57605 | 101.4495 | 77.77595 | 84.07701 | 92.66228 | 98.50206 | 103.69 | 105.4258 |
| B | 81.93092 | 116.1428 | 88.07258 | 97.78239 | 76.71783 | 91.85981 | 80.38768 | 83.20613 | 84.30665 | 43.77208 | 92.5662 |
| C | 105.8931 | 116.5013 | 95.09604 | 122.2175 | 100.3368 | 96.57033 | 97.7127 | 100.9977 | 72.6127 | 102.1113 | 70.09105 |
| D | 123.6026 | 117.6194 | 112.0635 | 100.4078 | 88.48655 | 103.8434 | 88.21416 | 97.21667 | 92.63879 | 108.2566 | 100.4211 |
| E | 105.2655 | 110.5263 | 87.13511 | 93.94677 | 3.492624 | 79.96825 | 95.93363 | 70.83036 | 91.36014 | 77.9703 | 107.8545 |
| F | 111.3717 | 83.76404 | 98.43526 | 102.4429 | 81.38521 | 95.95874 | | | | | |

Plate 2 — Screening at 10 uM

| | 2 | 3 | 4 | 5 | 6 | 7 | 8 | 9 | 10 | 11 | 12 |
|---|---|---|---|---|---|---|---|---|---|---|---|
| A | 100.184 | 90.54916 | 99.66241 | 92.18956 | 102.6341 | 72.56613 | 32.78436 | 85.25957 | 109.9232 | 97.74978 | 53.75795 |
| B | 14.22837 | 96.57073 | 77.26749 | 93.07063 | 10.327 | 85.90015 | 33.07898 | 83.98734 | 101.5855 | 7.046378 | 115.5863 |
| C | 92.71674 | 98.87471 | 18.96838 | 83.36994 | 91.63781 | 30.71968 | 27.3437 | 98.41376 | 75.59338 | 114.999 | 89.52554 |
| D | 96.62088 | 95.95473 | 77.20544 | 24.47942 | 46.80396 | 63.13508 | 68.6608 | 89.24163 | 112.0624 | 108.8557 | 22.67407 |
| E | 32.97766 | 6.626065 | 110.4634 | 90.59714 | 5.508669 | 86.05498 | 95.38572 | 104.5376 | 81.07389 | 100.7984 | |
| F | 90.96748 | 5.928188 | 80.12621 | 102.9002 | 88.11432 | 112.066 | | | | | |

Fig. 3A-2

DU145 prostate cancer

Plate 1 — Screening at 1 μM

| | 1 | 2 | 3 | 4 | 5 | 6 | 7 | 8 | 9 | 10 | 11 | 12 |
|---|---|---|---|---|---|---|---|---|---|---|---|---|
| A | | 90.39287 | 94.20044 | 90.63143 | 87.86488 | 93.77176 | 88.78971 | 82.0187 | 78.17353 | 95.52845 | 84.90815 | 89.08077 |
| B | | 75.98377 | 88.2863 | 79.54565 | 73.3141 | 54.80542 | 85.46264 | 76.72986 | 92.74884 | 95.71566 | 57.90091 | 95.06464 |
| C | | 98.11932 | 81.79246 | 73.93729 | 77.98261 | 69.95763 | 69.9497 | 83.60256 | 95.18936 | 93.7074 | 83.2346 | 91.38904 |
| D | | 95.34193 | 91.71729 | 92.43508 | 78.05856 | 71.25815 | 87.30457 | 70.60678 | 79.95766 | 93.7074 | 83.077 | 83.63366 |
| E | | 91.07385 | 90.59965 | 100.1406 | 93.29031 | 20.29864 | 83.24632 | 80.21288 | 86.29106 | 90.79553 | 89.62875 | 87.55545 |
| F | | 89.33673 | 83.00836 | 82.96426 | 97.90969 | 84.24811 | 83.06182 | | | | | |

Plate 2 — Screening at 10 μM

| | 1 | 2 | 3 | 4 | 5 | 6 | 7 | 8 | 9 | 10 | 11 | 12 |
|---|---|---|---|---|---|---|---|---|---|---|---|---|
| A | | 87.39503 | 623.23031 | 94.70534 | 92.60418 | 97.16641 | 75.68721 | 46.44511 | 91.54935 | 82.27726 | 58.17715 | 50.4181 |
| B | | 25.87467 | 73.24946 | 93.17139 | 81.5603 | 19.939 | 88.08566 | 21.42542 | 65.80654 | 64.20917 | 10.73024 | 90.18937 |
| C | | 79.72766 | 71.3422 | 29.50941 | 71.51317 | 42.99766 | 26.73424 | 24.14471 | 92.73762 | 52.21689 | 77.19153 | 80.16895 |
| D | | 86.43534 | 86.16005 | 78.46569 | 52.78198 | 30.97996 | 64.4385 | 62.06334 | 83.57518 | 70.6257 | 71.84728 | 35.71947 |
| E | | 29.07398 | 12.74256 | 89.30724 | 91.04463 | 8.519789 | 80.26741 | 78.21288 | 91.03766 | 84.53396 | 79.57715 | 90.6961 |
| F | | 75.65674 | 9.165819 | 72.23848 | 74.24118 | 41.33065 | 71.32009 | | | | | |

KCL-22 CML

Plate 1 — Screening at 1 μM

| | 1 | 2 | 3 | 4 | 5 | 6 | 7 | 8 | 9 | 10 | 11 | 12 |
|---|---|---|---|---|---|---|---|---|---|---|---|---|
| A | | 100.8228 | 103.552 | 93.51278 | 94.52695 | 102.1588 | 95.0765 | 96.20628 | 85.47652 | 99.4807 | 88.57579 | 90.21432 |
| B | | 78.91396 | 87.92719 | 90.58228 | 88.97574 | 87.49737 | 86.66397 | 69.44345 | 93.14312 | 84.9905 | 64.10876 | 99.01384 |
| C | | 91.22172 | 84.54787 | 78.82338 | 83.37846 | 96.76898 | 87.64529 | 76.81534 | 82.43177 | 75.18357 | 79.27575 | 82.66915 |
| D | | 95.22161 | 86.57845 | 82.12297 | 81.55764 | 89.95342 | 73.31105 | 83.97183 | 75.66903 | 78.31947 | 78.99046 | 92.56328 |
| E | | 76.21577 | 81.28096 | 88.49366 | 95.59338 | 19.95139 | 84.2981 | 97.19076 | 82.5032 | 93.57744 | 87.18027 | 104.7912 |
| F | | 94.49821 | 81.42832 | 87.35412 | 92.56553 | 93.98134 | 87.78604 | | | | | |

Plate 2 — Screening at 10 μM

| | 1 | 2 | 3 | 4 | 5 | 6 | 7 | 8 | 9 | 10 | 11 | 12 |
|---|---|---|---|---|---|---|---|---|---|---|---|---|

Fig. 3B

Plate 3 (Continued)

|   | 1 | 2 | 3 | 4 | 5 | 6 | 7 | 8 | 9 | 10 | 11 | 12 |
|---|---|---|---|---|---|---|---|---|---|----|----|----|
| A |   | 77.99944 | 89.46968 | 98.86105 | 89.50966 | 98.78892 | 60.2243 | 44.14104 | 95.81017 | 87.61247 | 94.61283 | 72.50378 |
| B |   | 24.31399 | 56.50493 | 72.1412 | 74.92526 | 20.61059 | 87.09207 | 20.37552 | 90.60813 | 77.99704 | 21.64755 | 97.52902 |
| C |   | 90.64995 | 61.05061 | 35.99728 | 81.67332 | 46.42433 | 21.60462 | 29.67625 | 73.75267 | 42.09648 | 74.41476 | 79.54195 |
| D |   | 82.15702 | 83.62994 | 74.39897 | 49.69303 | 41.23458 | 66.58091 | 55.899 | 92.30018 | 49.17813 | 61.43265 | 49.97103 |
| E |   | 33.0222 | 19.3459 | 85.72924 | 15.73681 | 63.36821 | 85.02438 | 88.21106 | 88.43383 | 73.69728 | 91.83244 |
| F |   | 83.53164 | 17.88414 | 59.27909 | 77.6174 | 55.19748 | 67.97295 | 89.07824 | 101.4702 | 100.0107 | 105.3729 | 115.6176 |

T315I mutant KCL-22 CML

Plate 1

Screening at 1 uM

|   | 1 | 2 | 3 | 4 | 5 | 6 | 7 | 8 | 9 | 10 | 11 | 12 |
|---|---|---|---|---|---|---|---|---|---|----|----|----|
| A |   | 98.12603 | 101.3548 | 102.0958 | 86.95523 | 99.03675 | 86.39949 | 90.10173 | 91.05852 | 94.58193 | 93.0083 | 95.85797 |
| B |   | 79.77096 | 88.30961 | 99.47228 | 87.06213 | 77.37185 | 85.04683 | 79.14204 | 85.41781 | 91.22652 | 48.484 | 95.6003 |
| C |   | 91.84213 | 92.62229 | 92.08724 | 78.58113 | 92.15524 | 82.68566 | 84.97145 | 79.4315 | 90.33133 | 88.62838 | 88.69266 |
| D |   | 90.93707 | 92.69767 | 91.24673 | 83.23795 | 80.38828 | 77.47358 | 81.18816 | 90.19781 | 100.8896 | 89.01488 | 93.6786 |
| E |   | 92.48483 | 91.25929 | 98.29921 | 85.66071 | 16.17225 | 89.75193 | 95.77865 | 88.7508 | 91.03438 | 95.48354 | 122.7667 |
| F |   | 86.73254 | 73.24884 | 98.73474 | 93.96411 | 74.81261 | 95.67272 |

Plate 2

Screening at 10 uM

|   | 1 | 2 | 3 | 4 | 5 | 6 | 7 | 8 | 9 | 10 | 11 | 12 |
|---|---|---|---|---|---|---|---|---|---|----|----|----|
| A |   | 89.3272 | 104.935 | 99.82762 | 87.90063 | 99.31461 | 63.67413 | 27.83249 | 91.8362 | 103.5088 | 96.85137 | 78.7728 |
| B |   | 22.11166 | 57.24019 | 70.70693 | 72.83986 | 23.31756 | 84.75906 | 23.36758 | 91.14686 | 90.72148 | 20.80713 | 102.5147 |
| C |   | 81.77216 | 69.37012 | 45.34655 | 68.45372 | 70.92157 | 20.19372 | 40.21856 | 84.60189 | 61.26888 | 88.14507 | 89.6238 |
| D |   | 91.31539 | 81.3906 | 75.48085 | 41.63484 | 51.85144 | 59.47247 | 69.0203 | 95.54507 | 81.96942 | 77.3179 | 53.7928 |
| E |   | 36.0875 | 18.25555 | 90.28652 | 78.66465 | 19.14748 | 72.84803 | 78.91476 | 99.1099 | 86.47797 | 84.68455 | 103.1469 |
| F |   | 91.45801 | 18.76289 | 72.2481 | 90.39189 | 68.00386 | 70.7715 |

SKOV3 ovarian

Plate 1

Screening at 1 uM

|   | 1 | 2 | 3 | 4 | 5 | 6 | 7 | 8 | 9 | 10 | 11 | 12 |
|---|---|---|---|---|---|---|---|---|---|----|----|----|
| A |   | 88.12959 | 108.0391 | 82.06052 | 80.65592 | 76.99139 | 98.98433 | 95.1394 | 95.39172 | 93.86846 | 108.3794 | 131.6413 |
| B |   | 69.29 | 84.62493 | 82.2065 | 67.78087 | 44.07322 | 93.01291 | 61.27958 | 92.43357 | 78.26301 | 102.7486 | 115.0256 |
| C |   | 83.87049 | 75.26935 | 60.42654 | 69.59493 | 56.0319 | 61.21148 | 60.05033 | 86.11219 | 76.43209 | 90.63 | 97.8389 |
| D |   | 66.85108 | 69.47355 | 78.58728 | 76.21896 | 47.62481 | 68.92655 | 61.97733 | 78.86756 | 84.43523 | 91.87176 | 86.94114 |
| E |   | 67.14644 | 69.60836 | 74.81286 | 69.5027 | 8.345398 | 67.49074 | 75.18172 | 92.72187 | 72.27414 | 80.69762 | 98.14558 |
| F |   | 66.36489 | 51.38225 | 81.39672 | 82.48911 | 71.78313 | 67.54018 |

Fig. 3C-1

Plates 1 and 2

Plate 1

|   | 1 | 2 | 3 | 4 | 5 | 6 | 7 | 8 | 9 | 10 | 11 | 12 |
|---|---|---|---|---|---|---|---|---|---|----|----|----|
| A |   | 673 | 675 | 676 | 677 | 678 | 679 | 680 | 681 | 682 | 683 |  |
| B |   | N/A | 686 | 687 | 688 | 689 | 690 | 691 | 692 | 693 | 694 | N/A |
| C |   | 696 | 697 | 698 | 699 | 700 | 701 | 702 | 703 | 705 | 706 | 695 |
| D |   | 708 | 709 | 710 | 711 | 712 | 713 | 714 | 715 | 721 | 722 | 707 |
| E |   | 725 | N/A | 727 | 728 | 772 | 773 | 774 | 775 | 776 | 777 | 723 |
| F |   | 779 | 780 | 788 | 789 | 790 | 791 | 793 | 794 | 797 | 798 | 778 |
| G |   | 800 | 801 | 802 | 803 | 804 | 805 | 806 | 807 | 810 | 815 | 799 |
| H |   | 821 | 822 | 824 | 825 | 827 | 828 |   |   |   |   | 820 |

Plate 2

|   | 1 | 2 | 3 | 4 | 5 | 6 | 7 | 8 | 9 | 10 | 11 | 12 |
|---|---|---|---|---|---|---|---|---|---|----|----|----|
| A |   | 829 | 830 | 831 | 832 | 833 | 834 | 835 | 836 | 837 | 838 | 839 |
| B |   | 840 | 841 | 842 | 852 | 856 | 857 | 858 | 860 | 861 | 862 | 863 |
| C |   | 864 | 865 | 867 | 870 | 871 | 872 | 873 | 874 | 876 | 877 | 878 |
| D |   | 879 | 899 | 900 | 901 |   |   |   |   |   |   |   |
| E |   |   |   |   |   | 684 | 685 | 726 |   |   |   |   |

Viability (% control)   Experiments in duplicate. Average values

A2058 melanoma cells

Screening at 1uM

Plate 1

|   | 1 | 2 | 3 | 4 | 5 | 6 | 7 | 8 | 9 | 10 | 11 | 12 |
|---|---|---|---|---|---|---|---|---|---|----|----|----|
| A |   | 88.35843 | 91.43231 | 87.04242 | 92.18758 | 98.29633 | 59.09972 | 52.95813 | 97.41098 | 101.1937 | 89.84194 | N/A |
| B |   | N/A | 89.52085 | 78.40188 | 67.00355 | 65.8331 | 84.22768 | 87.3476 | 77.63277 | 98.13872 | 90.22959 | 97.4591 |
| C |   | 324.1278 | 80.92431 | 87.99761 | 99.90405 | 79.40542 | 72.85955 | 89.77842 | 92.8016 | 98.51805 | 85.21014 | 85.40522 |
| D |   | 100.3093 | 101.7749 | 101.7749 | 93.23477 | 91.30115 | 74.17964 | 80.88763 | 97.91816 | 100.9842 | 85.57897 | 83.39252 |
| E |   | 101.3407 | 100.1401 | 100.1401 | 86.61777 | 82.01843 | 31.71640 | 81.15 | 74.84214 | 85.16961 | 102.0949 | 104.594 |
| F |   | 96.70805 | 80.68664 | 80.68664 | 87.67393 | 79.69553 | 84.10758 | 90.49861 | 104.3786 | 93.41461 | 89.40927 | 102.079 |
| G |   | 6.680378 | 68.10574 | 68.10574 | 87.29068 | 100.9436 | 81.50738 | 96.10249 | 92.99091 | 70.98163 | 112.0351 | 102.7658 |
| H |   | 131.1791 | 122.0006 | 122.0006 | 104.2433 | 114.1353 | 91.5735 |   |   |   |   |   |

Fig. 3C-2

Plate 2

Screening at 1uM

| | 1 | 2 | 3 | 4 | 5 | 6 | 7 | 8 | 9 | 10 | 11 | 12 |
|---|---|---|---|---|---|---|---|---|---|---|---|---|
| A | | 118.5997 | 98.48044 | 93.63974 | 107.6042 | 127.7493 | 111.0807 | 122.4908 | 904.96055 | 127.3627 | 100.3901 | 115.5855 |
| B | | 102.3827 | 101.9016 | 105.8567 | 73.14132 | 85.89765 | 89.44492 | 66.17994 | 110.0465 | 107.8027 | 124.5699 | 103.7343 |
| C | | 75.80026 | 45.92618 | 121.9402 | 93.38197 | 104.0069 | | 82.6583 | 81.80104 | 73.43844 | 108.539 | 98.10464 | 90.15446 |
| D | | 81.04517 | 99.53317 | | 72.4222 | 92.94602 | | | | | | |
| E | | | | | | 89.20019 | 67.5187 | 66.75836 | | | | |

Plate 1

Screening at 10 uM

| | 1 | 2 | 3 | 4 | 5 | 6 | 7 | 8 | 9 | 10 | 11 | 12 |
|---|---|---|---|---|---|---|---|---|---|---|---|---|
| A | | 16.02012 | 12.73029 | | 11.16067 | 11.33048 | 110.915 | 13.14014 | 44.24351 | 12.33998 | 12.12032 | 9.450048 | N/A |
| B | | N/A | 5.430093 | 76.44092 | 44.9132 | 6.010218 | 77.50445 | 73.49084 | 6.509991 | 113.4161 | 42.79676 | 6.059971 |
| C | | | 13.13 | 9.080193 | 43.80525 | 28.12184 | 58.46262 | 45.32229 | 58.84168 | 9.424984 | 62.76822 | 25.62291 | 8.29017 |
| D | | 6.94934 | 96.07729 | 85.65742 | 101.71636 | 86.84429 | 80.12272 | 77.37658 | 91.00318 | 109.9262 | 95.304 | 98.53225 |
| E | | 104.8222 | N/A | 96.94412 | 103.7571 | 97.79702 | 7.94003 | 66.74849 | 4.949847 | 55.35682 | 67.71184 | 113.2024 |
| F | | 68.68071 | 17.90092 | 3.299774 | 2.729972 | 94.26974 | 51.82121 | 45.9073 | 88.58804 | 76.74993 | 47.62265 | 75.50995 |
| G | | 1.529919 | 1.843854 | 11.55968 | 8.69081 | 2.589916 | 0.789850 | 54.26540 | 52.41241 | 1.17977 | 110.5611 | 6.180499 |
| H | | 127.6589 | | 104.569 | 75.0715 | 5.160305 | 129.7723 | 99.72708 | | | | |

Plate 2

Screening at 10 uM

| | 1 | 2 | 3 | 4 | 5 | 6 | 7 | 8 | 9 | 10 | 11 | 12 |
|---|---|---|---|---|---|---|---|---|---|---|---|---|
| A | | 311.2098 | 40.22961 | 110.4153 | 45.79844 | 140.3228 | 12.479 | 91.04297 | 117.9941 | 87.64766 | 24.94995 | 128.0615 |
| B | | 14.96514 | 124.4214 | 5.31063 | 90.34445 | 65.87641 | 98.17947 | 43.80089 | 64.61177 | 4.020276 | 119.0742 | 99.58717 |
| C | | 11.17757 | 88.53353 | 118.5082 | 59.59415 | 16.02175 | 72.75021 | 9.545077 | 85.57718 | 16.9334 | 34.21015 | 54.05516 |
| D | | 66.47964 | 19.8576 | 70.9325 | 25.00492 | | | | | | | |
| E | | | | | 3.539411 | 0.387974 | 96.67116 | | | | | |

DU145 prostate cancer cells

Plate 1

Screening at 1uM

| | 1 | 2 | 3 | 4 | 5 | 6 | 7 | 8 | 9 | 10 | 11 | 12 |

Fig. 3D-1

Plates 1 and 2 (Continued)

Plate 2

|   | 2 | 3 | 4 | 5 | 6 | 7 | 8 | 9 | 10 | 11 | 12 |
|---|---|---|---|---|---|---|---|---|---|---|---|
| A | 95.0613 | 75.75217 | 75.486 | 66.67103 | 93.94902 | 92.98946 | 61.4773 | 39.02978 | 30.77101 | 65.50596 | N/A |
| B | N/A | 88.4496 | 82.07437 | 70.15761 | 65.1752 | 75.77169 | 88.0806 | 68.36954 | 85.29573 | 94.16994 | 71.81307 |
| C | 94.08632 | 80.44842 | 87.00608 | 65.26131 | 80.78203 | 78.66321 | 82.24124 | 93.0157 | 107.1259 | 88.60445 | 76.09281 |
| D | 103.6629 | 82.35437 | 92.63091 | 96.94317 | 90.39376 | 60.68062 | 27.75127 | 87.52658 | 95.53168 | 87.97815 | 90.25236 |
| E | 93.26774 | N/A | 100.9836 | 32.74256 | 74.15171 | 33.39326 | 82.73932 | 62.51525 | 89.6963 | 82.26282 | 84.40452 |
| F | 83.34943 | 88.91602 | 71.14073 | 61.59372 | 66.56214 | 43.69338 | 90.00222 | 103.9539 | 83.95609 | 86.72492 | 85.76019 |
| G | 22.94215 | 20.33075 | 69.87211 | 51.34107 | 41.88077 | 25.4166 | 72.68248 | 65.8001 | 34.1575 | 87.80908 | 85.64171 |
| H | 106.0975 | 98.2019 | 96.444 | 76.12725 | 96.55637 | 96.38161 | | | | | |

Screening at 1uM

Plate 1

|   | 2 | 3 | 4 | 5 | 6 | 7 | 8 | 9 | 10 | 11 | 12 |
|---|---|---|---|---|---|---|---|---|---|---|---|
| A | 99.89807 | 85.26611 | 82.00349 | 85.69451 | 83.56299 | 80.23598 | 67.16028 | 90.71365 | 96.59821 | 98.5385 | 101.9186 |
| B | 80.98516 | 96.42705 | 97.25315 | 91.08959 | 83.31563 | 57.29797 | 70.83403 | 81.18009 | 87.39917 | 90.12853 | 94.39482 |
| C | 99.08506 | 106.7401 | 92.89354 | 77.82916 | 85.10975 | 73.53896 | 30.57758 | 70.66598 | 108.9878 | 85.32202 | 98.555102 |
| D | 104.6937 | 80.42934 | 98.1236 | 91.21587 | 29.95814 | 72.57924 | 84.17607 | | | | |
| E | | | | | | | | | | | |

Screening at 10 uM

Plate 1

|   | 2 | 3 | 4 | 5 | 6 | 7 | 8 | 9 | 10 | 11 | 12 |
|---|---|---|---|---|---|---|---|---|---|---|---|
| A | 29.50305 | 16.16279 | 14.67102 | 22.76732 | 86.53152 | 21.73158 | 45.38619 | 16.23466 | 28.51283 | 15.21776 | N/A |
| B | N/A | 35.31386 | 103.0122 | 92.08517 | 16.79549 | 53.31082 | 100.6022 | 12.91215 | 50.11476 | 47.50128 | 9.991200 |
| C | 60.00854 | 11.88112 | 52.0626 | 6.259289 | 69.86536 | 90.94124 | 68.51759 | 83.51758 | 93.90875 | 89.81454 | 55.72159 |
| D | 21.9085 | 105.2819 | 90.07122 | 94.51374 | 48.52421 | 87.75075 | 77.17072 | 94.29109 | 93.49165 | 102.2364 | 99.46532 |
| E | 71.45404 | N/A | 84.77233 | 83.27552 | 95.79007 | 15.34895 | 64.074 | 7.412092 | 39.87076 | 24.76973 | 77.77141 |
| F | 80.50323 | 26.3285 | 6.657574 | 30.52944 | 21.57247 | 60.91738 | 86.28978 | 50.52002 | 31.55096 | 49.52407 | |
| G | 6.049944 | 6.523242 | 20.49939 | 18.52804 | 4.134774 | 7.610449 | 60.14634 | 64.0498 | 9.936635 | 60.08579 | 42.51063 |
| H | 99.94771 | 95.31558 | 70.54074 | 7.348066 | 84.03351 | 68.53362 | | | | | |

Screening at 10 uM

Plate 2

|   | 2 | 3 | 4 | 5 | 6 | 7 | 8 | 9 | 10 | 11 | 12 |
|---|---|---|---|---|---|---|---|---|---|---|---|
| A | 85.07255 | 51.79257 | 89.92554 | 47.55502 | 86.72006 | 50.65453 | 88.9951 | 91.42456 | 91.9645 | 30.80185 | 108.9757 |
| B | 92.76406 | 69.91768 | 12.4468 | 66.82785 | 56.75241 | 67.51795 | 94.15886 | 26.65315 | 5.90608 | 84.32968 | 83.86559 |
| C | 18.63518 | 77.66723 | 54.09667 | 56.67396 | 19.23103 | 64.0783 | 10.54079 | 69.57196 | 39.37066 | 19.54377 | 26.53191 |
| D | 73.32063 | 23.58263 | 54.51698 | 25.76142 | 13.01556 | 16.76795 | 94.10569 | | | | |
| E | | | | | | | | | | | |

Fig. 3D-2

T315I mutant KCL-22 CML cells

Plate 1

Screening at 200 uM

|   | 1 | 2 | 3 | 4 | 5 | 6 | 7 | 8 | 9 | 10 | 11 | 12 |
|---|---|---|---|---|---|---|---|---|---|----|----|----|
| A |   | 105.9276 | 109.8636 | 103.2686 | 109.2477 | 99.983 | 103.6379 | 98.40186 | 101.0059 | 97.12685 | N/A |
| B |   | N/A | 95.48407 | 87.89703 | 104.949 | 88.93332 | 102.4332 | 90.238 | 102.6838 | 90.55063 | 101.9951 |
| C |   | 103.7102 | 102.776 | 90.03106 | 97.25165 | 87.22076 | 96.59454 | 90.85015 | 93.81327 | 92.09103 | 95.51209 |
| D |   | 97.78475 | 94.90591 | 88.61648 | 98.00912 | 93.52904 | 92.80417 | 93.91821 | 95.56099 | 91.3626 | 99.6193 |
| E |   | 90.97699 | N/A | 89.27818 | 89.60113 | 97.57104 | 92.16794 | 82.55033 | 99.42726 | 109.5685 | 101.3288 |
| F |   | 95.21715 | 104.2069 | 85.43891 | 89.42743 | 83.48387 | 78.5 | 97.10495 | 84.42421 | 90.95051 | 89.54968 | 98.90513 |
| G |   | 94.37003 | 90.74879 | 87.25451 | 87.89417 | 91.34426 | 88.02202 | 80.6257 | 84.42421 | 78.59255 | 89.59757 | 96.86245 |
| H |   | 100.0248 | 98.8165 | 92.49192 | 95.57729 | 89.69893 |   |   |   |   |   |

Plate 2

Screening at 200 uM

|   | 1 | 2 | 3 | 4 | 5 | 6 | 7 | 8 | 9 | 10 | 11 | 12 |
|---|---|---|---|---|---|---|---|---|---|----|----|----|
| A |   | 115.4991 | 115.0205 | 104.576 | 111.5555 | 105.4217 | 125.9855 | 105.6511 | 118.8671 | 97.41535 | 122.9184 |
| B |   | 105.5312 | 110.5005 | 98.3256 | 104.576 | 107.7513 | 87.5793 | 108.8457 | 89.58718 | 112.3706 | 97.37817 | 107.5746 |
| C |   | 112.8194 | 107.2483 | 109.5095 | 54.49987 | 111.431 | 81.11594 | 114.2096 | 88.57399 | 113.5781 | 96.29559 | 120.5917 |
| D |   | 100.3972 | 112.5683 | 117.223 | 97.4861 | 106.2807 | 75.56779 | 101.6075 |   |   |   |
| E |   |   |   |   |   |   |   |   |   |   |   |

Plate 1

Screening at 1 uM

|   | 1 | 2 | 3 | 4 | 5 | 6 | 7 | 8 | 9 | 10 | 11 | 12 |
|---|---|---|---|---|---|---|---|---|---|----|----|----|
| A |   | 86.30852 | 90.72935 | 80.89651 | 80.34169 | 90.14374 | 79.69148 | 91.42719 | 36.05513 | 39.37703 | 63.70442 | N/A |
| B |   | N/A | 82.65204 | 80.79627 | 87.86013 | 73.58272 | 71.25861 | 86.83715 | 70.27364 | 98.59375 | 91.53557 | 88.38298 |
| C |   | 87.15652 | 94.73196 | 80.5566 | 75.55777 | 86.62506 | 75.63189 | 85.77229 | 78.09049 | 86.30852 | 93.55872 | 85.20189 |
| D |   | 90.10187 | 94.01891 | 85.06117 | 80.03568 | 81.87431 | 79.32071 | 86.61846 | 78.62479 | 85.71329 | 92.16882 | 94.49421 |
| E |   | 95.71875 | N/A | 86.54242 | 81.45417 | 95.00763 | 48.39368 | 78.17606 | 68.00514 | 102.6153 | 94.4943 | 96.8048 |
| F |   | 97.05544 | 103.49 | 67.2123 | 64.20804 | 55.89069 | 52.30365 | 95.95649 | 86.75918 | 90.08027 | 82.54934 | 93.66142 |

Fig. 3E-1

Plates 1 and 2 (Continued)

Plate 2

Screening at 1uM

|   | 1 | 2 | 3 | 4 | 5 | 6 | 7 | 8 | 9 | 10 | 11 | 12 |
|---|---|---|---|---|---|---|---|---|---|----|----|----|
| G |   | 32.06407 | 31.39097 | 70.07969 | 67.83978 | 28.84304 | 28.62436 | 35.41822 | 33.91041 | 28.68904 | 94.20709 | 95.03997 |
| H |   | 101.0884 | 103.0584 | 102.0924 | 87.69852 | 104.7792 | 100.8717 |   |   |   |   |   |
| A |   | 102.6706 | 108.9594 | 111.6827 | 97.67206 | 95.22087 | 102.1797 | 99.01488 | 105.3413 | 102.2032 | 88.91788 | 110.6574 |
| B |   | 98.72339 | 100.0335 | 93.29414 | 94.55408 | 85.69367 | 80.94626 | 81.3308 | 86.61253 | 84.2352 | 94.53561 | 110.0844 |
| C |   | 104.7307 | 87.51397 | 97.65526 | 89.23635 | 85.99689 | 77.65992 | 71.38889 | 94.95282 | 98.98646 | 99.5493 | 111.0746 |
| D |   | 103.681 | 105.5255 | 109.5374 | 90.31941 |   |   |   |   |   |   |   |
| E |   |   |   |   |   | 31.28508 | 88.46727 | 88.01241 |   |   |   |   |

LY-5 lymphoma cells

Plate 1

Screening at 200 uM

|   | 1 | 2 | 3 | 4 | 5 | 6 | 7 | 8 | 9 | 10 | 11 | 12 |
|---|---|---|---|---|---|---|---|---|---|----|----|----|
| A |   | 115.2004 | 95.9372 | 86.07171 | 95.0991 | 102.4167 | 88.15267 | 105.8051 | 39.51863 | 29.48284 | 19.8627 | N/A |
| B |   | N/A | 76.33175 | 75.42938 | 95.61072 | 80.93319 | 64.82364 | 102.8175 | 112.594 | 85.43443 | 99.3591 | 81.34673 |
| C |   | 94.51557 | 71.51094 | 85.9381 | 86.24385 | 94.12834 | 77.54798 | 85.7027 | 111.5554 | 87.17396 | 50.55237 | 109.9719 |
| D |   | 64.56544 | 80.14517 | 29.75406 | 23.74440 | 91.94452 | 83.18328 | 102.4543 | 112.0993 | 94.3875 | 75.18605 | 104.461 |
| E |   | 98.12113 | N/A | 104.432 | 78.08402 | 90.45524 | 61.80452 | 114.5255 | 71.62374 | 95.20301 | 82.54767 | 101.8101 |
| F |   | 104.4382 | 97.37489 | 75.9271 | 65.32731 | 77.03636 | 41.89543 | 96.87838 | 119.6009 | 108.4745 | 77.14823 | 99.38667 |
| G |   | 34.7067 | 26.72695 | 70.7113 | 73.42954 | 12.92316 | 14.5489 | 82.67271 | 106.174 | 45.85375 | 82.12557 | 75.7846 |
| H |   | 115.0877 | 107.7775 | 127.0706 | 88.46919 | 112.5039 | 99.69842 |   |   |   |   |   |

Plate 2

Screening at 200 uM

|   | 1 | 2 | 3 | 4 | 5 | 6 | 7 | 8 | 9 | 10 | 11 | 12 |
|---|---|---|---|---|---|---|---|---|---|----|----|----|
| A |   | 67.52985 | 81.41577 | 89.97288 | 117.5297 | 76.56994 | 75.57556 | 74.56903 | 88.85525 | 79.59657 | 105.301 | 89.46706 |
| B |   | 68.66579 | 77.92868 | 70.95868 | 103.0587 | 72.70776 | 43.63066 | 57.93852 | 72.46176 | 69.75266 | 82.15828 | 62.11766 |
| C |   | 49.51242 | 67.59633 | 69.17508 | 76.20038 | 56.14362 | 67.45715 | 38.40903 | 53.72809 | 67.75725 | 76.95013 | 60.55621 |
| D |   | 64.69586 | 77.07537 | 85.70808 | 89.53447 |   |   |   |   |   |   |   |
| E |   |   |   |   |   | 11.40705 | 46.94553 | 71.31398 |   |   |   |   |

Fig. 3E-2

Plate 1

Screening at 1 uM

| | 1 | 2 | 3 | 4 | 5 | 6 | 7 | 8 | 9 | 10 | 11 | 12 |
|---|---|---|---|---|---|---|---|---|---|---|---|---|
| A | | 26.59865 | 51.31537 | 23.92292 | 20.00094 | 67.80845 | 14.21346 | 81.61159 | 15.02304 | 23.20566 | 12.06799 | 31.25178 |
| B | | 12.93438 | 5.603658 | 9.155025 | 56.35595 | 54.62267 | 37.42543 | 67.70656 | 0.877114 | 81.9624 | 64.69084 | 8.490358 |
| C | | 69.65171 | 20.00363 | 77.17072 | 42.42812 | 72.99735 | 31.23915 | 51.44241 | 55.99375 | 61.19291 | 32.02001 | 28.262 |
| D | | 12.94069 | 57.29339 | 90.21636 | 65.07196 | 75.2383 | 18.41287 | 59.77733 | 55.22283 | 57.01954 | 70.78481 | 60.77076 |
| E | | 67.04936 | 53.26121 | 88.40703 | 65.06361 | 58.48562 | 14.20715 | 94.6951 | 5.6655 | 70.34056 | 42.61828 | 56.67314 |
| F | | 57.9459 | 50.04261 | 4.77701 | 5.3262 | 6.884607 | 3.250166 | 81.726 | 43.26058 | 70.48654 | 45.54493 | 74.83509 |
| G | | 5.338815 | 1.663665 | 3.36732 | 1.111606 | 4.34530 | 0.993435 | 3.51374 | 2.98662 | 5.087950 | 62.15478 | 80.16444 |
| H | | 96.38371 | 82.54506 | 77.86668 | 12.93438 | 85.33835 | 91.74005 | | | | | |

Plate 2

Screening at 1 uM

| | 1 | 2 | 3 | 4 | 5 | 6 | 7 | 8 | 9 | 10 | 11 | 12 |
|---|---|---|---|---|---|---|---|---|---|---|---|---|
| A | | 110.194 | 74.19073 | 77.45349 | 138.3524 | 77.45349 | 102.9545 | 98.11205 | 88.5215 | 78.51136 | 113.6517 | 52.2345 | 92.2135 |
| B | | 100.4307 | 86.8127 | 105.3103 | 62.00788 | 6.845559 | 9.294933 | 64.67587 | 66.57805 | 24.03128 | 78.48147 | 23.5142 |
| C | | 12.80762 | 72.78396 | 54.04855 | 57.3976 | 4.95828 | 57.26824 | 8.31635 | 64.20889 | 65.98755 | 59.69239 | 45.32793 |
| D | | 88.80018 | 60.14449 | 82.06691 | 54.0631 | | | | | | | |
| E | | | | | | 7.108799 | 4.535889 | 77.88513 | | | | |

KCL-22 CML

Plate 1

Screening at 1 uM

| | 1 | 2 | 3 | 4 | 5 | 6 | 7 | 8 | 9 | 10 | 11 | 12 |
|---|---|---|---|---|---|---|---|---|---|---|---|---|
| A | | 89.65893 | 91.18 | 88.07034 | 73.02538 | 98.89817 | 93.80656 | 95.45028 | 33.07314 | 28.19983 | 79.69437 | N/A |
| B | | N/A | 86.58928 | 90.5326 | 89.08955 | 56.84201 | 59.88443 | 78.74237 | 84.39182 | 112.3421 | 106.7307 | 85.76524 |
| C | | 91.33428 | 81.62683 | 67.83423 | 69.24483 | 68.41757 | 66.36671 | 76.54961 | 83.68166 | 91.02045 | 108.5904 | 82.93273 |
| D | | 99.26041 | 93.01062 | 90.08877 | 81.10785 | 98.75742 | 80.84915 | 75.41387 | 71.74826 | 109.3177 | 100.6699 | 98.13104 |
| E | | 78.37896 | N/A | 81.56328 | 68.48589 | 80.24667 | 16.72874 | 67.81737 | 35.84695 | 114.4194 | 97.77541 | 88.99279 |
| F | | 83.18984 | 79.01108 | 42.7087 | 40.63989 | 41.66309 | 30.58691 | 82.53769 | 102.7371 | 91.80369 | 89.10434 | 93.11881 |
| G | | 9.066101 | 8.659459 | 42.61192 | 30.00693 | 13.04576 | 9.423967 | 21.64146 | 19.08183 | 11.81344 | 93.79675 | 91.87251 |
| H | | 91.50146 | 96.09688 | 93.61776 | 67.20319 | 107.2985 | 91.86149 | | | | | |

Plate 2

Screening at 1 uM

Fig. 3F-1

Plates 1 and 2 (Continued)

PaCa2 pancreatic cancer

Plate 1

| | 1 | 2 | 3 | 4 | 5 | 6 | 7 | 8 | 9 | 10 | 11 | 12 |
|---|---|---|---|---|---|---|---|---|---|---|---|---|
| A | | 115.7557 | 96.26447 | 111.5425 | 112.6063 | 107.6271 | 98.74885 | | 108.646 | 101.8912 | 107.3199 | 102.2253 |
| B | | 98.16148 | 86.73014 | 91.99557 | 104.5449 | 94.82891 | 93.25889 | | 73.45708 | 96.16843 | 78.55624 | 99.57612 |
| C | | 86.98190 | 74.1644 | 89.70584 | 87.106 | 96.88172 | 101.0699 | | 64.40213 | 89.95471 | 55.02958 | 81.80322 |
| D | | 79.99778 | 92.01499 | 74.64927 | 54.60438 | | | | | | 83.98345 | |
| E | | | | | | 40.97002 | 99.60443 | 91.45152 | | | | |

Screening at 1 uM

Plate 1

| | 1 | 2 | 3 | 4 | 5 | 6 | 7 | 8 | 9 | 10 | 11 | 12 |
|---|---|---|---|---|---|---|---|---|---|---|---|---|
| A | | 84.44664 | 56.55595 | 64.90975 | 51.88949 | 85.60979 | 67.32576 | 38.34278 | 81.54602 | 11.22697 | 73.97854 | N/A |
| B | | N/A | 81.77695 | 89.56312 | 72.88076 | 47.07529 | 56.99021 | 108.9743 | 63.89532 | 85.17139 | 82.72472 | 53.50805 |
| C | | 89.15405 | 96.53587 | 80.51137 | 54.45167 | 77.56236 | 59.30182 | 100.6891 | 78.1447 | 89.4259 | 89.81107 | 83.64488 |
| D | | 86.78306 | 82.51897 | 87.96748 | 95.4456 | 98.3829 | 68.58762 | 82.69223 | 98.25771 | 78.99445 | 86.79221 | 102.8806 |
| E | | 94.52628 | N/A | 83.60008 | 84.10874 | 100.2036 | 25.19852 | 88.38058 | 32.85878 | 74.99149 | 62.77167 | 78.89599 |
| F | | 95.45031 | 79.21123 | 33.45980 | 29.083308 | 42.07226 | 22.01363 | 79.07229 | 81.85063 | 86.97507 | 68.86305 | 96.43457 |
| G | | 0 | 0 | 59.14450 | 32.75061 | 2.314046 | 1.524955 | 22.96273 | 35.66977 | 12.52743 | 107.5105 | 94.38594 |
| H | | 116.7925 | 87.75873 | 84.44612 | 54.18354 | 92.1081 | 84.08284 | | | | | |

Screening at 1 uM

Plate 2

| | 1 | 2 | 3 | 4 | 5 | 6 | 7 | 8 | 9 | 10 | 11 | 12 |
|---|---|---|---|---|---|---|---|---|---|---|---|---|
| A | | 101.5405 | 70.47879 | 78.84986 | 78.66511 | 92.97684 | 80.95759 | 105.402 | 77.76997 | 85.47489 | 58.01717 |
| B | | 80.20557 | 88.74857 | 51.81109 | 70.16193 | 50.242 | 28.486165 | 74.06714 | 62.26125 | 74.9396 | 98.00416 | 73.66901 |
| C | | 76.45589 | 86.88785 | 84.85558 | 82.8103 | 70.26542 | 81.05907 | 54.65098 | 32.62035 | 81.15535 | 70.56987 | 85.90164 |
| D | | 87.27056 | 76.69942 | 81.28025 | 84.35077 | | | | | | | |
| E | | | | | | 27.48154 | 70.06766 | 81.43378 | | | | |

Fig. 3F-2

SKOV3 ovarian cancer

Plate 1

Screening at 1 uM

|   | 1 | 2 | 3 | 4 | 5 | 6 | 7 | 8 | 9 | 10 | 11 | 12 |
|---|---|---|---|---|---|---|---|---|---|---|---|---|
| A |   | 98.383 | 89.70606 | 88.29594 | 83.11765 | 96.98576 | 97.47448 | 80.37818 | 98.64003 | 49.95475 | 88.84225 | N/A |
| B |   | N/A | 99.65142 | 82.18121 | 77.58465 | 85.69726 | 92.12968 | 86.42155 | 70.67695 | 89.21753 | 84.40559 | 91.51216 |
| C |   | 94.05096 | 70.59018 | 67.43483 | 73.53382 | 81.99252 | 72.49649 | 86.82019 | 84.2503 | 88.22204 | 82.94788 | 86.91483 |
| D |   | 95.558 | 89.91547 | 75.98278 | 80.38816 | 76.41622 | 74.5364 | 71.02076 | 77.7578 | 79.54965 | 88.82901 | 104.219 |
| E |   | 78.55038 | N/A | 72.22953 | 85.03251 | 59.4541 | 22.53612 | 64.46528 | 49.115 | 73.86168 | 77.76336 | 81.23142 |
| F |   | 76.70627 | 73.90621 | 60.97667 | 50.58807 | 53.73825 | 31.67569 | 76.93623 | 83.96648 | 81.29224 | 65.43715 | 80.65593 |
| G |   | 13.38158 | 9.083888 | 48.03131 | 40.87534 | 73.39216 | 12.53871 | 19.46158 | 44.53879 | 44.12397 | 84.87271 | 82.87224 |
| H |   | 113.2031 | 90.01161 | 100.0922 | 89.94484 | 88.89678 | 85.398 |   |   |   |   |   |

Plate 2

Screening at 1 uM

|   | 1 | 2 | 3 | 4 | 5 | 6 | 7 | 8 | 9 | 10 | 11 | 12 |
|---|---|---|---|---|---|---|---|---|---|---|---|---|
| A |   | 99.04471 | 105.4643 | 84.21587 | 81.46733 | 91.86091 | 92.4723 | 64.19564 | 72.90791 | 71.2266 | 57.62323 | 100.1146 |
| B |   | 105.3244 | 80.55594 | 82.84295 | 68.01481 | 52.05579 | 84.37142 | 71.37944 | 112.9538 | 92.1665 | 92.62514 | 86.20558 |
| C |   | 91.70806 | 67.86397 | 44.47841 | 64.34849 | 62.4444 | 77.18762 | 70.00382 | 77.03477 | 64.80703 | 72.68514 | 68.01681 |
| D |   | 101.7959 | 55.63622 | 79.17461 | 62.36148 | 27.97096 | 81.00879 | 62.20864 |   |   |   |   |

K562 CML

Plate 1

Screening at 1 uM

|   | 1 | 2 | 3 | 4 | 5 | 6 | 7 | 8 | 9 | 10 | 11 | 12 |
|---|---|---|---|---|---|---|---|---|---|---|---|---|
| A |   | 88.05573 | 87.04023 | 80.39881 | 91.31343 | 99.60713 | 73.04218 | 55.39585 | 31.03491 | 31.6312 | 26.32962 | 70.24068 |
| B |   | 28.60448 | 72.45096 | 85.62107 | 64.57866 | 58.69104 | 67.07124 | 97.49557 | 65.03448 | 80.43203 | 73.05081 | 92.1205 |
| C |   | 80.40865 | 72.50345 | 66.95996 | 55.82541 | 71.60191 | 64.23688 | 96.16513 | 74.8036 | 86.6024 | 70.24199 | 71.0511 |
| D |   | 42.62136 | 80.95226 | 94.85629 | 73.64546 | 97.97739 | 85.06667 | 83.12849 | 95.10417 | 65.3771 | 83.80916 | 88.30361 |
| E |   | 89.73417 | 81.90948 | 73.88025 | 89.70632 | 69.98632 | 11.46074 | 79.68528 | 38.58657 | 62.12097 | 74.99623 | 77.28095 |
| F |   | 81.95049 | 84.20922 | 73.45107 | 56.78431 | 80.15873 | 52.82328 | 81.01545 | 86.6927 | 91.3868 | 56.98457 | 96.2777 |
| G |   | 34.46304 | 25.15191 | 35.32857 | 43.3837 | 36.03927 | 25.82733 | 51.57152 | 45.15124 | 28.95833 | 89.84545 | 71.7367 |
| H |   | 123.59 | 108.3956 | 98.41402 | 95.49847 | 86.5186 | 82.7567 |   |   |   |   |   |

Fig. 3F-3

Plate 2

Screening at 1 uM

| | 1 | 2 | 3 | 4 | 5 | 6 | 7 | 8 | 9 | 10 | 11 | 12 |
|---|---|---|---|---|---|---|---|---|---|---|---|---|
| A | | 105.7896 | 76.32969 | 103.1071 | 75.73998 | 95.00905 | 77.76859 | 94.23111 | 87.62145 | 98.95424 | 72.29086 | 102.6966 |
| B | | 92.85048 | 87.24491 | 80.20953 | 69.56141 | 71.54607 | 28.92758 | 70.16223 | 79.55029 | 78.03941 | 86.32005 | 97.30219 |
| C | | 95.11693 | 85.49719 | 63.55351 | 81.96161 | 54.09954 | 75.82644 | 16.23008 | 65.40562 | 51.47524 | 59.73524 | 54.30765 |
| D | | 76.29011 | 82.83076 | 80.1714 | 72.87911 | 32.71796 | 76.34371 | 86.26553 | | | | |
| E | | | | | | | | | | | | |

Fig. 4

| IRD No. | ID # | Prostate cancer | | Melanoma | | Pancreatic cancer | | Ovarian cancer | | Leukemia | | | | | | Lymphoma | |
|---|---|---|---|---|---|---|---|---|---|---|---|---|---|---|---|---|---|
| | | DU145 cells Viability (% Control) | | A2058 cells Viability (% Control) | | PaCa2 cells Viability (% Control) | | SKOV3 cells Viability (% Control) | | T315I mutant KCL-22 CML cells Viability (% Control) | | K562 CML cells Viability (% Control) | | KCL-22 CML cells Viability (% Control) | | LY-3 cells Viability (% Control) | |
| [test compound] | | 1µM | 10µM | 1µM | 10µM | 1µM | 10µM | 1µM | 10µM | 1µM | 10µM | 1µM | 10µM | 1µM | 10µM | 200nM | 1µM |
| 9 | 880 | | | | | 39.343 | | | | | | | | | | | |
| 10 | 881 | 38.838 | 16.235 | | | | | | | 36.856 | | 31.635 | | 33.873 | | 39.519 | 15.623 |
| 11 | 882 | 30.777 | 28.513 | | | 11.227 | | 45.985 | | 38.377 | | 31.631 | | 28.280 | | 29.483 | 23.208 |
| 12 | 883 | | | | | | | | | | | 25.329 | | | | 19.823 | 12.868 |
| 13 | 884 | 35.988 | 13.836 | | | 27.291 | | 27.971 | | 31.386 | | 32.718 | | | | 11.807 | 7.389 |
| 58 | 773 | 33.383 | 15.349 | 31.710 | 7.940 | 25.788 | | 22.836 | | 48.394 | | 11.367 | | 18.729 | | 51.664 | 14.287 |
| 61 | 775 | | | | | 32.859 | | 49.115 | | | | 38.587 | | 35.847 | | | |
| 68 | 788 | | | | | 33.460 | | | | | | | | | | | |
| 69 | 789 | | | | | 29.834 | | 50.588 | | | | | | | | | |
| 70 | 790 | | | | | 43.672 | | | | 35.892 | | | | | | | |
| 71 | 791 | 43.630 | 21.572 | | | 22.614 | | 31.878 | | 32.304 | | | | | | 41.895 | 3.250 |
| 79 | 800 | 22.842 | 6.850 | 5.880 | 1.530 | 0 | | 13.382 | | 32.984 | | 34.883 | 9.885 | | | 34.797 | 5.339 |
| 80 | 801 | 28.331 | 6.523 | 3.891 | 1.850 | 0 | | 9.884 | | 31.391 | | 28.152 | 8.619 | | | 28.727 | 1.678 |
| 91 | 802 | | | | | | | 49.031 | | | | | | | | | |
| 92 | 803 | | | | | 32.751 | | 46.878 | | | | | | | | | |

| ID No. | COH No. | Prostate cancer | | Melanoma | | Pancreatic cancer | | Ovarian cancer | | Leukemia | | | | | | Lymphoma | |
|---|---|---|---|---|---|---|---|---|---|---|---|---|---|---|---|---|---|
| | | DU145 cells Viability (% Control) | | A2058 cells Viability (% Control) | | PaCa2 cells Viability (% Control) | | SKOV3 cells Viability (% Control) | | T315I mutant KCL-22 CML cells Viability (% Control) | | K562 CML cells Viability (% Control) | | KCL-22 CML cells Viability (% Control) | | LY-3 cells Viability (% Control) | |
| [test compound] | | 1µM | 10µM | 1µM | 10µM | 1µM | 10µM | 1µM | 10µM | 1µM | 10µM | 1µM | 10µM | 1µM | 10µM | 200nM | 1µM |
| 83 | 804 | 41.881 | 4.135 | | | 2.314 | | | | 28.843 | | 36.639 | | 13.846 | | 12.823 | 4.345 |
| 84 | 805 | 25.416 | 7.618 | | | 1.528 | | 12.531 | | 28.623 | | 25.827 | | 9.424 | | 14.649 | 9.993 |
| 85 | 806 | | | | | 22.953 | | 19.482 | | 35.418 | | | | 21.841 | | | |
| 86 | 807 | | | | | 38.378 | | 44.539 | | 35.378 | | | | 18.882 | | | |
| 87 | 810 | 34.157 | 3.337 | | | 12.527 | | 44.124 | | 28.829 | | 28.869 | | 11.813 | | 46.864 | 5.488 |
| 115 | 857 | | | | | 28.378 | | | | | | 28.828 | | | | 43.531 | 9.295 |
| 134 | 867 | | | | | | | 44.478 | | | | | | | | | |
| 128 | 873 | 30.378 | 10.541 | | | | | | | | | 18.238 | | | | 38.410 | 8.317 |
| 178 | 1222 | 28.269 | 8.520 | 3.493 | 6.501 | 8.693 | 7.234 | 8.345 | 5.130 | 16.772 | 19.147 | | | 19.951 | 15.73y | | |

Fig. 12

| IRD NO. | ID # | Prostate cancer | Melanoma | Pancreatic cancer | Ovarian cancer | Leukemia | | |
|---|---|---|---|---|---|---|---|---|
| | | DU145 cells IC$_{50}$ value (μM) | A2058 cells IC$_{50}$ value (μM) | MIA-PaCa2 cells IC$_{50}$ value (μM) | SKOV3 cells IC$_{50}$ value (μM) | T315I KCL-22 CML cells IC$_{50}$ value (μM) | KCL-22 CML cells IC$_{50}$ value (μM) | MV4-11 AML cells IC$_{50}$ value (μM) |
| IN-10 | 681 | NT | NT | NT | NT | NT | 0.74 | NT |
| IN-11 | 682 | NT | NT | NT | NT | NT | 0.57 | NT |
| IN-13 | 684 | NT | NT | NT | NT | NT | 0.53 | NT |
| IN-70 | 790 | NT | NT | NT | NT | NT | 0.70 | NT |
| IN-79 | 800 | NT | NT | 0.77 | 0.72 | NT | NT | NT |
| IN-80 | 801 | NT | NT | 0.82 | 0.66 | NT | NT | NT |
| IN-83 | 804 | NT | NT | NT | NT | NT | 0.31 | NT |
| IN-84 | 805 | NT | NT | 0.37 | 1.0 | NT | 0.23 | NT |
| IN-87 | 810 | NT | NT | 0.35 | 0.87 | NT | 0.43 | NT |
| IN-176 | 1222 | 0.34 | 0.32 | 0.63 | 0.37 | 0.17 | 0.18 | 0.043 |

*NT means Not Tested

Fig. 13

| IRD No. | ID No. | Kinases IC$_{50}$ values (nM) | | | | | | | | | | | | | |
|---|---|---|---|---|---|---|---|---|---|---|---|---|---|---|---|
| | | ABL1 | ABL1 (T315I mutant) | Aurora A | CDK2 / cyclin A | c-Src | FGR | FLT 3 | FYN | GSK3 β | HCK | LYN | JAK1 | JAK2 | TYK2 |
| 10 | 681 | >10,000 | >10,000 | >10,000 | NT | 3,497.00 | NT | NT | NT | NT | NT | NT | NT | >10,000 | NT |
| 11 | 682 | 5,621.00 | >10,000 | >10,000 | NT | 302.10 | NT | NT | NT | NT | NT | NT | NT | >10,000 | NT |
| 13 | 684 | 8,341.00 | >10,000 | >10,000 | NT | 185.70 | NT | NT | NT | NT | NT | NT | NT | >10,000 | NT |
| 61 | 775 | 15.70 | 96.00 | 815.00 | NT | 0.66 | NT | NT | NT | NT | NT | NT | NT | 1190.00 | NT |
| 70 | 790 | 468.10 | >10,000 | 329.45 | NT | 1.69 | NT | NT | NT | NT | NT | NT | NT | >10,000 | NT |
| 71 | 791 | 3340.00 | >10,000 | >10,000 | NT | 3.90 | NT | NT | NT | NT | NT | NT | NT | >10,000 | NT |
| 79 | 800 | 7.16 | 177.90 | 9.70 | NT | 0.22 | NT | NT | NT | NT | NT | NT | NT | 550.70 | NT |
| 80 | 801 | 10.20 | 194.00 | 41.50 | NT | 0.61 | NT | NT | NT | NT | NT | NT | NT | 589.00 | NT |
| 83 | 804 | 106.50 | 4,564.00 | 79.03 | NT | 4.86 | NT | NT | NT | NT | NT | NT | NT | 7,463.00 | NT |
| 84 | 805 | 66.90 | 5,940.00 | 175.00 | NT | 2.24 | NT | NT | NT | NT | NT | NT | NT | 4,410.00 | NT |
| 85 | 806 | 34.08 | 5,160.00 | 14.90 | NT | 0.83 | NT | NT | NT | NT | NT | NT | NT | >10,000 | NT |
| 86 | 807 | 42.00 | >10,000 | 110.00 | NT | 1.39 | NT | NT | NT | NT | NT | NT | NT | >10,000 | NT |
| 87 | 810 | 0.87 | 9.40 | 7.08 | NT | 0.06 | NT | NT | NT | NT | NT | NT | NT | 223.80 | NT |
| 176 | 1222 | 577 | >10,000 | 2,760 | 1,070 | 124 | 4.2 | 57 | 420 | 378 | 147 | 216 | >10,000 | >10,000 | 1,290 |

*NT means Not Tested

INDIRUBIN DERIVATIVES, AND USES THEREOF

CROSS REFERENCE TO RELATED APPLICATIONS

This application is a continuation of U.S. patent application Ser. No. 13/826,204, filed Mar. 14, 2013, issuing as U.S. Pat. No. 10,435,367 on Oct. 8, 2019, which is a continuation-in-part of U.S. patent application Ser. No. 13/758,921, filed Feb. 4, 2013, issued as U.S. Pat. No. 9,512,076 on Dec. 6, 2016, which claims the benefit of U.S. Provisional Patent Application No. 61/594,934, filed Feb. 3, 2012; and U.S. Provisional Patent Application No. 61/676,267, filed Jul. 26, 2012, all of which are incorporated herein by reference as if fully set forth herein.

BACKGROUND OF THE INVENTION

Signal Transducer and Activator of Transcription (STAT) proteins have essential functions in normal cytokine signaling and are frequently constitutively activated in human tumor cells (Yu and Jove, 2004). STATs have key roles in regulating cell proliferation, survival, angiogenesis and immune function (Parsons and Parsons, 2004; Yu et al., 2009). One of seven different STAT family members, Stat5, is constitutively activated by non-receptor tyrosine kinases (Herrington et al., 2000; Huang et al., 2002; Klejman et al., 2002; Nieborowska-Skorska et al., 1999; Yu and Jove, 2004). Bcr-Abl, an oncogenic non-receptor tyrosine kinase activated in chronic myelogenous leukemia (CML), induces persistent tyrosyl phosphorylation of Stat5 (Bromberg et al., 1999; Nelson et al., 2006; Quintas-Cardama et al., 2006; Shah et al., 2004; Yu and Jove, 2004). Bcr-Abl kinase cooperates with Src family kinases (SFKs) to activate Stat5 in CML cell transformation (Klejman et al., 2002; Wilson et al., 2002). SFKs, also non-receptor tyrosine kinases, phosphorylate critical cellular substrates such STAT family members, including Stat5, thereby regulating oncogenic signaling pathways (Bromann et al., 2004; Parsons and Parsons, 2004; Silva, 2004; Yu and Jove, 2004). In particular, the SFKs, Lyn and Hck, have been shown to cooperate with Bcr-Abl to activate Stat5 signaling in CML cells (Klejman et al., 2002; Lionberger et al., 2000; Wilson et al., 2002).

STAT signaling is currently being investigated as a new molecular target pathway for human cancer treatment (Yu and Jove, 2004; Yu et al., 2009). In Stat5 signaling, two phosphorylated Stat monomers dimeize through reciprocal phosphotyrosyl-SH2 domain interactions (Bromberg et al., 1999; Yu and Jove, 2004). The phosphorylated Stat5 dimers then translocate to the nucleus and bind to the promoters of specific Stat5 responsive genes (Bromberg et al., 1999; Nelson et al., 2006; Yu and Jove, 2004). Persistent activation of Stat5 has a critical role in cell growth and survival in human hematopoietic malignancies (Carlesso et al., 1996; Yu and Jove, 2004). Constitutively-activated Stat5 upregulates the expression of anti-apoptotic genes encoding Mcl-1 and Bcl-xL proteins in human CML cells (Gesbert and Griffin, 2000; Horita et al., 2000; Nelson et al., 2006; Yu and Jove, 2004). In contrast, blockade of Stat5 signaling down-regulates these down-stream target genes of Stat5, associated with induction of apoptosis in CML cells (Horita et al., 2000; Shah et al., 2004; Yu and Jove, 2004).

Indirubin is the major active anti-tumor ingredient of a traditional Chinese herbal medicine, Danggui Longhui Wan, which is a mixture of 11 herbal ingredients and used for CML treatment (Xiao et al., 2002). Indirubin derivatives (IRDs) were shown to inhibit CDK1/cyclin B, CDK2/cyclinA, CDK2/cycling E, GSK 3β and CDK5/p25, leading to cell growth inhibition in human cancer cells (Hoessel et al., 1999; Marko et al., 2001; Vougogiannopoulou et al., 2008). IRDs also inhibit phosphorylation of Stat5 in acute myeloid leukemia cells (Zhou et al., 2009). Recently, it has been demonstrated that IRDs blocked constitutive Stat3 signaling in epithelial tumor cells such as breast and prostate cancer (Nam et al., 2005a).

Previously, clinical studies indicated that indirubin is a promising anticancer therapeutic agent for CML treatment, showing low toxicity (Eisenbrand et al., 2004). However, the mechanism of action of IRDs in CML remains largely unknown. There is a need to develop more IRDs and uses thereof in treating cancer (e.g. CML).

SUMMARY OF THE INVENTION

One aspect of the present disclosure relates to an indirubin derivative (IRD) comprising a structure of Structure A:

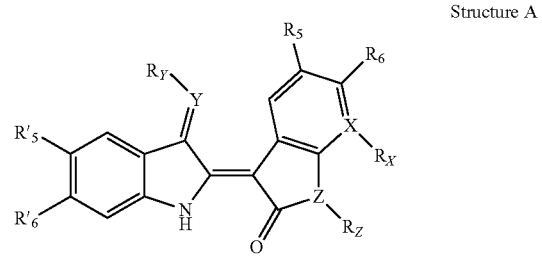

and the pharmaceutically acceptable solvates, salts and stereoisomers thereof, including mixtures thereof in all ratios.

Another aspect of the present disclosure relates to a pharmaceutical composition comprising an IRD disclosed herein.

Another aspect of the present disclosure relates to a method of preparing an IRD disclosed herein.

Another aspect of the invention relates to a method of treating a cancer or tumor in a subject comprising administering to the subject a therapeutically effective amount of one or more indirubin derivatives disclosed herein, or a pharmaceutical composition thereof.

Another aspect of the invention relates to a method of treating a condition regulated by a protein kinase in a subject comprising administering to the subject a therapeutically effective amount of one or more indirubin derivatives disclosed herein, or a pharmaceutical composition thereof.

BRIEF DESCRIPTION OF THE DRAWINGS

FIGS. 1A-1Y: Numbering and structures of IRDs of a first synthetic library.

FIGS. 2A-2M: Numbering and structures of IRDs of a second synthetic library.

FIGS. 3A-1-F-3: Effects of examples of the compounds disclosed herein on A2058 melanoma cells, DU145 prostate cancer cells, T315I mutant KCL-22 CML cells, LY-3 lymphoma cells, KCL-22 CML cells, PaCa2 pancreatic cancer cells, SKOV3 ovarian cancer cells, and K562 CML cells. (A)-(B): plate 3; (C-F): plates 1 and 2.

FIG. 4: Effects of IRD Nos. 9, 10, 11, 12, 13, 59, 61, 68, 69, 70, 71, 79, 80, 81, 82, 83, 84, 85, 86, 87, 115, 124, 128, and 176 on A2058 melanoma cells, DU145 prostate cancer cells, T315I mutant KCL-22 CML cells, LY-3 lymphoma cells, KCL-22 CML cells, PaCa2 pancreatic cancer cells, SKOV3 ovarian cancer cells, and/or K562 CML cells.

FIG. 12: $IC_{50}$ values of IRD Nos. 10, 11, 13, 70, 71, 79, 80, 83, 84, 87 and 176 on DU145 prostate cancer cells, A2058 melanoma cells, MIA-PaCa2 pancreatic cancer cells, SKOV3 ovarian cancer cells, T315I KCL-22 CML cells, and/or KCL022 CML cells.

FIG. 13: Effects of IRD Nos. 10, 11, 13, 70, 79, 80, 83, 84, 85, 86, 87 and 176 on protein kinases ABL1, ABL1 (T315I mutant), Aurora A, CDK2/cyclin A, c-Src, FGR, FLT3, FYN, GSK3β, HCK, LYN, JAK2, and/or TYK2.

DETAILED DESCRIPTION OF THE INVENTION

Figure 1Y:
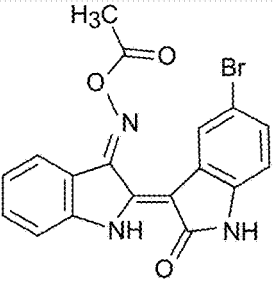
Figure 2M:
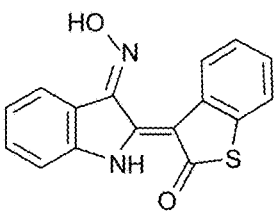

One aspect of the present disclosure relates to an indirubin derivative (IRD) comprising a structure of Structure A:

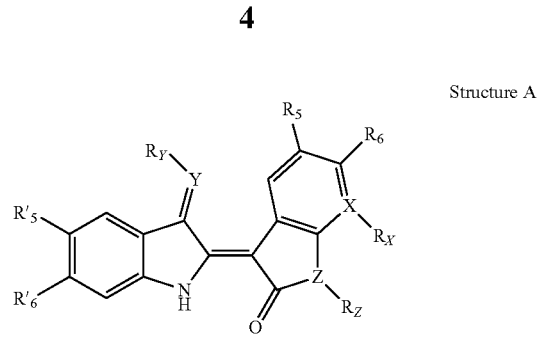

Structure A and the pharmaceutically acceptable solvates, salts and stereoisomers thereof, including mixtures thereof in all ratios, wherein:

X is C or N, more preferably C;

$R_X$ is selected from the group consisting of nothing, H, halogen, and haloalkyl;

more preferably selected from the group consisting of H and halogen;

$R_6$ is selected from the group consisting of H, halogen, substituted and unsubstituted alkylamino, and substituted and unsubstituted alkoxy; more preferably H or Br;

$R_5$ is selected from the group consisting of H, halogen, nitro, amino, substituted and unsubstituted alkylamino, and substituted and unsubstituted alkyl; more preferably H;

Y is N or O; more preferably N;

when Y is N, $R_Y$ is selected from the group consisting of nothing, H, hydroxy, alkoxy, haloalkoxy, substituted and unsubstituted —O—C(=O)—N(R')R", substituted and unsubstituted —O—C(=O)—$R_0$, and —O—R—R'; more preferable $R_Y$ is —O—CH$_2$—CH$_2$—Br, —O—C(=O)—CH$_3$, OH, —O—CH$_2$—CH$_2$—N(CH$_3$)$_2$, —O—CH$_2$—CH$_2$—N(CH$_2$—CH$_3$)$_2$, —O—CH$_3$, —O—C(=O)—NEt$_2$, —OCH$_2$—CH$_2$—OH, —O—CH$_2$—CH(OH)—CH$_2$—OH,

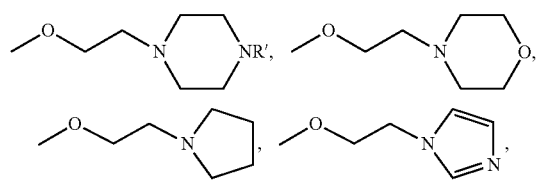

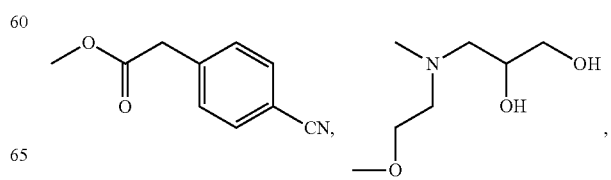

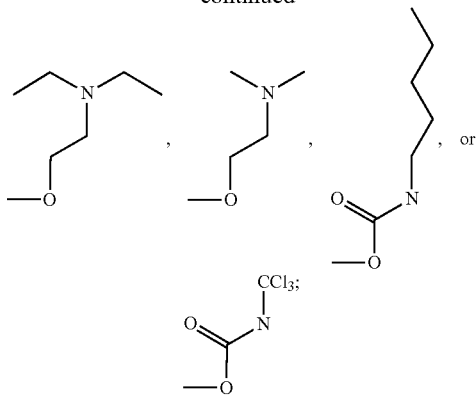

when Y is O, $R_Y$ is nothing;

$R'_5$ is selected from the group consisting of H, alkoxy, nitro, —CN, —C(=O)—O—$R_0$, —C(=O)—OH, —C(=O)H, heteroaryl, —C=N—OH and —R—OH; more preferably H, nitro or —C(=O)—O—$R_0$;

$R'_6$ is selected from the group consisting of H, halogen, alkyl and —C(=O)—O—$R_0$; more preferably H;

Z is N or S; more preferably N;

$R_z$ is selected from the group consisting of H, O, —C(=O)—$R_0$, and $R_0$; more preferably H or $R_0$;

each R is independently nothing or substituted or unsubstituted alkylenyl; more preferably —CH$_2$— or —(CH$_2$)$_2$—;

each $R_0$ is independently substituted or unsubstituted alkyl; more preferably methyl, ethyl, or —(CH$_2$)—CH$_2$(OH)—CH$_2$OH; and each R' and R" are independently selected from the group consisting of H, substituted and unsubstituted alkyl, substituted and unsubstituted alkoxy, substituted and unsubstituted alkylamino, substituted and unsubstituted haloalkyl, substituted and unsubstituted heterocyclyl, substituted and unsubstituted aryl and substituted and unsubstituted heteroaryl; more preferably alkyl is methyl, ethyl, propyl, butyl, or pentyl, haloalkyl is floroalkyl (e.g. trifloroalkyl), chloroalkyl (e.g. trichloroalkyl), or bromoalkyl, heterocyclyl is morpholinyl, pyrrolidinyl or piperazinyl, optionally substituted with —CH$_3$, —OCH$_2$—CH$_2$—OH, —OCH$_2$—CH$_2$—OCH$_2$—CH$_2$OH, or —OCH$_2$—CH$_2$—OCH$_3$, and aryl is phenyl or imidazolyl, optionally substituted with —CN, or —C(=O)-Me.

In one embodiment, the preferred IRDs are IRDs described supra with the proviso that the preferred IRDs are not indirubin, indirubin-3'-oxime, indirubin-3'-acetoxime, indirubin-3'-methoxime, IRD Nos. 2, 58, 59, 61, 64-72, 74, 77-88, 90, 129-132, 142-144, 146, 161, a compound having the structure of Structure A, wherein:

$R_5$ and $R'_5$ are H; Z is N; X is C; $R_X$ is H; wherein:
when Y is O; $R_Z$ is H; and $R_6$ and $R'_6$ are H or Br;
when Y is O; $R_Z$ is CH$_3$; $R_6$ is H or Br; and $R'_6$ is H;
when Y is N; $R_Y$ is —OH; $R_Z$ is H; and $R_6$ and $R'_6$ are H or Br;
when Y is N; $R_Y$ is —OH; $R_Z$ is CH$_3$; $R_6$ is H or Br; and $R'_6$ is H;
when Y is N; $R_Y$ is —OCH$_3$ or —OC(=O)—CH$_3$; $R_Z$ and $R'_6$ are H; and $R_6$ is Br; or
when Y is N; $R_6$ is Br; $R_Z$ and $R'_6$ are H; $R_Y$ is 2-bromoethyl, 2-hydroxyethoxy, 2,3,-dihydroxypropoxy, N,N-diethylcarbamyloxy, 2-dimethylaminoethoxy, 2-diethylaminoethoxy, 2-(pyrrolidin-1'-yl) ethyl, 2-(morpholin-1'-yl)ethoxy, 2-[N,N-(2-hydroxyethyl)amino]ethoxy, 2-[N-methyl, N-(2',3'-dihydroxypropyl)amino]ethoxy, 2-(piperazin-1'-yl) ethoxy, 2-(4'-methyl-piperazin-1'-yl)ethoxy, 2-{4'-[2"-(2"'-hydroxyethoxy)-ethyl] piperazin-1'-yl}ethoxy, 2-[4'-(2"-hydroxyethyl)-piperazin-1-yl] ethoxy, or 2-[4'-(2"-methoxyethyl)-piperazin-1-yl] ethoxy; or a compound having the structure of Structure A, wherein:
$R'_5$ is Br; Z is N; X is C; $R_X$ is H; $R_Z$, $R'_6$, and $R_6$ are H; $R_5$ is H or Br; and Y is O; or
$R'_5$ is H; Z is N; X is C; $R_X$ is H; wherein:
when $R_5$, $R_Z$, $R'_6$, and $R_6$ are H; Y is O or N; and $R_Y$ is nothing, OH, OCH$_3$ or OAc;
when $R_Z$, $R'_6$, and $R_6$ are H; $R_5$ is Cl, Br, nitro, or methyl; and Y is O;
when $R_Z$, $R'_6$, and $R_6$ are H; $R_5$ is I; Y is O or N; and $R_Y$ is nothing, or OH;
when $R_Z$, and $R'_6$ are H; $R_5$ is amino; $R_6$ is H or Br; Y is O or N; and $R_Y$ is nothing, or OH;
when $R_5$, and $R_Z$ are H; $R'_6$ is H or Br; $R_6$ is Br; Y is O or N; and $R_Y$ is nothing, or OH;
when $R_5$, $R'_6$, and $R_Z$ are H; $R_6$ is Br; Y is O or N; and $R_Y$ is nothing, OH, OCH$_3$ or OAc;
when $R_5$, and $R'_6$ are H; $R_Z$ is CH$_3$; $R_6$ is Br or H; Y is O or N; and $R_Y$ is nothing, or OH;
when $R_5$, $R'_6$, and $R_Z$ are H; $R_6$ is I, Br, Cl, F, or —CH$_2$=CH$_2$; $R_6$ is Cl; Y is O or N; and $R_Y$ is nothing, OH, OCH$_3$ or OAc;
when $R'_6$, and $R_Z$ are H; $R_5$ is nitro or CH$_3$; $R_6$ is Br; Y is O or N; and $R_Y$ is nothing, OH, OCH$_3$ or OAc; or
when $R'_6$, and $R_Z$ are H; $R_5$ and $R_6$ are Cl; Y is O or N; and $R_Y$ is nothing, OH, OCH$_3$ or OAc.

In another embodiment, $R_6$ of the compounds described above is not a halogen.

In another embodiment, $R_6$ of the compounds described above is not Br.

In another embodiment, $R_Z$ of the compounds described above is not an alkyl.

As used herein, the term "solvate" refers to a complex of variable stoichiometry formed by a solute (in this invention, a compound disclosed herein comprising a structure of Structure A or a salt thereof) and a solvent. Such solvents for the purpose of the invention may not interfere with the biological activity of the solute. Examples of suitable solvents include, but are not limited to, water, aqueous solution (e.g. buffer), methanol, ethanol and acetic acid. Preferably, the solvent used is a pharmaceutically acceptable solvent. Examples of suitable pharmaceutically acceptable solvents include, without limitation, water, aqueous solution (e.g. buffer), ethanol and acetic acid. Most preferably, the solvent used is water or aqueous solution (e.g. buffer). Examples for suitable solvates are the mono- or dihydrates or alcoholates of the compounds according to the invention.

The invention includes the pharmaceutically acceptable salts of all the compounds described herein. The salts are formed with acids and bases, which include but are not limited to the following examples. Examples of suitable inorganic acids include, but are not limited to: hydrochloric acid, hydrofluoric acid, hydrobromic acid, hydroiodic acid, sulfuric acid and boric acid. Examples of suitable organic acids include but are not limited to: acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid. Examples of suitable inorganic bases include, but are not limited to: ammonia, hydroxyethylamine and hydrazine. Examples of suitable organic bases include, but are not limited to, methylamine, ethylamine, trimethylamine, triethylamine, ethylenediamine, hydroxyethylamine, morpholine, piperazine and guanidine. The invention further provides for the hydrates and polymorphs of all of the compounds described herein.

Certain of the compounds described herein may contain one or more chiral atoms, or may otherwise be capable of existing as two or more stereoisomers, which are usually enantiomers and/or diastereomers. Accordingly, the compounds of this invention include mixtures of stereoisomers, mixtures of enantiomers, as well as purified stereoisomers, purified enantiomers, or stereoisomerically enriched mixtures, enantiomerically enriched mixtures. Also included within the scope of the invention are the individual isomers of the compounds represented by Structure A above as well as any wholly or partially equilibrated mixtures thereof. The invention also covers the individual isomers of the compounds represented by Structure A above as mixtures with isomers thereof in which one or more chiral centers are inverted. Also, it is understood that all tautomers and mixtures of tautomers of the compounds of Structure A above are included within the scope of the compounds of Structure A and preferably the structures corresponding thereto.

Racemates obtained can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as camphorsulfonic acid. Also advantageous is enantiomer resolution with the aid of a column filled with an optically active resolving agent. The diastereomer resolution can also be carried out by standard purification processes, such as, for example, chromatography or fractional crystallization.

It is also possible to obtain optically active compounds comprising Structure I by the methods described above by using starting materials which are already optically active.

As used herein, the term "alkyl" refers to a straight or branched chain hydrocarbon having 1, 2, 3, 4, 5, 6, 7, 8, 9, 10, 11, 12, 13, 14, 15, 16, 17, 18, 19 or 20 carbon atoms, optionally including one or more unsaturated carbon-carbon bonds (e.g. C=C or C—C triple bond).

As used herein, the term "alkoxy" refers to an alkyl group wherein one or more hydrogen and/or carbon atoms are substituted with one or more oxygen atoms and/or hydroxyl groups.

As used herein, the term "alkylamino" refers to an alkyl group wherein one or more hydrogen and/or carbon atoms are substituted with one or more nitrogen atoms and/or amino groups.

As used herein, the term "haloalkyl" refers to an alkyl group wherein one or more hydrogen and/or carbon atoms are substituted with one or more the same or different halogen atoms.

As used herein, the term "cycloalkyl" refers to a non-aromatic cyclic hydrocarbon ring having from three to seven carbon atoms and which optionally includes an alkyl linker through which it may be attached, preferably a $C_1$-$C_6$ alkyl linker as defined above. Such a ring may be optionally fused to one or more cycloalkyl ring(s), aryl ring(s), and/or heteroaryl ring(s). Exemplary "cycloalkyl" groups include, but are not limited to, cyclopropyl, cyclobutyl, cyclopentyl, cyclohexyl and cycloheptyl.

As used herein, the term "heterocyclic" or the term "heterocyclyl" refers to a 3, 4, 5, 6, 7, 8, 9, 10, 11 or 12-membered cycloalkyl ring containing one or more heteroatomic substitutions on the ring selected from S, O or N. Such a ring may be optionally fused to one or more cycloalkyl ring(s), heterocyclic ring(s), aryl ring(s), and/or heteroaryl ring(s). Examples of "heterocyclic" moieties include, but are not limited to, tetrahydrofuran, pyran, 1,4-dioxane, 1,3-dioxane, pyrrolidine, piperidine, morpholine, tetrahydrothiopyran, tetrahydrothiophene, piperazine, and the like.

As used herein, the term "aryl" refers to an aromatic cyclic hydrocarbon ring (such as phenyl ring) and which optionally includes an alkyl linker through which it may be attached, preferably a C1-C6 alkyl linker as defined above. Such a ring may be optionally fused to one or more other aryl ring(s). Examples of "aryl" groups include, but are not limited to, phenyl, 2-naphthyl, 1-naphthyl, biphenyl, imidazolyl as well as substituted derivatives thereof.

As used herein, the term "heteroaryl" refers to an aromatic cyclic hydrocarbon ring containing one or more heteroatomic substitutions on the ring selected from S, O or N, and which optionally includes an alkyl linker through which it may be attached, preferably a C1-C6 alkyl linker as defined above. Such a ring may be optionally fused to one or more other aryl ring(s) and/or heteroaryl ring(s). Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzopyrrolyl, benzothiophenyl, indolyl, indazolyl, and substituted derivatives thereof.

As used herein, the term "halogen" or "halo" refers to fluorine (F), chlorine (Cl), bromine (Br) or iodine (I).

Unless otherwise specified, all substituents intend to include optionally substituted substituents, i.e. further substituted or not. For example, an alkyl group may be an unsubstituted alkyl group, or a substituted alkyl group as defined supra.

As used herein, the term "substituted" refers to substitution(s) on one or more atoms, wherein each atom may be substituted with one or more substituents described above. Further examples of substitutions include, without limitation, halogen, alkyl, alkoxy, alkylamino, haloalkyl, —CN, and alkylcarbonyl.

In another embodiment, the compounds described above are IRDs having structures shown in FIGS. 1A-Y and 2A-M, and the pharmaceutically acceptable solvates, salts and stereoisomers thereof, including mixtures thereof in all ratios. As used herein, a compound having a structure shown in FIGS. 1A-Y and 2A-M can be referred to by either the IRD No. or the ID No. thereof. For example, a compound having the following structure:

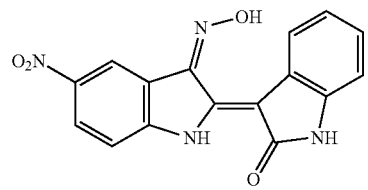 [SMILES: O=C1Nc2ccccc2/C1=C1/Nc2ccc([N+](=O)[O-])cc2/C1=N/O]

can be referred to as IRD NO. 3, IRD #3, ID #673, ID No. 673, #673 or 673.

Several IRDs disclosed in FIGS. 1A-Y and 2A-M are hydrochloride salts. One example of the pharmaceutically acceptable derivatives are the non-salt form of the IRD hydrochloride salts, e.g. the IRDs wherein the amino groups are all or partially neutral. A person of ordinary skill in the art would understand that other suitable inorganic salts and organic salts of the IRDs disclosed herein can also be prepared and used to achieve substantially similar effects. Examples of suitable inorganic acids for the suitable inorganic salts include, but are not limited to, hydrochloric acid, hydrofluoric acid, hydrobromic acid, hydroiodic acid, sulfuric acid and boric acid. Examples of suitable organic acids for the suitable organic salts include, but are not limited to, but are not limited to, acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid.

II. Pharmaceutical Compositions

Another aspect of the invention relates to a pharmaceutical composition comprising a therapeutically effective amount of one or more IRDs described herein.

In certain embodiments, the pharmaceutical composition further comprises a pharmaceutically acceptable carrier.

As used herein, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance a normal physiological function. An effective amount of a pharmaceutical composition to be employed therapeutically will depend, for example, upon the therapeutic context and objectives. One person of ordinary skill in the art will appreciate that the appropriate dosage levels for treatment will thus vary depending, in part, upon the characteristics of the molecule administered (including activity, pharmacokinetics, pharmacodynamics, and bioavailability thereof), the indication for which the one or more IRDs are being used, the nature of the pharmaceutically acceptable carrier or carriers in the formulation (if a pharmaceutical composition disclosed herein is used), the route of administration, and the size (body weight, body surface or organ size) and physiological condition (age, sex, disease type and stage, general physical condition, responsiveness to a given dosage, and type of medication) of the subject or cells treated. Accordingly, one person of ordinary skill in the clinical and pharmacological arts may titer the dosage and modify the route of administration to obtain the optimal therapeutic effect through routine experimentation, namely by monitoring a cell's or subject's response to administration of the one or more IRDs disclosed herein or the pharmaceutical composition thereof and adjusting the dosage accordingly. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg. For additional guidance, see Remington: The Science and Practice of Pharmacy, 21st Edition, Univ. of Sciences in Philadelphia (USIP), Lippincott Williams & Wilkins, Philadelphia, Pa., 2005, which is hereby incorporated by reference as if fully set forth herein for additional guidance for determining a therapeutically effective amount.

A "pharmaceutically acceptable carrier is a pharmaceutically-acceptable material, composition or vehicle, such as a liquid or solid filler, diluent, excipient, solvent or encapsulating material, involved in carrying or transporting an active ingredient from one location, body fluid, tissue, organ (interior or exterior), or portion of the body, to another location, body fluid, tissue, organ, or portion of the body. Each carrier is "pharmaceutically acceptable" in the sense of being compatible with the other ingredients, e.g., the one or more IRDs described herein or other ingredients, of the formulation and suitable for use in contact with the tissue or organ of a biological subject without excessive toxicity, irritation, allergic response, immunogenicity, or other problems or complications, commensurate with a reasonable benefit/risk ratio.

Pharmaceutically acceptable carriers are well known in the art and include, without limitation, (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of the one or more IRDs disclosed herein in these pharmaceutical compositions can vary widely, and will be selected primarily based on fluid volumes, viscosities, body weight and the like in accordance with the particular mode of administration selected and the biological subject's needs. For example, the concentration of the one or more IRDs disclosed herein can be 0.0001% to 100%, 0.001% to 50%, 0.01% to 30%, 0.1% to 20%, 1% to 10% wt.

A suitable pharmaceutically acceptable carrier may be selected taking into account the chosen mode of administration, and the physical and chemical properties of the compounds.

One person of ordinary skill in the art will recognize that a pharmaceutical composition containing one or more IRDs disclosed herein can be administered to a subject by various routes including, without limitation, orally or parenterally, such as intravenously. The composition can be administered by injection or by intubation.

In one embodiment, the pharmaceutical carrier may be a liquid and the pharmaceutical composition would be in the form of a solution. In another embodiment, the pharmaceutically acceptable carrier is a solid and the pharmaceutical composition is in the form of a powder, tablet, pill, or capsules.

In another embodiment, the pharmaceutical carrier is a gel and the pharmaceutical composition is in the form of a suppository or cream.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient (e.g. the one or more IRDs disclosed herein). In tablets, the active-ingredient is mixed with a carrier having the necessary compression properties in suitable proportions and compacted in the shape and size desired. The powders and tablets preferably contain up to 99% of the active ingredient (e.g. the one or more IRDs disclosed herein). Suitable solid carriers include, for example, calcium phosphate, magnesium stearate, talc, sugars, lactose, dextrin, starch, gelatin, cellulose, polyvinylpyrrolidine, low melting waxes and ion exchange resins.

Besides containing an effective amount of one or more IRDs described herein the pharmaceutical composition may also include suitable diluents, preservatives, solubilizers, emulsifiers, adjuvant and/or carriers.

The pharmaceutical composition can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

Additional pharmaceutical compositions will be evident to those of ordinary skill in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those of ordinary skill in the art. See for example, PCT/US93/00829[48] that describes controlled release of porous polymeric microparticles for the techniques of the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides,[49-50] copolymers of L-glutamic acid and gamma ethyl-L-glutamate,[51] poly (2-hydroxyethylmethacrylate),[52-53] ethylene vinyl acetate[52-53] or poly-D(−)-3-hydroxybutyric acid.[54] Sustained-release compositions also include liposomes, which can be prepared by any of several methods known in the art.[55-58]

In one embodiment, the present invention is directed to kits for producing a single-dose administration unit. The kits may each contain both a first container having dried components and a second container having a formulation comprising a pharmaceutically acceptable carrier (e.g. an aqueous formulation). Also included within the scope of this invention are kits containing single and multi-chambered pre-filled syringes (e.g., liquid syringes and lyosyringes).

III. Methods of Preparing Certain Indirubin Derivatives (IRD-N).

Another aspect of the invention relates to a method of preparing an IRD disclosed herein, wherein $R_Y$ is —$OR_N$—$R_N'$, $R_N$ is a substituted or unsubstituted alkylenyl and $R_N'$ is a substituted or unsubstituted alkylamio group (IRD-N), the method comprises the following steps:

A1) providing a compound having Structure A, wherein $R_Y$ is —$OR_N$—W (IRD-W), wherein W is Br, Cl or I; and A2) coupling IRD-W of Step A1) with $R_N'$—H at a reaction temperature in the presence of microwave until the conversion to IRD-N is substantially complete (i.e. about 75% or more).

In one embodiment, the reaction temperature is about 70° C. to about 90° C. In another embodiment, the reaction temperature is about 85° C.

Any equipment that can provide a microwave source can be used in this method. In one embodiment, the reaction is carried out in a microwave. Examples of suitable microwaves include, without limitation, CEM Single-Mode microwave.

In one embodiment, the power of the microwave is about 70 W to about 200 W. In another embodiment, the power of the microwave is about 100 W.

An organic solvent can be used to dissolve IRD-W in Step A1) before the coupling reaction (Step A2). Examples of such organic solvents include, without limitation, anhydrous acetonitrile.

In certain embodiments, the method further includes the following steps after Step A2):

A3) removing the solvent of the reaction obtained from Step A2) to obtain IRD-N;

A4) triturating IRD-N; and

A5) filtering IRD-N and washing IRD-N with water and cyclohexane to afford IRD-N.

Examples of the appropriate amines include, without limitation, diethylamine, piperazine, N-methylpiperazine, 3-methylamine-1,2-propanediol, 1-(2-hydroxyethyl)piperazine and 1-[2-(2-hydroxyethoxy)-ethyl]piperazine.

IV. Methods of Using One or More Indirubin Derivatives in Cancer Treatments.

Another aspect of the invention relates to a method of treating a cancer or tumor in a subject comprising administering to the subject one or more IRDs disclosed herein, or a pharmaceutical composition thereof.

Optimal dosages to be administered may be determined by those of ordinary skill in the art, and will vary with the particular one or more IRDs in use, the strength of the preparation, the mode of administration, and the advancement of the disease condition. Additional factors depending on the particular subject being treated, includes, without limitation, subject age, weight, gender, diet, time of administration, time and frequency of administration, reaction sensitivities, and response to therapy. Administration of the pharmaceutical composition may be effected continuously or intermittently. In any treatment regimen, the pharmaceutical composition may be administered to a patient either singly or in a cocktail containing two or more indirubin derivatives, other therapeutic agents, compositions, or the like, including, but not limited to, tolerance-inducing agents, potentiators and side-effect relieving agents. All of these agents are administered in generally-accepted efficacious dose ranges such as those disclosed in the Physician's Desk Reference, 41st Ed., Publisher Edward R. Barnhart, N. J. (1987). In certain embodiments, an appropriate dosage level will generally be about 0.001 to 50 mg per kg subject body weight per day that can be administered in single or multiple doses. Preferably, the dosage level will be about 0.005 to about 25 mg/kg, per day; more preferably about 0.01 to about 10 mg/kg per day; and even more preferably about 0.05 to about 1 mg/kg per day.

The frequency of dosing will depend upon the pharmacokinetic parameters of the therapeutic agents in the pharmaceutical composition (e.g. one or more indirubin derivatives disclosed herein) used. Typically, a pharmaceutical composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data. Long-acting pharmaceutical compositions may be administered every 3 to 4 days, every week, or biweekly depending on the half-life and clearance rate of the particular formulation.

In certain embodiments, the one or more IRDs are selected from the group consisting of IRD Nos. 2, 10, 11, 13, 58, 59, 61, 64-72, 74, 77-88, 90, 129-132, 142-144, 146, and 161.

Examples of the cancer or tumor treated in the method include, without limitation, CML, prostate cancer, melanoma, pancreatic cancer, ovarian cancer, leukemia and lymphoma.

In certain embodiments, the cancer treated is CML. The preferred one or more IRDs are selected from the group consisting of IRD Nos. 10, 11, 13, 59, 61, 68~71, 79, 80, and 83~87. In another embodiment, the preferred indirubin derivative is IRD No. 176. In certain embodiments the CML treated is a drug (e.g. imatinib, dasatinib and/or nilotinib) resistant CML (e.g. T315I KCL-22 CML). The preferred one or more IRDs are selected from the group consisting of IRD Nos. 10, 11, 13, 70, 71, 79, 80, and 83~87.

In certain embodiments, the cancer treated in the method is prostate cancer, and the preferred one or more IRDs are selected from the group consisting of IRD Nos. 10-11, 13, 59, 71, 79, 80, 83, 84, 87, 128, 135, 137, 138, 176 and 177. In another embodiment, the preferred indirubin derivative is IRD Nos. 10-11, 13, 59, 71, 79, 80, 83, 84, 87, 128 and 176.

In another embodiment, the cancer treated in the method is melanoma, and the preferred one or more IRDs are selected from the group consisting of IRD Nos. 59, 135, 137, 138, 176 and 177. In another embodiment, the preferred indirubin derivative is IRD Nos. 59 and 176.

In another embodiment, the cancer treated in the method is pancreatic cancer, and the preferred one or more IRDs are selected from the group consisting of IRD Nos. 9, 11, 13, 59, 61, 68-71, 82-87, 115, 135, 137, 138, 176 and 177. In another embodiment, the preferred indirubin derivatives are 9, 11, 13, 59, 61, 68-71, 82-87, 115, and 176. In another embodiment, the preferred indirubin derivatives are IRD Nos. 79, 80, 84, 87 and 176.

In another embodiment, the cancer treated in the method is ovarian cancer, and the preferred one or more IRDs are selected from the group consisting of IRD Nos. 11, 13, 59, 61, 69, 71, 79-82, 84-87, 124, 135, 137, 138, 176 and 177. In another embodiment, the preferred indirubin derivatives are IRD Nos. 11, 13, 59, 61, 69, 71, 79-82, 84-87, 124, and 176. In another embodiment, the preferred indirubin derivatives are IRD Nos. 79, 80, 84, 87 and 176.

In another embodiment, the cancer treated in the method is leukemia, and the preferred one or more IRDs are selected from the group consisting of IRD Nos. 10-13, 59, 61, 70, 71, 79-80, 83-87, 115, 128, and 176. In another embodiment, the preferred indirubin derivatives are IRD Nos. 10-13, 59, 61, 70, 71, 79-80, 83-87, 115, 128, and 176. In another embodiment, the preferred indirubin derivative is IRD No. 176.

In another embodiment, the cancer treated in the method is lymphoma, and the preferred one or more IRDs are selected from the group consisting of IRD Nos. 10-13, 59, 79-80, 83, 84, 87, 115, 128 and 176. In another embodiment, the preferred indirubin derivative is IRD No. 176.

V. Methods of Using Indirubin Derivatives in a Condition Regulated by a Protein Kinase.

Another aspect of the invention relates to a method of treating a condition regulated by one or more protein kinases in a subject comprising administering to the subject a therapeutically effective amount of one or more indirubin derivatives disclosed herein, or a pharmaceutical composition thereof.

In one embodiment, the protein kinase is selected from the group consisting of ABL1, ABL1 (T315I mutant), Aurora A, CDK2/cyclin A, c-Src, FGR, FLT3, FYN, GSK3β, HCK, LYN, JAK2, and TYK2. Stat3 or Stat5 signaling is activated by JAK family, Src family or Bcr-Abl. These kinases have been targeted for human cancer therapy.

In one embodiment, the protein kinase is selected from the group consisting of ABL1, ABL1 (T315I mutant), Aurora A, CDK2/cyclin A, c-Src, FGR, FLT3, FYN, GSK3β, HCK, LYN, JAK2, and TYK2. Stat3 or Stat5 signaling is activated by JAK family, Src family or Bcr-Abl. These kinases have been targeted for human cancer therapy.

In another embodiment, the protein kinase is ABL1, and the preferred one or more indirubin derivatives are selected from the group consisting of IRD Nos. 11, 13, 61, 70, 71, 79, 80, 83~87, and 176. In another embodiment, the one or more indirubin derivatives are selected from the group consisting of IRD Nos. 61, 79, 80, and 84~87.

In another embodiment, the protein kinase is ABL1 (T315I mutant), and the preferred one or more indirubin derivatives are selected from the group consisting of IRD Nos. 61, 79, 80, 83~85 and 87. In another embodiment, the preferred one or more indirubin derivatives are selected from the group consisting of IRD Nos. 61, 79, 80, and 87, more preferably IRD NO. 87.

In another embodiment, the protein kinase is Aurora A, and the preferred one or more indirubin derivatives are selected from the group consisting of IRD Nos. 61, 70, 79, 80, 83~87, and 176. In another embodiment, the preferred one or more indirubin derivatives are selected from the group consisting of IRD Nos. 79, 85, and 87.

In another embodiment, the protein kinase is c-Src, and the preferred one or more indirubin derivatives are selected from the group consisting of IRD Nos. 10, 11, 13, 61, 70, 71, 79, 80, 83~87, and 176. In another embodiment, the preferred one or more indirubin derivatives are selected from the group consisting of IRD Nos. 61, 70, 71, 79, 80, and 83~87.

In another embodiment, the protein kinase is CDK2/cyclin A, FGR, FLT3, FYN, GSK3β, HCK, LYN, or TYK2, and the preferred indirubin derivative is IRD No. 176.

In another embodiment, the protein kinase is JAK2, and the preferred one or more indirubin derivatives are selected from the group consisting of IRD Nos. 61, 79, 80, 83, 84 and 87. In another embodiment, the preferred one or more indirubin derivatives are selected from the group consisting of IRD Nos. 79, 80, and 87.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entireties, as if fully set forth herein.

EXAMPLES

Example 1. IRDs Reduced Cancer Cell Viability

Screening Assays on A2058 Melanoma Cells, DU145 Prostate Cancer Cells, T315I Mutant KCL-22 CML Cells, LY-3 Lymphoma Cells, KCL-22 CML Cells, PaCa2 Pancreatic Cancer Cells, SKOV3 Ovarian Cancer Cells, and K562 CML Cells Imatinib-resistant human KCL-22 CML cells expressing the T315I mutant Bcr-Abl were derived from human KCL-22 CML cell. These cells extensively resisted over 10 µM of imatinib (Yuan, et al., 2010, JBC), and also appeared to resist to dasatinib and nilotinib, which have been approved as the second generation therapy for CML patients. MTS assays were performed for cell viability.

MTS assays were performed for cell viability as described by the supplier (Promega, Madison, Wis.). Each type of cells were seeded in 96-well plates (10000/well), incubated overnight at 37° C. in 5% $CO_2$, and exposed to the tested compounds/composition at 200 nM, 1 µM, or 10 µM for 48 h. Dimethyl sulfoxide (DMSO) was used as the vehicle control. Viable cell numbers were determined by tetrazolium conversion to its formazan dye and absorbance was measured at 490 nm using an automated ELISA plate reader.

Figure 5:
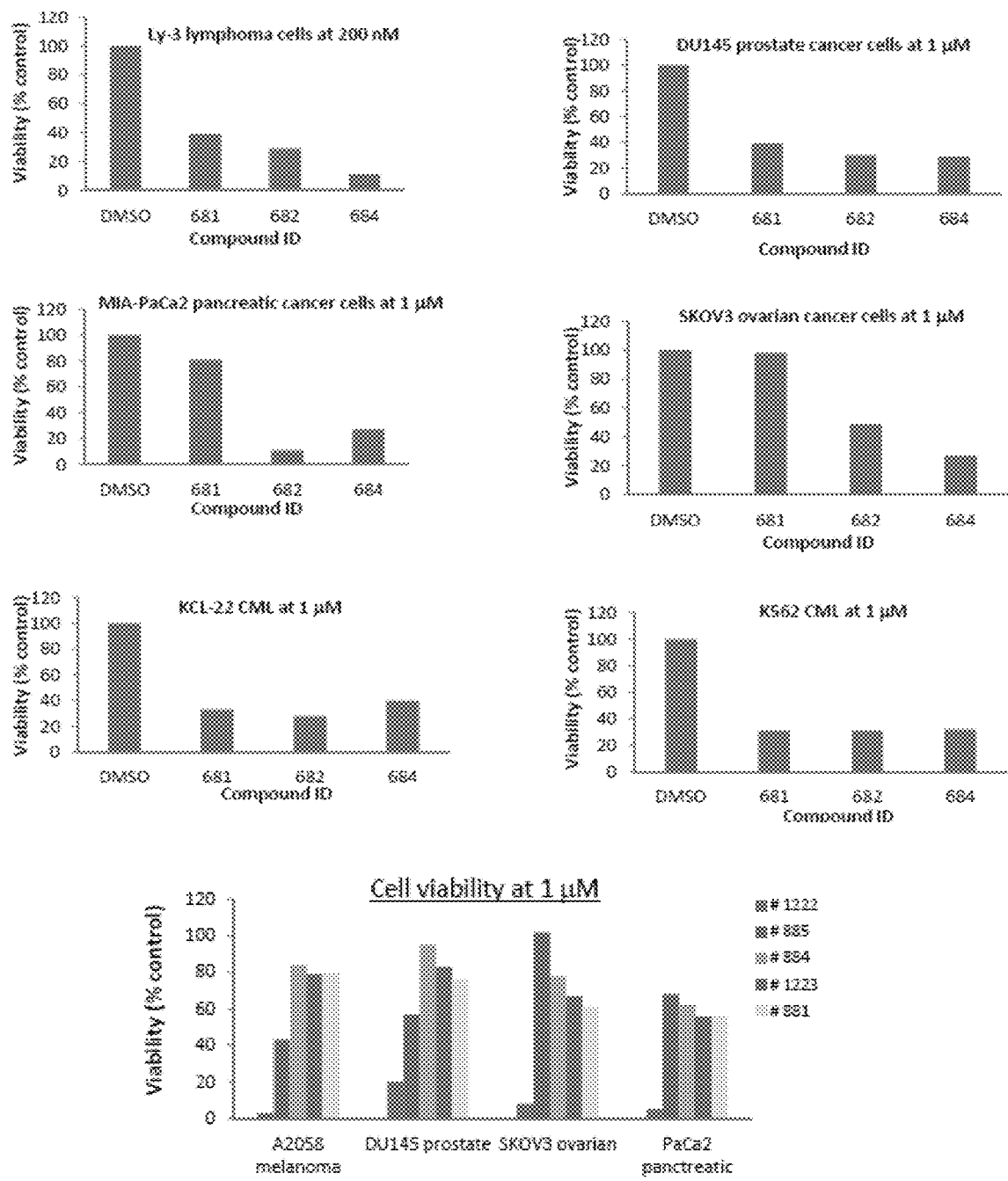
FIG. 5: Effects of IRD Nos. 10, 11, and 13 on LY-3 lymphoma cells (200 nM), DU145 prostate cancer cells (1 μM), MIA-PaCa2 pancreatic cancer cells (1 μM), SKOV3 ovarian cancer cells (1 μM), KCL-22 CML cells (1 μM), and K562 CML cells (1 μM), effects of IRD Nos. 135, 137, 138, 176 and 177 on DU145 prostate cancer cells, A2058 melanoma cells, SKOV3 ovarian cancer cells, and MIA-PaCa2 pancreatic cancer cells.
Figure 6A:
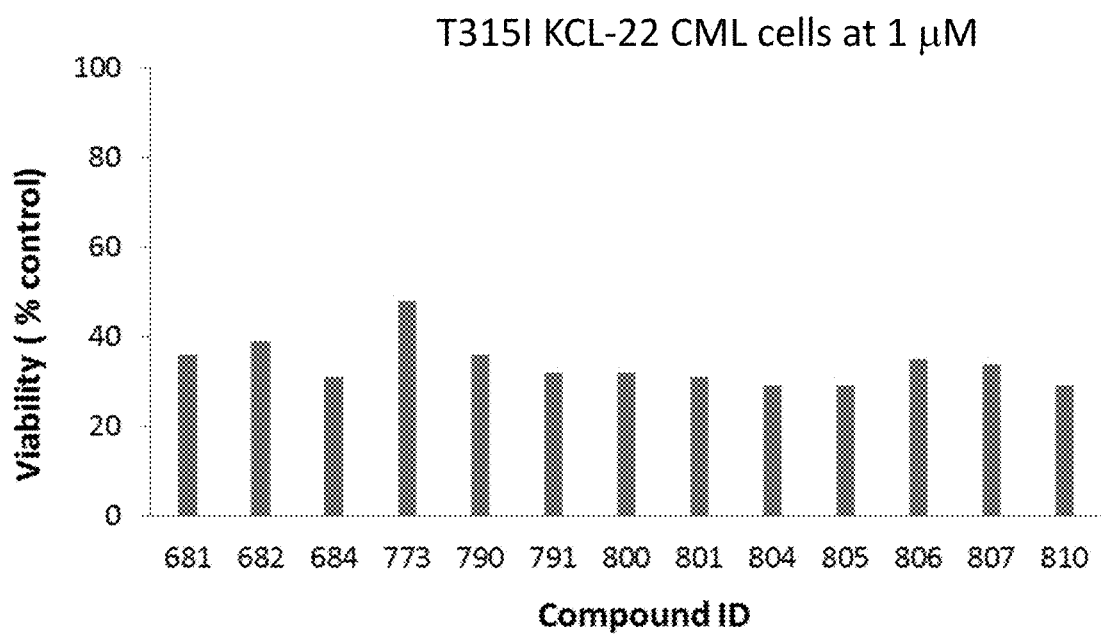
FIGS. 6A-6B—Effects of IRDs on viabilities of cancer cells at 1 μM concentration of the tested IRDs. (A) Effects of IRD Nos. 10, 11, 13, 59, 70~71, 79, 80, and 83~87 on T315I mutant KCL-22 CML cells; and (B) Effects of IRD Nos. 10, 11, 13, 59, 61, 68~71, and 79~87 on KCL-22 CML cells.
Figure 6B:
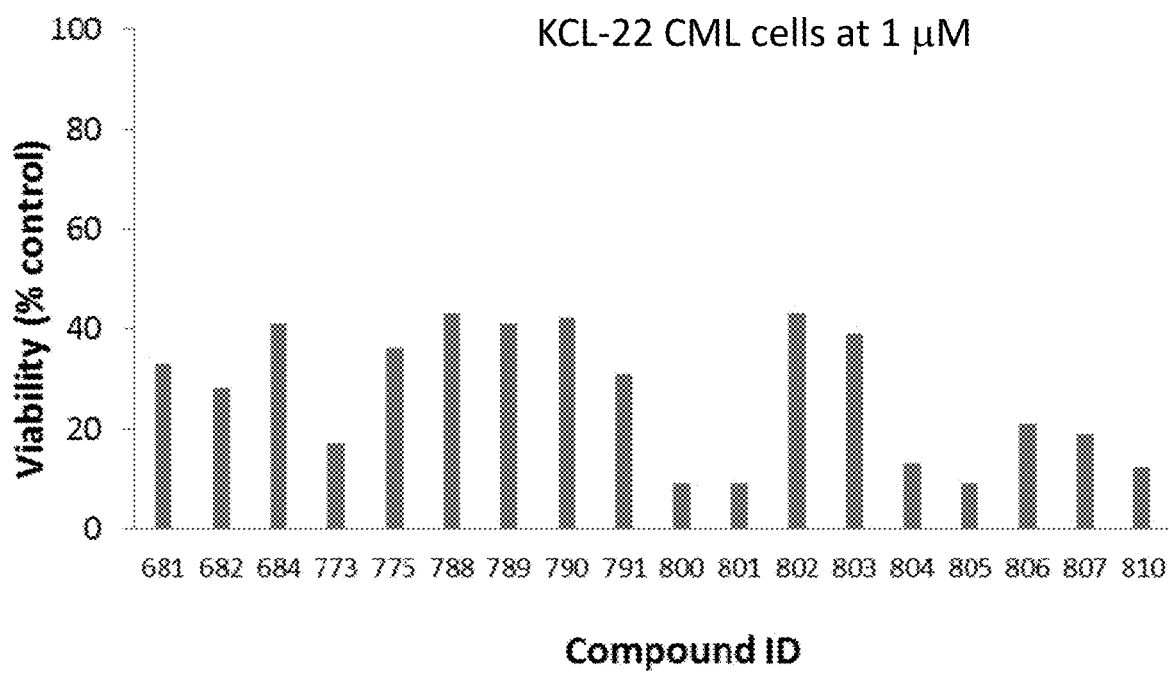
Figure 7A:
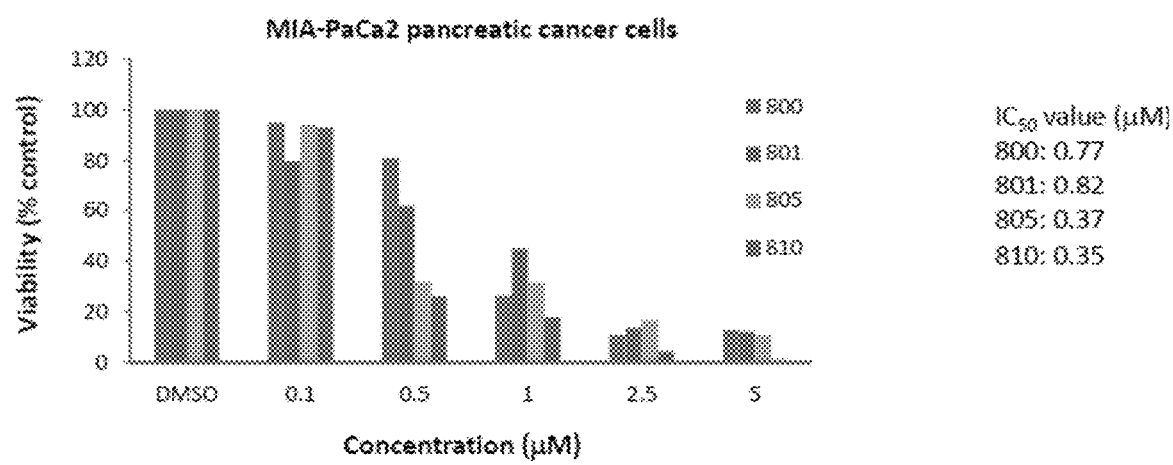
FIGS. 7A-7B: Effects of IRD Nos. 79, 80, 84, 87 and 176 on cancer cells. (A) MIA-PaCa2 pancreatic cancer cells; (B) SKOV3 ovarian cancer cells.
Figure 7B:
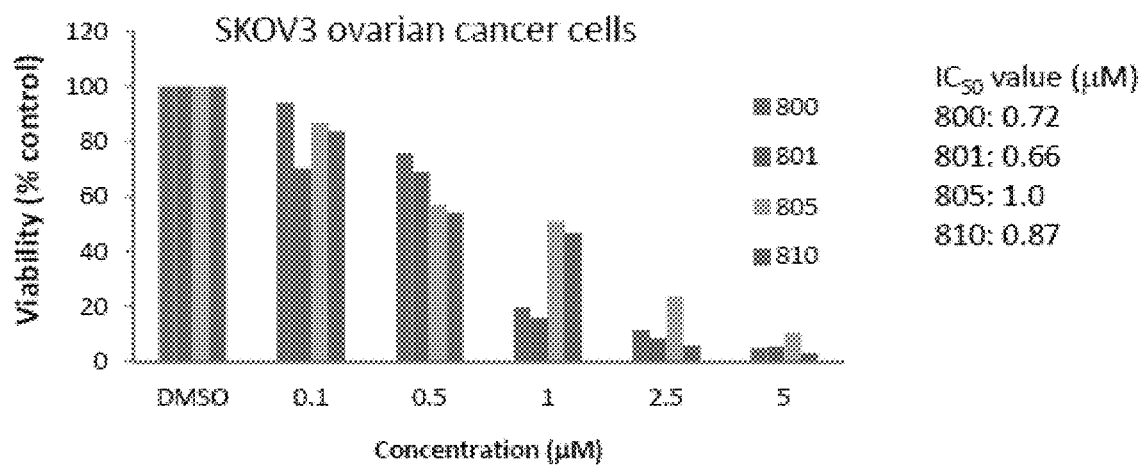
Figure 8:
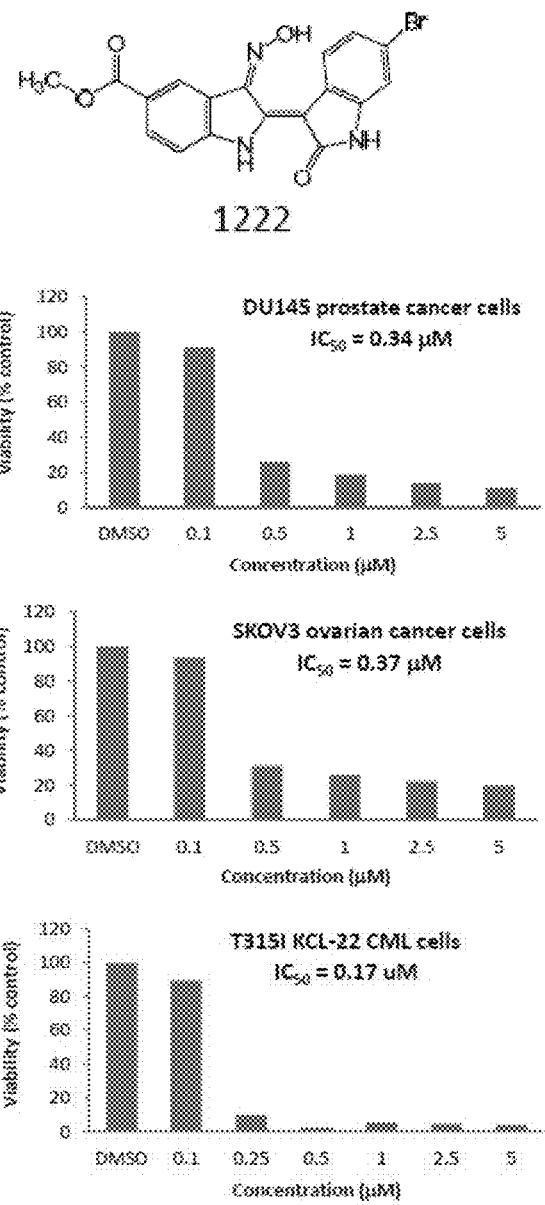
FIG. 8: Effects of IRD No. 176 on DU145 prostate cancer cells, A2058 melanoma cells, SKOV3 ovarian cancer cells, MIA-PaCa2 pancreatic cancer cells, T315I KCL-22 CML cells, and KCL022 CML cells.
Figure 9A:
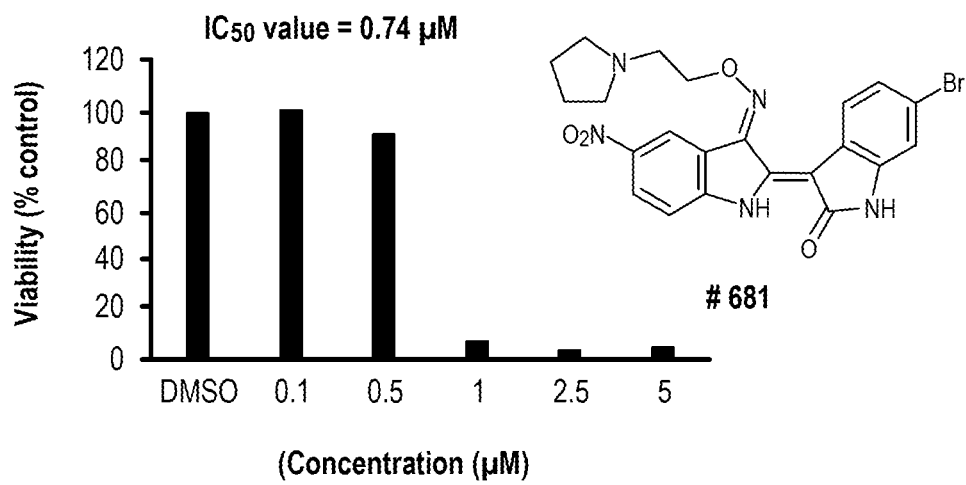
FIGS. 9A-9D—Determination of $IC_{50}$ using T315I KCL-22 CML cells for IRDs: (A) IRD No. 10; (B) IRD No. 11; (C) IRD No. 13; and (D) IRD No. 70.
Figure 9B:
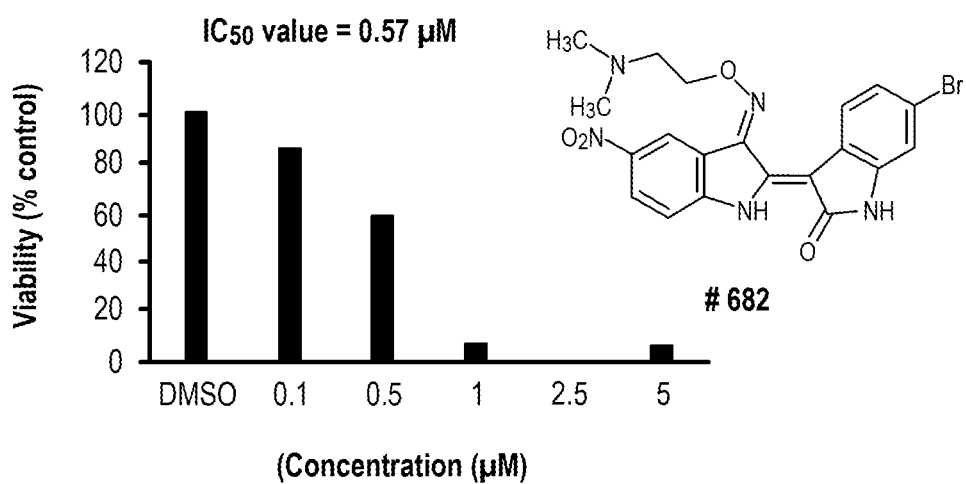
Figure 9C:
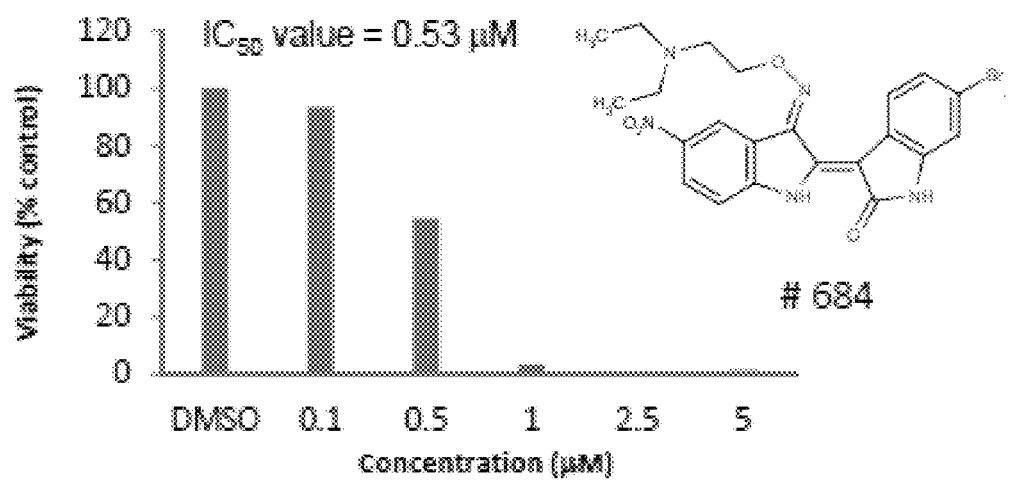
Figure 9D:
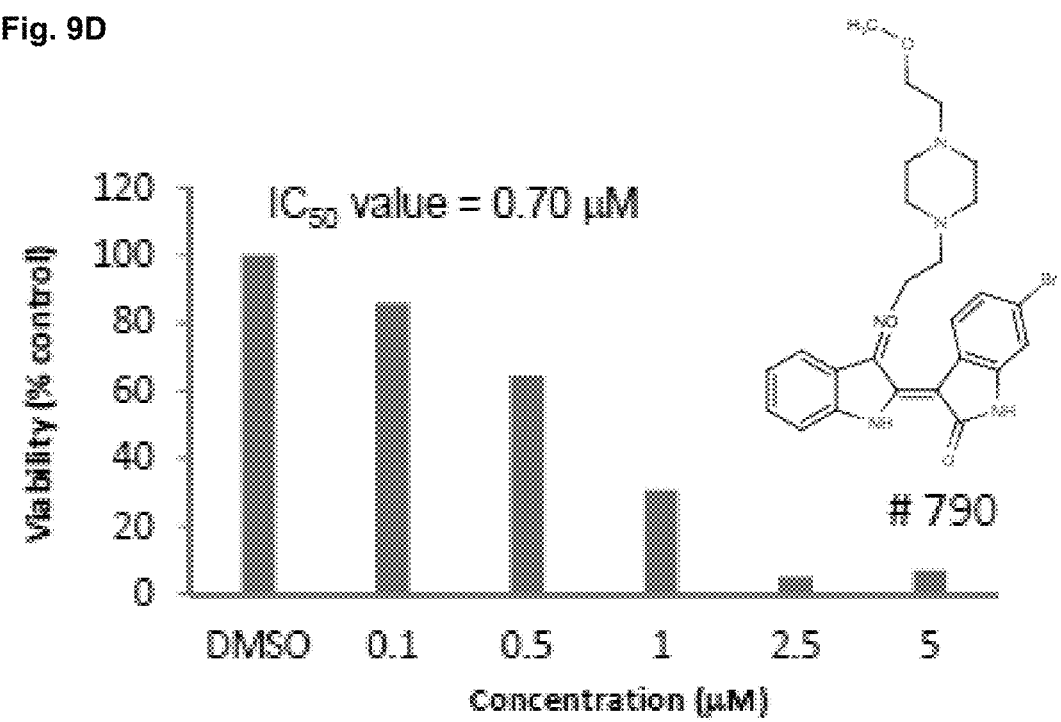
Figure 10A:
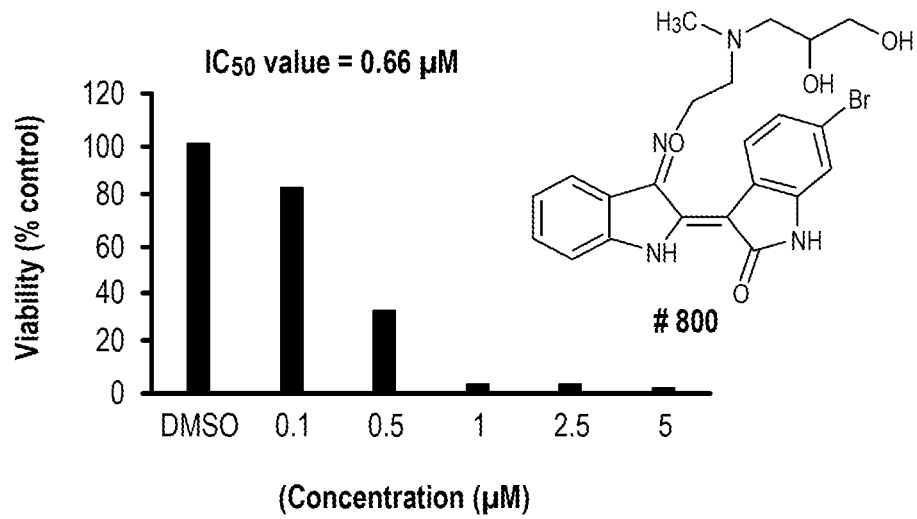
FIGS. 10A-10D—Determination of $IC_{50}$ using T315I KCL-22 CML cells for IRDs: (A) IRD No. 79; (B) IRD No. 80; (C) IRD No. 83; and (D) IRD No. 84.
Figure 10B:
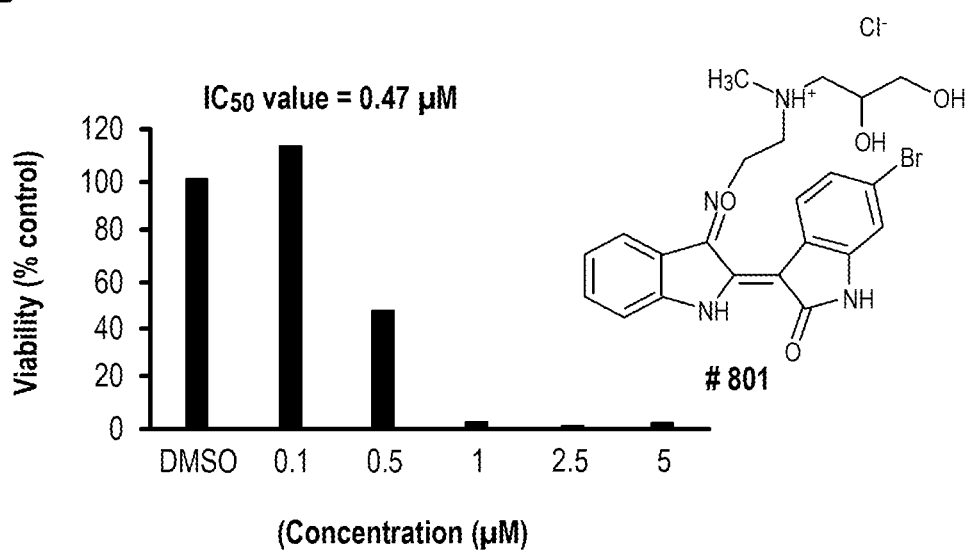
Figure 10C:
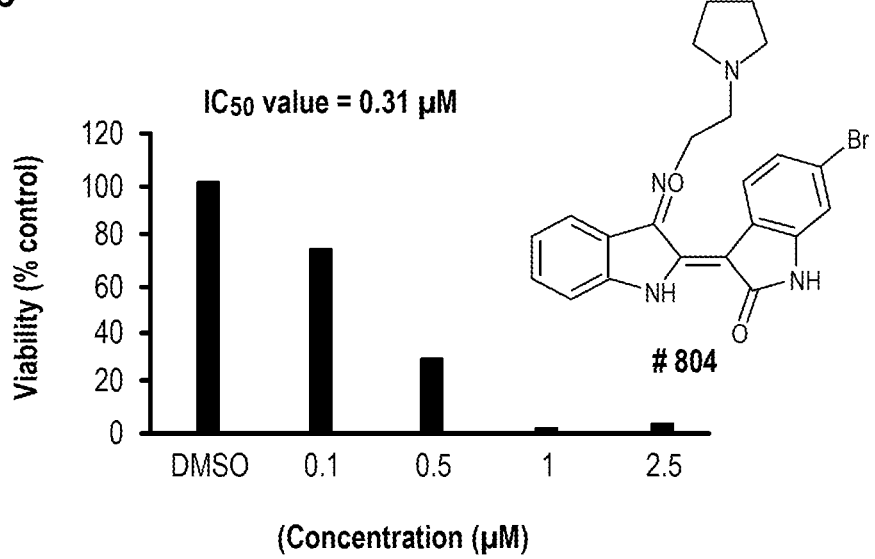
Figure 10D:
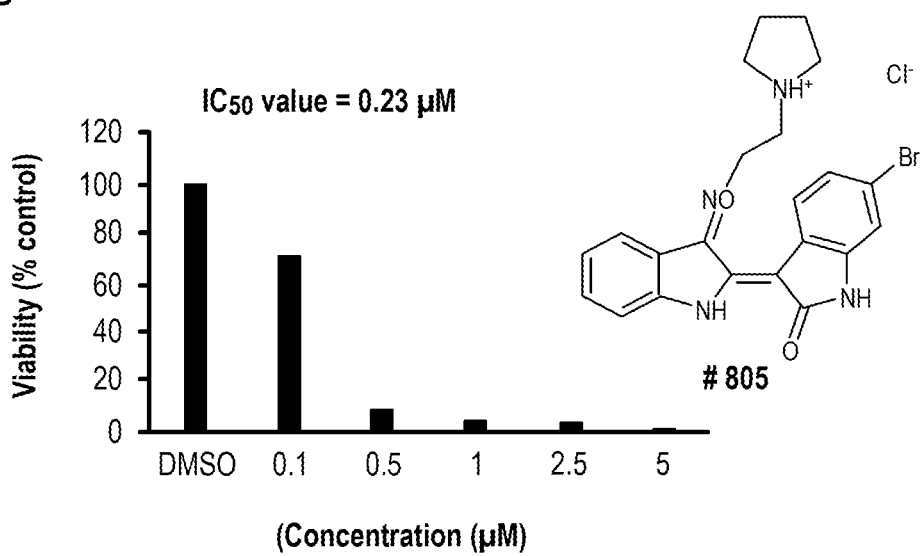
Figure 11A:
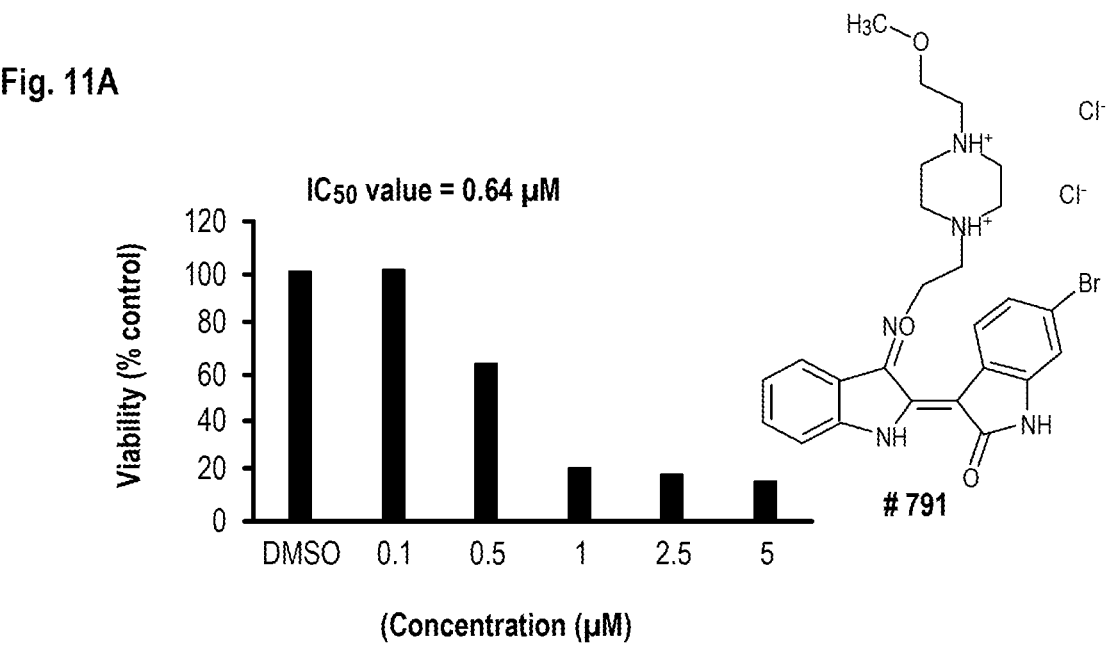
FIGS. 11A-11B—Determination of $IC_{50}$ using T315I KCL-22 CML cells for IRDs. (A) IRD No. 71; and (B) IRD No. 87.
Figure 11B:
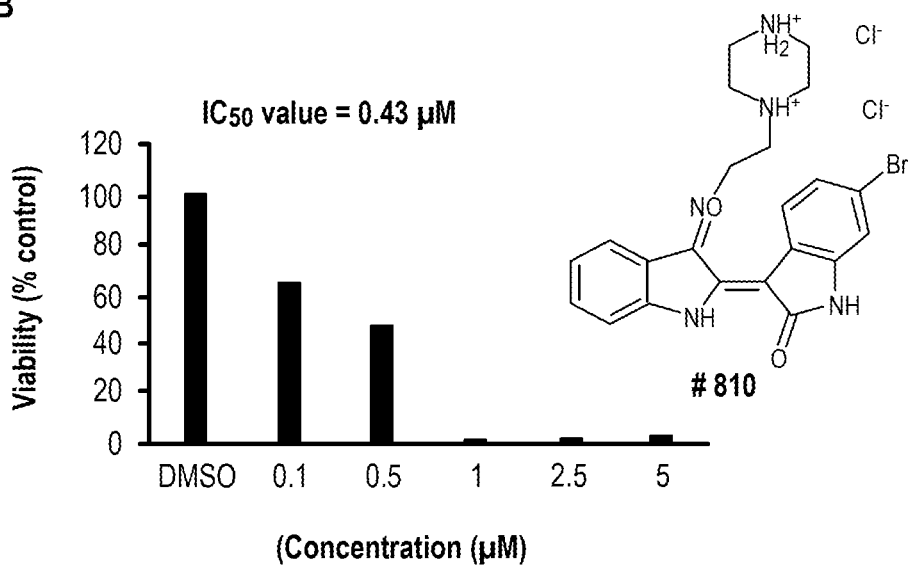

The original screening data are shown in FIGS. 3A-1-3F-3. The screening data for preferred compounds are summarized in FIG. 4. Effects of IRD Nos. 10, 11 and 13 on LY-3 lymphoma cells (200 nM), DU145 prostate cancer cells (1 µM), MIA-PaCa2 pancreatic cancer cells (1 µM), SKOV3 ovarian cancer cells (1 µM), KCL-22 CML cells (1 µM), and K562 CML cells (1 µM) were tested and shown in FIG. 5. Effects of IRD Nos. 135, 137, 138, 176, and 177 on DU145 prostate cancer cells (1 µM), MIA-PaCa2 pancreatic cancer cells (1 µM), SKOV3 ovarian cancer cells (1 µM), and A2058 melanoma cells (1 µM) were also tested and shown in FIG. 5. Effects of IRDs on viabilities of cancer cells at 1 µM concentration of the tested IRDs. Effects of IRD Nos. 10, 11, 13, 59, 70~71, 79, 80, and 83~87 on T315I mutant KCL-22 CML cells at 1 µM concentration of the tested IRDs were tested (FIG. 6A). Effects of IRD Nos. 10, 11, 13, 59, 61, 68~71, and 79~87 on KCL-22 CML cells at 1 µM concentration of the tested IRDs were also tested (FIG. 6B).

Several test compounds (IRD Nos. 9, 10-13, 59, 61, 68-71, 79-87, 115, 124, 128, 138 and 176) showed approximately 50%~ about 100% loss of cell viabilities of various cancer cells at 1 µM concentration (FIG. 4). More specifically, IRD Nos. 80 and 176 showed at least about 80% loss of cell viabilities of DU145 prostate cancer cells at 1 µM concentration. IRD Nos. 79, 80, and 176 showed at least about 95% loss of cell viabilities of A2058 Melanoma cells at 1 µM concentration. IRD Nos. 11, 79, 80, 83, 84, 87 and 176 showed at least about 85% loss of cell viabilities of PaCa2 pancreatic cancer cells at 1 µM concentration. IRD Nos. 79, 80, 84, 85 and 176 showed at least about 80% loss of cell viabilities of SKOV3 ovarian cancer cells at 1 µM concentration. IRD No. 10, 11, 13, 59, 70~71, 79, 80, 83~87, and 176 showed at least about 50% loss of cell viabilities of T315I mutant KCL-22 CML cells at 1 µM concentration. IRD Nos. 59, and 128 showed about 85% loss of cell viabilities of K562 CML cells at 1 µM concentration. IRD Nos. 79, 83-87 and 176 showed at least about 80% loss of cell viabilities of KCL-22 CML cells at 1 µM concentration. IRD Nos. 59, 79, 80, 83, 84, and 87 showed at least about 85% loss of cell viabilities of KCL-22 CML cells at 1 µM concentration. At 200 nM concentration of the test compounds, IRD Nos. 12, 13, and 83~84 showed at least about 85% loss of cell viabilities of LY-3 lymphoma cells.

Measurement of $IC_{50}$ of Selected IRDs Disclosed Herein on Cancer Cells.

Cells (DU145 cells, A2058 cells, MIA-PaCa2 cells, SKOV3 cells, T315I KCL-22 CML cells, KCL-22 CML cells, and MV4-11 AML cells) were seeded in 96-well plates (10000/well) and exposed to 1 µM of a test compound (IRDs 10, 11, 13, 70, 79-80, 83, 84, 87, and 176) for 48 hours. Dimethyl sulfoxide (DMSO) was used as the vehicle control. Viable cell numbers were determined by tetrazolium conversion to its formazan dye and absorbance was measured at 490 nm using an automated ELISA plate reader (FIGS. 7A-B~11A-B). The resulted $IC_{50}$ is summarized in FIG. 12.

Example 2. Effects of IRDs on Protein Kinases ABL1, ABL1 (T315I Mutant), Aurora A, CDK2/cyclinA, c-Src, FGR, FLT3, FYN, GSK3β, HCK, LYN, JAK2, and TYK2

The in vitro kinase assays of an IRD (IRD Nos. 10, 11, 13, 61, 70, 71, 79, 80, 83~87 and 176) were carried out using recombinant proteins according to the procedure disclosed in Nam 2012 (Nam, S., Xie, J., Perkins, A., Ma, Y., Yang, F., Wu, J., Wang, Y., Xu, R. Z., Huang, W., Horne, D. A., and Jove, R. (2012) Novel synthetic derivatives of the natural product berbamine inhibit Jak2/Stat3 signaling and induce apoptosis of human melanoma cells, Molecular oncology), which is hereby incorporated by reference in its entirety, as if fully set forth herein. The results are summarized in FIG. 13. Several IRDs showed low $IC_{50}$ for kinases ABL1, ABL1 (T315I mutant), Aurora A, CDK2/cyclinA, c-Src, FGR, FLT3, FYN, GSK3β, HCK, LYN, JAK2, and/or TYK2.

For example, when the protein kinase is ABL1, IRD Nos. 11, 13, 61, 70, 71, 79, 80, 83~87, and 176 showed $IC_{50}<10$ k nM, IRD Nos. 61, 79, 80, and 84~87 showed $IC_{50}<200$ nM, IRD Nos. 61, 79, 80, and 87 showed $IC_{50}<20$ nM, and IRD No. 87 showed $IC_{50}<1$ nM.

When the protein kinase is ABL1 (T315I mutant), IRD Nos. 61, 79, 80, 83~85 and 87 showed $IC_{50}<6$ k nM; IRD Nos. 61, 79, 80, and 87 showed $IC_{50}<200$ nM; and IRD NO. 87 showed $IC_{50}<10$ nM.

When the protein kinase is Aurora A, IRD Nos. 61, 70, 79, 80, 83~87, and 176 showed $IC_{50}<900$ nM; and IRD Nos. 79, 85, and 87 showed $IC_{50}<15$ nM.

When the protein kinase is c-Src, IRD Nos. 10, 11, 13, 61, 70, 71, 79, 80, 83~87, and 176 showed $IC_{50}<4$ k nM; IRD Nos. 61, 70, 71, 79, 80, and 83~87 showed $IC_{50}<5$ nM.

When the protein kinase is CDK2/cyclin A, FGR, FLT3, FYN, GSK3β, HCK, LYN, or TYK2, IRD No. 176 showed $IC_{50}$~1,200 nM or lower.

When the protein kinase is JAK2, IRD Nos. 61, 79, 80, 83, 84 and 87 showed $IC_{50}<1,200$ nM; and IRD Nos. 79, 80, and 87 showed $IC_{50}<600$ nM.

Example 3. IRDs Inhibited Stat5 Activity in Cancer Cells

Cell Lines and Reagents

Human KCL-22 CML cells were obtained from the American Type Culture Collection (ATCC). Cells were cultured in RPMI-1640 media containing 10% fetal bovine serum (FBS). Imatinib-resistant human KCL-22 CML cells expressing the T315I mutant Bcr-Abl (KCL-22M) were derived from human KCL-22 CML cells (Yuan et al., 2010). Cells were grown in RPMI 1640 media supplemented with 10% FBS. Monoclonal antibodies to Abl protein and phosphotyrosine (p-Y) were obtained from BD Biosciences (San Diego, Calif.). Polyclonal antibodies to p-Stat5 (Y694) and p-Src family (Y419) were obtained from Cell Signaling Technologies (Cambridge, Mass.). Polyclonal antibodies to Stat5 were from Santa Cruz Biotechnology (Santa Cruz, Calif.). Monoclonal antibody to Src was obtained from Millipore (Billerica, Mass.).

Western Blot Analyses

Western analyses were performed as described previously with minor modification (Nam et al., 2005b). Briefly, KCL-22 CML and T315I KCL-22 CML cells were treated with IRDs. Whole-cell lysates were resolved by SDS-PAGE and immunoblotted with specific antibodies. Primary phospho-specific antibodies were incubated in TBS (pH 7.5) with 0.1% Tween-20 and 5% BSA with gentle agitation overnight at 4° C. Horseradish peroxidase-conjugated secondary antibodies were incubated in TBS (pH 7.5) with 5% nonfat milk and 0.1% Tween-20 at a 1:2000 dilution for 1 hour at room temperature. Positive immuno-reactive proteins were detected using the ECL system (Pierce, Rockford, Ill.).

1a. IRD No. 87 Reduced Levels of p-Stat5 in CML Cells

Figure 14:
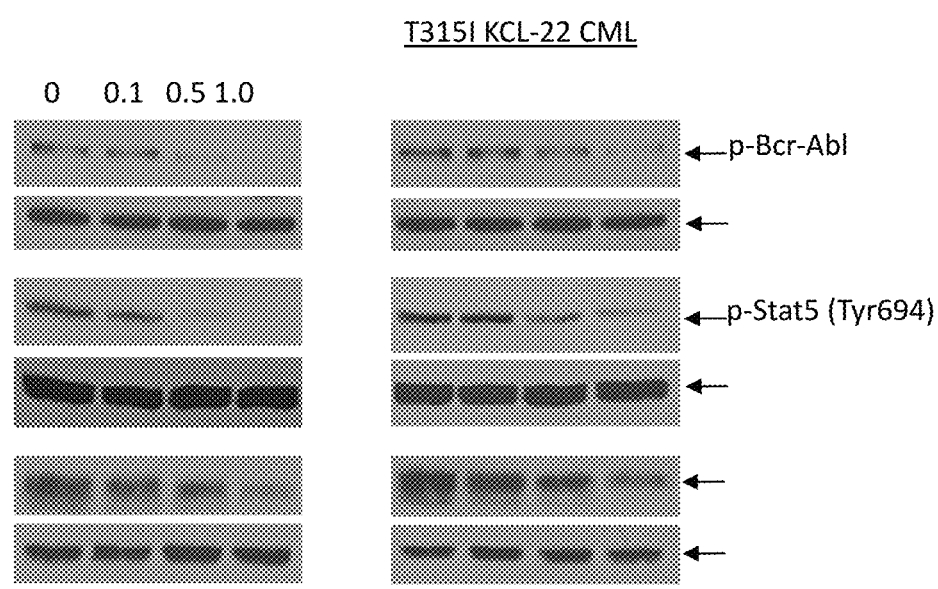
FIG. 14: Effects of IRD No. 87 on Bcr-Abl/Stat5 or Src/Stat5 signaling in KCL-22 CML cells and T315I KCL-22 CML cells (imatinib-resistant human KCL-22 CML cells expressing the T315I mutant Bcr-Abl, also referred to as T315I KCL-22 CML).

Western blot analysis with specific antibodies to p-Stat5 was performed to evaluate the effects of IRD No. 87 on phosphorylation of Stat5 in KCL-22 CML and T315I KCL-22 CML cells. Cells were treated with IRD No. 87 in a dose-dependent manner for 4 hours and Western blot analysis was performed using whole-cell lysates as described above. IRD No. 87 substantially inhibited tyrosyl phosphorylation of Stat5 at 5 µM, whereas total Stat5 levels were unchanged (FIG. 14, middle panels).

It has been shown before that IRDs inhibit Src/Stat3 signaling (Nam et al., 2005a), associated with induction of apoptosis in solid tumor cells. Similarly, these results suggest that IRDs could directly target upstream kinases such as Bcr-Abl and/or SFKs, which constitutively activate Stat5 via tyrosyl phosphorylation of Stat5 at Y694 in chronic leukemias.

1b. IRD No. 87 Inhibited Tyrosyl Phosphorylation of Src

To examine the effects of IRD No. 87 on autophosphorylation of Src in KCL-22 CML and T315I KCL-22 CML cells, Western blot analysis was performed with specific antibodies to p-Src and Src as described above. IRD No. 87 caused strong reduction of autophosphorylation of Src at 1.0 µM in KCL-22 CML and T315I KCL-22 CML cells (FIG. 14, bottom panels).

1c. Effect of IRD No. 87 on Abl Kinase Activity and Levels of p-Bcr-Abl

To address whether IRD No. 87 inhibits tyrosyl phosphorylation of endogenous Bcr-Abl in KCL-22 CML and T315I KCL-22 CML cells, Western blot analysis was performed using lysates from the cells treated with IRD No. 87 in a dose-dependent manner for 4 hours as described above. IRD No. 87 reduced levels of p-Bcr-Abl at concentrations higher than 0.5 µM in cells (FIG. 14, top panels). Indirubins are known to be ATP competitors and bind to the ATP binding pocket in the catalytic domain of CDKs (Hoessel et al., 1999). Likewise, the inhibitory activity IRD No. 87 might result from ATP-competitive binding into the Bcr-Abl kinase binding pocket in CML cells.

Figure 15A:
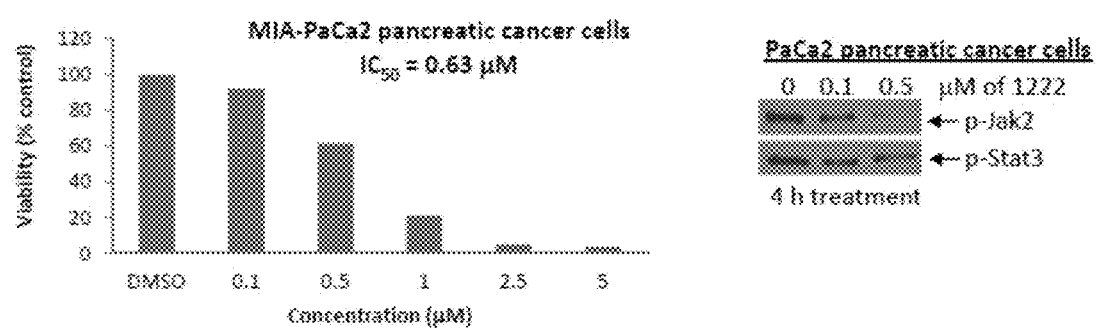
FIGS. 15A-15B: Effects of IRD No. 176 on Stat3 signaling in cancer cells. (A) PaCa2 pancreatic cancer cells; and (B) SKOV3 ovarian cancer cells.

2a. IRD No. 176 Reduced Levels of p-Stat3 and p-Jak2 in PaCa2 Pancreatic Cancer Cells Western blot analysis with specific antibodies to p-Stat3 or p-Jak2 was performed to evaluate the effects of IRD No. 176 on phosphorylation of Stat3 or Jak2 in PaCa2 pancreatic cancer cells. Cells were treated with IRD No. 176 in a dose-dependent manner for 4 hours and Western blot analysis was performed using whole-cell lysates as described above. IRD No. 176 substantially inhibited phosphorylation of Stat3 and Jak2 at 0.5 µM (FIG. 15A).

Figure 15B:
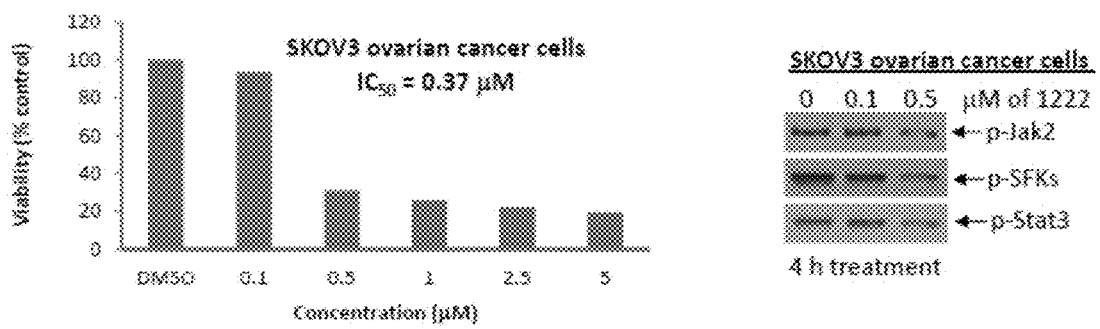

2b. IRD No. 176 Reduced Levels of p-Stat3, p-SFKs and p-Jak2 in SKOV3 Ovarian Cancer Cells Western blot analysis with specific antibodies to p-Stat3, p-SFKs or p-Jak2 was performed to evaluate the effects of IRD No. 176 on phosphorylation of Stat3 or Jak2 in SKOV3 ovarian cancer cells. Cells were treated with IRD No. 176 in a dose-dependent manner for 4 hours and Western blot analysis was performed using whole-cell lysates as described above. IRD No. 176 substantially inhibited phosphorylation of Stat3 and Jak2 at 0.5 µM (FIG. 15B).

2c. IRD No. 176 Reduced Levels of p-Stat5 in MV4-11 AML Cells

Western blot analysis with specific antibodies to p-Stat5 was performed to evaluate the effects of IRD No. 176 on phosphorylation of Stat5 in MV4-11 AML cells. Cells were treated with IRD No. 176 in a dose-dependent manner for 4 hours and Western blot analysis was performed using whole-cell lysates as described above. IRD No. 176 substantially inhibited phosphorylation of Stat5 at 0.5 µM (FIG. 16B).

3. Discussion

Several synthetic IRDs have shown potent antitumor activities, blocking constitutive Stat3 signaling in human solid tumor cell lines (Nam et al., 2005a). IRD No. 87 showed strong inhibitory potency against Stat5 signaling in human CML cells; and IRD No. 176 showed strong inhibitory potency against Stat5 or Stat3 signaling in PaCa2 pancreatic cancer cells, SKOV3 ovarian cancer cells, and MV4-11 AML cells.

In comparison of both of Src and ABL kinase activities in vitro, IRD No. 87 inhibited ABL kinase activity at about 15-fold higher concentration (FIG. 13). In addition, IRD No. 87 reduced levels of p-Bcr-Abl at higher concentrations in cells (FIG. 14). These findings suggest that IRDs inhibited Src/Stat5 signaling more strongly than Bcr-Abl/Stat5 signaling in CML cells. These effects of IRD No. 87 could be responsible for induction of apoptosis, suggesting that IRD No. 87 and other IRDs disclosed herein may have potential as therapeutic agents in drug-resistant CML cells.

IRD No. 176 inhibited Jak2, Stat3 kinase activity in PaCa2 pancreatic cancer cells (FIG. 15A) and SKOV3 ovarian cancer cells (FIG. 15B). These findings suggest that IRDs inhibited Stat3 signaling in pancreatic and ovarian cancer cells.

Figure 16A:
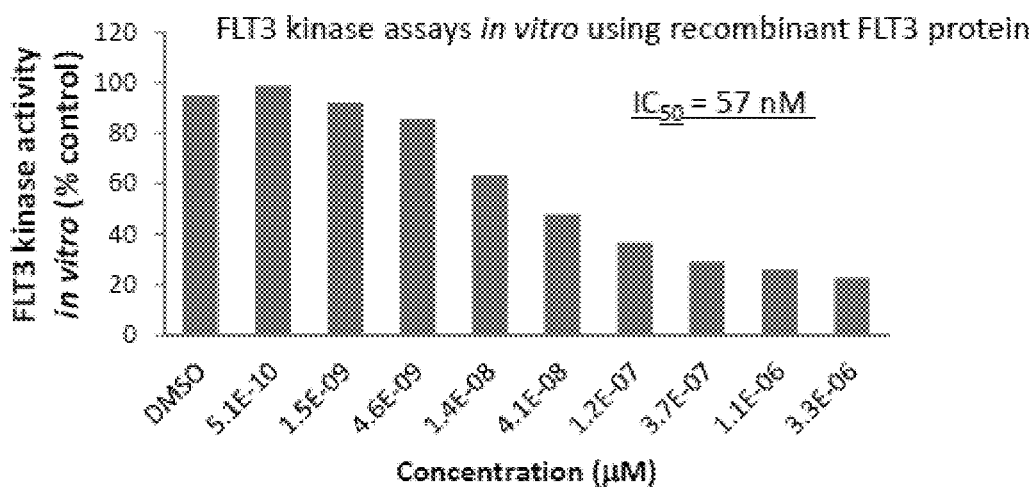
FIGS. 16A-16C: Effects of IRD No. 176 on MV4-11 AML cells. Effects of IRD No. 176 on (A) FLT3 kinase activity; (B) Stat5 activation in MV4-11 AML cells; and (C) MV4-11 AML cells.
Figure 16B:
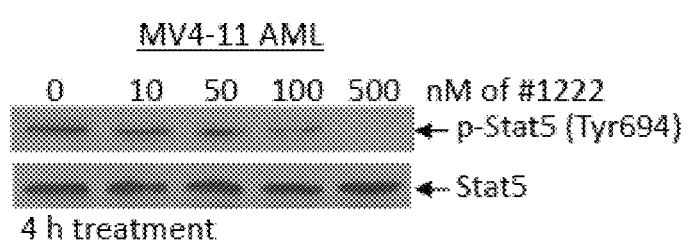
Figure 16C:
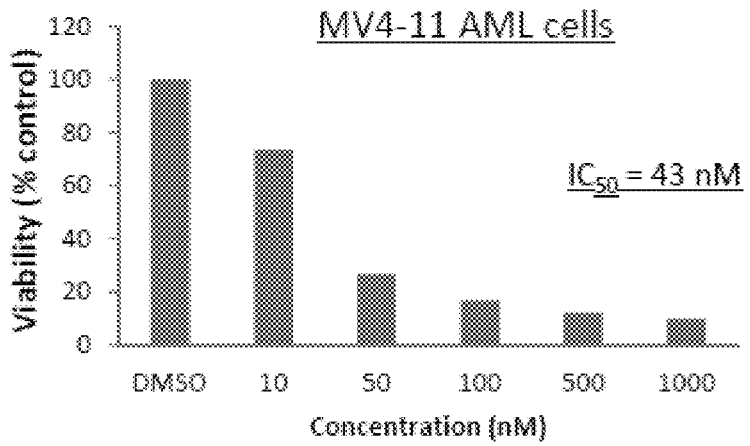

IRD No. 176 significantly reduced levels of p-Stat5 at a low concentration in MV4-11 AML cells and showed inhibition of FLT3 kinase (FIGS. 16A and 16B). These findings suggest that IRDs inhibited FLT3/Stat5 signaling in AML cells.

In particular, IRDs disclosed herein are new therapeutics for wild type or T315I mutant Bcr-Abl-positive CML, pancreatic cancer, ovarian cancer cells, and/or AML patients.

Example 4. Preparation of Examples of 5-Bromo-Indirubin IRDs 5-bromo-isatin (1 eq) and 3-acetoxyindole (0.8 eq) were dissolved in methanol in the presence of sodium carbonate. After the mixture was stirred for about 3.5 h. Methanolic water (1/1) was then added to the mixture and the formed precipitate was filtered, washed with water and dried to afford the 5-bromoindirubin with about 80% yield.

Example 5. Preparation of 5-Bromo-3'-Oxim-Indirubin 5-bromoindirubin (1 eq) was dissolved in pyridine in the presence of hydroxylamine hydrochloride (10 eq) and refluxed for 1.5 h. After the reaction mixture was cooled to room temperature, water was added and the reaction mixture was filtered. The obtained solid was washed with water to afford the 5-bromo-3'-oxim-indirubin (5-BIO) in about quantitative yield.

Example 6. Preparation of 5-Bromoindirubin-3'-(O-Bromoethyl)Oxime

Triethylamine and dibromoethane (2 eq) was added to a solution of 5-BIO (1 eq) in DMF. The reaction was stirred for 24 h at room temperature. Then water was added and the formed precipitate was filtered and washed with water to afford the 5-bromoindirubin-3'-(O-bromoethyl)-oxime.

Example 7. Preparation of Amines 5-bromoindirubin-3'-(O-bromoethyl)oxime was dissolved in anhydrous acetonitrile. An excess amount of the appropriate amine was added to the 5-bromoindirubin-3'-(O-bromoethyl)oxime acetonitrile solution, and the mixture was then heated at 85° C. in CEM Single-Mode microwave at 100 W for 40 min. The solvent was evaporated and the solid was triturated in water, filtered and wash with water and cyclohexane to afford the amines in about 80-90% yield.

Examples of the appropriate amines include diethylamine, piperazine, N-methylpiperazine, 3-methylamine-1,2-propanediol, 1-(2-hydroxyethyl)piperazine and 1-[2-(2-hydroxyethoxy)-ethyl]piperazine.

The references cited in this application and listed below are hereby incorporated by reference in their entireties, as if fully set forth herein:

Aichberger, K. J., Mayerhofer, M., Krauth, M. T., Skvara, H., Florian, S., Sonneck, K., Akgul, C., Derdak, S., Pickl, W. F., Wacheck, V., Selzer, E., Monia, B. P., Moriggl, R., Valent, P., Sillaber, C., 2005. Identification of mcl-1 as a BCR/ABL-dependent target in chronic myeloid leukemia (CML): evidence for cooperative antileukemic effects of imatinib and mcl-1 antisense oligonucleotides. Blood 105, 3303-3311.

Benekli, M., Baer, M. R., Baumann, H., Wetzler, M., 2003. Signal transducer and activator of transcription proteins in leukemias. Blood 101, 2940-2954.

Bromann, P. A., Korkaya, H., Courtneidge, S. A., 2004. The interplay between Src family kinases and receptor tyrosine kinases. Oncogene 23, 7957-7968.

Bromberg, J. F., Wrzeszczynska, M. H., Devgan, G., Zhao, Y., Pestell, R. G., Albanese, C., Darnell, J. E., Jr., 1999. Stat3 as an oncogene. Cell 98, 295-303.

Buettner, R., Mora, L. B., Jove, R., 2002. Activated STAT signaling in human tumors provides novel molecular targets for therapeutic intervention. Clin Cancer Res 8, 945-954.

Carlesso, N., Frank, D. A., Griffin, J. D., 1996. Tyrosyl phosphorylation and DNA binding 17 activity of signal transducers and activators of transcription (STAT) proteins in hematopoietic cell lines transformed by Bcr/Abl. J Exp Med 183, 811-820.

Donato, N. J., Wu, J. Y., Stapley, J., Gallick, G., Lin, H., Arlinghaus, R., Talpaz, M., 2003. BCR-ABL independence and LYN kinase overexpression in chronic myelogenous leukemia cells selected for resistance to STI571. Blood 101, 690-698.

Eisenbrand, G., Hippe, F., Jakobs, S., Muehlbeyer, S., 2004. Molecular mechanisms of indirubin and its derivatives: novel anticancer molecules with their origin in traditional Chinese phytomedicine. J Cancer Res Clin Oncol 130, 627-635.

Gesbert, F., Griffin, J. D., 2000. Bcr/Abl activates transcription of the Bcl-X gene through STAT5. Blood 96, 2269-2276.

Haura, E. B., Turkson, J., Jove, R., 2005. Mechanisms of disease: Insights into the emerging role of signal transducers and activators of transcription in cancer. Nat Clin Pract Oncol 2, 315-324.

Herrington, J., Sm it, L. S., Schwartz, J., Carter-Su, C., 2000. The role of STAT proteins in growth hormone signaling. Oncogene 19, 2585-2597.

Hoessel, R., Leclerc, S., Endicott, J. A., Nobel, M. E., Lawrie, A., Tunnah, P., Leost, M., Damiens, E., Marie, D., Marko, D., Niederberger, E., Tang, W., Eisenbrand, G., Meijer, L., 1999. Indirubin, the active constituent of a Chinese antileukaemia medicine, inhibits cyclin-dependent kinases. Nat Cell Biol 1, 60-67.

Holtz, M. S., Slovak, M. L., Zhang, F., Sawyers, C. L., Forman, S. J., Bhatia, R., 2002. Imatinib mesylate (STI571) inhibits growth of primitive malignant progenitors in chronic myelogenous leukemia through reversal of abnormally increased proliferation. Blood 99, 3792-3800.

Horita, M., Andreu, E. J., Benito, A., Arbona, C., Sanz, C., Benet, I., Prosper, F., Fernandez-Luna, J. L., 2000. Blockade of the Bcr-Abl kinase activity induces apoptosis of chronic myelogenous leukemia cells by suppressing signal transducer and activator of transcription 5-dependent expression of Bcl-xL. J Exp Med 191, 977-984.

Huang, M., Dorsey, J. F., Epling-Burnette, P. K., Nimmanapalli, R., Landowski, T. H., Mora, L. B., Niu, G., Sinibaldi, D., Bai, F., Kraker, A., Yu, H., Moscinski, L., Wei, S., Djeu, J., Dalton, W. S., Bhalla, K., Loughran, T. P., Wu, J., Jove, R., 2002.

Inhibition of Bcr-Abl kinase activity by PD180970 blocks constitutive activation of Stat5 and growth of CML cells. Oncogene 21, 8804-8816.

Klejman, A., Schreiner, S. J., Nieborowska-Skorska, M., Slupianek, A., Wilson, M., Smithgall, T. E., Skorski, T., 2002. The Src family kinase Hck couples BCR/ABL to STAT5 activation in myeloid leukemia cells. Embo J 21, 5766-5774.

Konig, H., Copland, M., Chu, S., Jove, R., Holyoake, T. L., Bhatia, R., 2008. Effects of dasatinib on SRC kinase activity and downstream intracellular signaling in primitive chronic myelogenous leukemia hematopoietic cells. Cancer Res 68, 9624-9633.

Lionberger, J. M., Wilson, M. B., Smithgall, T. E., 2000. Transformation of myeloid leukemia cells to cytokine independence by Bcr-Abl is suppressed by kinasedefective Hck. The Journal of biological chemistry 275, 18581-18585.

Marko, D., Schatzle, S., Friedel, A., Genzlinger, A., Zankl, H., Meijer, L., Eisenbrand, G., 2001. Inhibition of cyclin-dependent kinase 1 (CDK1) by indirubin derivatives in human tumour cells. Br J Cancer 84, 283-289.

Nam, S., Buettner, R., Turkson, J., Kim, D., Cheng, J. Q., Muehlbeyer, S., Hippe, F., Vatter, S., Merz, K. H., Eisenbrand, G., Jove, R., 2005a. Indirubin derivatives inhibit Stat3 signaling and induce apoptosis in human cancer cells. Proc Natl Acad Sci USA 102, 5998-6003.

Nam, S., Kim, D., Cheng, J. Q., Zhang, S., Lee, J. H., Buettner, R., Mirosevich, J., Lee, F. Y., Jove, R., 2005b. Action of the Src family kinase inhibitor, dasatinib (BMS-354825), on human prostate cancer cells. Cancer Res 65, 9185-9189.

Nam, S., Williams, A., Vultur, A., List, A., Bhalla, K., Smith, D., Lee, F. Y., Jove, R., 2007. Dasatinib (BMS-354825) inhibits Stat5 signaling associated with apoptosis in chronic myelogenous leukemia cells. Mol Cancer Ther 6, 1400-1405.

Nelson, E. A., Walker, S. R., Li, W., Liu, X. S., Frank, D. A., 2006. Identification of human STAT5-dependent gene regulatory elements based on interspecies homology. The Journal of biological chemistry 281, 26216-26224.

Nieborowska-Skorska, M., Wasik, M. A., Slupianek, A., Salomoni, P., Kitamura, T., Calabretta, B., Skorski, T., 1999. Signal transducer and activator of transcription (STAT)5 activation by BCR/ABL is dependent on intact Src homology (SH)3 and SH2 domains of BCR/ABL and is required for leukemogenesis. J Exp Med 189, 1229-1242.

Parsons, S. J., Parsons, J. T., 2004. Src family kinases, key regulators of signal transduction. Oncogene 23, 7906-7909.

Ptasznik, A., Nakata, Y., Kalota, A., Emerson, S. G., Gewirtz, A. M., 2004. Short interfering RNA (siRNA) targeting the Lyn kinase induces apoptosis in primary, and drug-resistant, BCR-ABL1(+) leukemia cells. Nat Med 10, 1187-1189.

Quintas-Cardama, A., Kantarjian, H., Jones, D., Nicaise, C., O'Brien, S., Giles, F., Talpaz, M., Cortes, J., 2007. Dasatinib (BMS-354825) is active in Philadelphia chromosome-positive chronic myelogenous leukemia after imatinib and nilotinib (AMN107) therapy failure. Blood 109, 497-9

Shah, N. P., Tran, C., Lee, F. Y., Chen, P., Norris, D., Sawyers, C. L., 2004. Overriding imatinib resistance with a novel ABL kinase inhibitor. Science 305, 399-401.

Silva, C. M., 2004. Role of STATs as downstream signal transducers in Src family inasemediated tumorigenesis. Oncogene 23, 8017-8023.

Vougogiannopoulou, K., Ferandin, Y., Bettayeb, K., Myrianthopoulos, V., Lozach, O., Fan, Y., Johnson, C. H., Magiatis, P., Skaltsounis, A. L., Mikros, E., Meijer, L., 2008. Soluble 3',6-substituted indirubins with enhanced selectivity toward glycogen synthase kinase −3 alter circadian period. J Med Chem 51, 6421-6431.

Wilson, M. B., Schreiner, S. J., Choi, H. J., Kamens, J., Smithgall, T. E., 2002. Selective pyrrolo-pyrimidine inhibitors reveal a necessary role for Src family kinases in Bcr-Abl signal transduction and oncogenesis. Oncogene 21, 8075-8088.

Wu, J., Meng, F., Lu, H., Kong, L., Bornmann, W., Peng, Z., Talpaz, M., Donato, N. J., 2008. Lyn regulates BCR-ABL and Gab2 tyrosine phosphorylation and c-Cbl protein stability in imatinib-resistant chronic myelogenous leukemia cells. Blood 111, 3821-3829.

Xiao, Z., Hao, Y., Liu, B., Qian, L., 2002. Indirubin and meisoindigo in the treatment of chronic myelogenous leukemia in China. Leuk Lymphoma 43, 1763-1768.

Yu, H., Jove, R., 2004. The STATs of cancer—new molecular targets come of age. Nat Rev Cancer 4, 97-105.

Yu, H., Pardoll, D., Jove, R., 2009. STATs in cancer inflammation and immunity: a leading role for STAT3. Nat Rev Cancer 9, 798-809.

Yuan, H., Wang, Z., Gao, C., Chen, W., Huang, Q., Yee, J. K., Bhatia, R., 2010. BCRABL gene expression is required for its mutations in a novel KCL-22 cell culture model for acquired resistance of chronic myelogenous leukemia. The Journal of biological chemistry 285, 5085-5096.

Zhou, J., Bi, C., Janakakumara, J. V., Liu, S. C., Chng, W. J., Tay, K. G., Poon, L. F., Xie, Z., Palaniyandi, S., Yu, H., Glaser, K. B., Albert, D. H., Davidsen, S. K., Chen, C. S., 2009. Enhanced activation of STAT pathways and over-expression of surviving confer resistance to FLT3 inhibitors and could be therapeutic targets in AML. Blood 113, 4052-4062.

The invention claimed is:

1. A method of treating a cancer or tumor in a subject comprising administering to the subject a therapeutically effective amount of an indirubin derivative (IRD) selected from the group consisting of IRD Nos. 9-13, 59, 61, 68-71, 79-87, 115, 124, 128 and 176, the cancer or tumor being selected from the group consisting of CML, prostate cancer, melanoma, pancreatic cancer, ovarian cancer, leukemia, and lymphoma

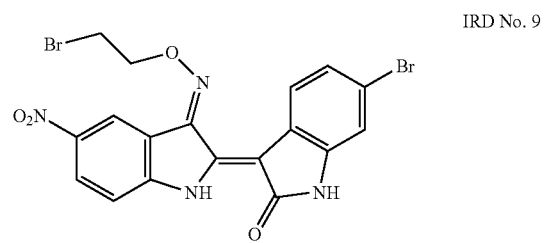

IRD No. 9

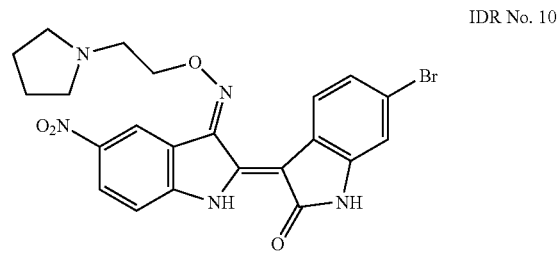

IDR No. 10

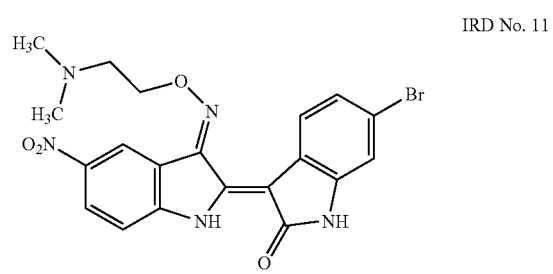

IRD No. 11

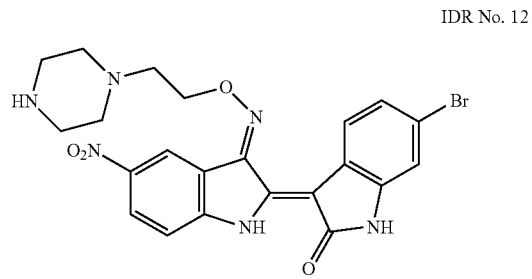

IDR No. 12

-continued
IRD No. 13
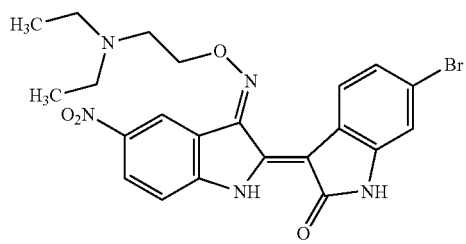
IDR No. 59
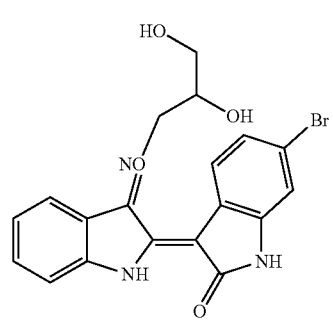
IRD No. 61
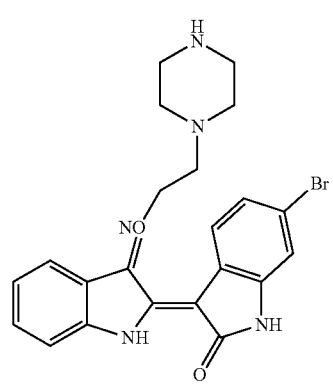
IDR No. 68
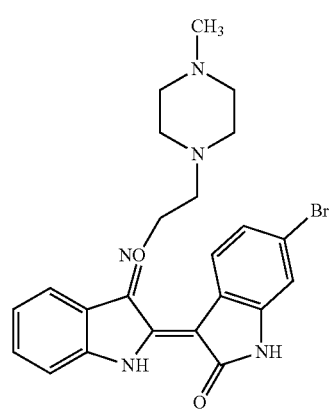
-continued
IRD No. 69
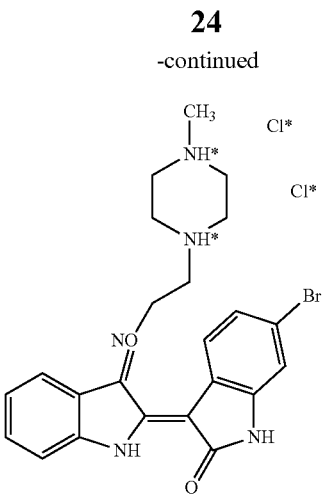
IDR No. 70
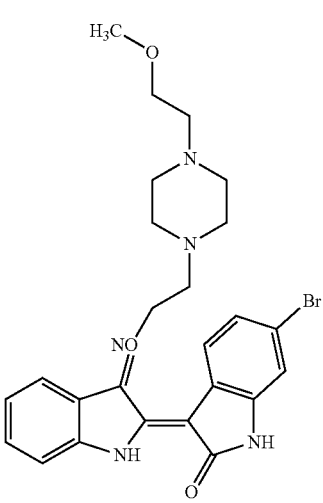
IRD No. 71
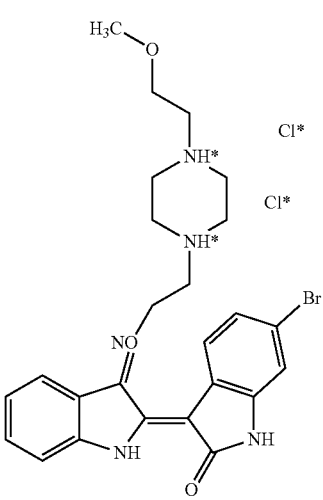

IDR No. 79
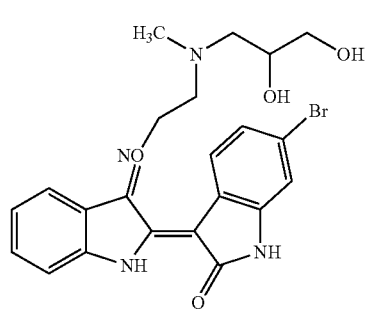
IRD No. 80
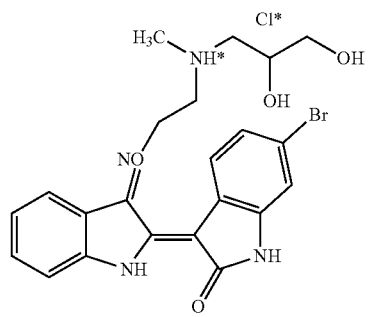
IDR No. 81
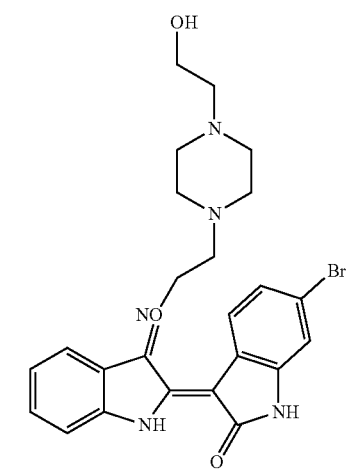
IRD No. 82
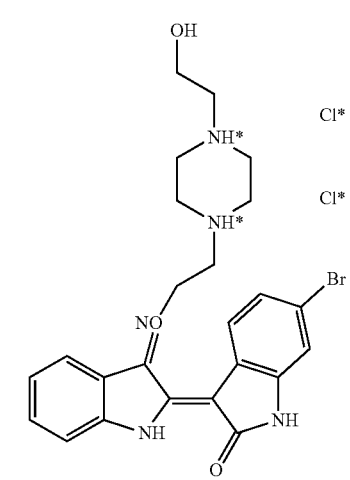
IDR No. 83
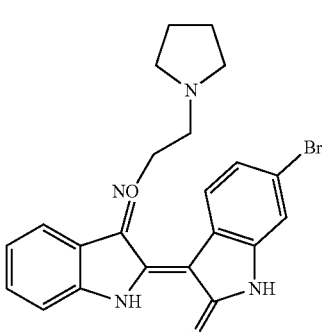
IRD No. 84
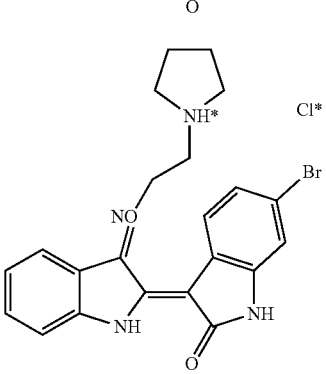
IDR No. 85
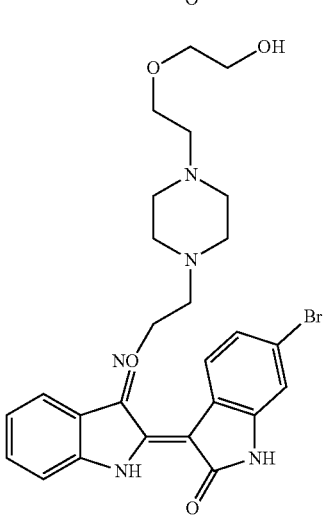
IRD No. 86
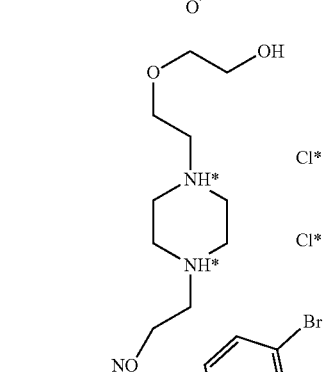

IDR No. 87
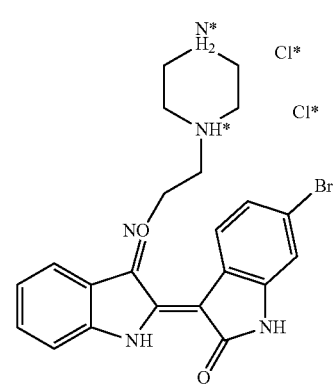

IRD No. 115
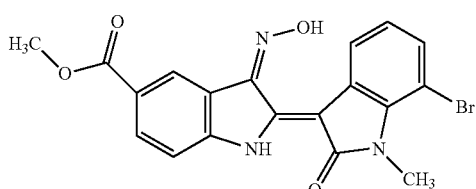

IDR No. 124
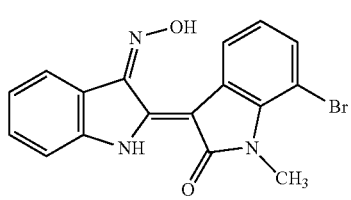

IRD No. 128
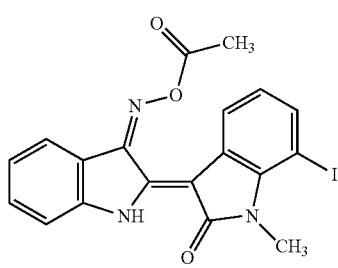

IDR No. 176
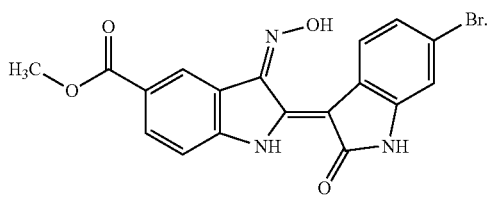

2. The method according to claim 1, wherein the cancer is prostate cancer, and the indirubin derivative is selected from the group consisting of IRD Nos. 10-11, 13, 59, 71, 79, 80, 83, 84, 87, 128, and 176.

3. The method according to claim 1, wherein the cancer is melanoma, and the indirubin derivative is selected from the group consisting of IRD Nos. 59, and 176.

4. The method according to claim 1, wherein the cancer is pancreatic cancer, and the indirubin derivative is selected from the group consisting of IRD Nos. 9, 11, 13, 59, 61, 68-71, 82-87, 115, and 176.

5. The method according to claim 1, wherein the cancer is ovarian cancer, and the indirubin derivative is selected from the group consisting of IRD Nos. 11, 13, 59, 61, 69, 71, 79-82, 84-87, 124, and 176.

6. The method according to claim 1, wherein the cancer is leukemia, and the indirubin derivative is selected from the group consisting of IRD Nos. 10-13, 59, 61, 70, 71, 79-80, 83-87, 115, 128, and 176.

7. The method according to claim 1, wherein the cancer is lymphoma, and the indirubin derivative is selected from the group consisting of IRD Nos. 10-13, 59, 79-80, 83, 84, 87, 115, 128, and 176.

8. A method of treating a condition regulated by a protein kinase in a subject comprising administering an indirubin derivative (IRD) selected from the group consisting of IRD Nos. 10, 11, 13, 61, 70, 71, 79, 80, 83-87, and 176, the protein kinase being selected from the group consisting of ABL1, ABL1 (T315I mutant), Aurora A, c-Src, FGR, FLT3, HCK, LYN, JAK2, and TYK2.

9. The method according to claim 1, wherein the protein kinase is ABL1, and the indirubin derivative is selected from the group consisting of IRD Nos. 11, 13, 61, 70, 71, 79, 80, 83-87, and 176.

10. The method according to claim 1, wherein the protein kinase is ABL1 (T315I mutant), and the indirubin derivative is selected from the group consisting of IRD Nos. 61, 79, 80, 83-85, and 87.

11. The method according to claim 1, wherein the protein kinase is Aurora A, and the indirubin derivative is selected from the group consisting of IRD Nos. 61, 70, 79, 80, 83-87, and 176.

12. The method according to claim 1, wherein the protein kinase is c-Src, and the indirubin derivative is selected from the group consisting of IRD Nos. 10, 11, 13, 61, 70, 71, 79, 80, 83-87, and 176.

13. The method according to claim 1, wherein the protein kinase is FGR, FLT3, HCK, LYN, or TYK2, and the indirubin derivative is IRD No. 176.

14. The method according to claim 1, wherein the protein kinase is JAK2, and the indirubin derivative is selected from the group consisting of IRD Nos. 61, 79, 80, 83, 84, and 87.

* * * * *

UNITED STATES PATENT AND TRADEMARK OFFICE
CERTIFICATE OF CORRECTION

PATENT NO. : 11,524,937 B2
APPLICATION NO. : 16/594894
DATED : December 13, 2022
INVENTOR(S) : Sangkil Nam et al.

It is certified that error appears in the above-identified patent and that said Letters Patent is hereby corrected as shown below:

In the Specification

Column 1, Line 17, Add a Government Interest section:
--This invention was made with government support under R01 CA115674 awarded by the National Institutes of Health. The government has certain rights in the invention.--

Signed and Sealed this
Nineteenth Day of December, 2023

Katherine Kelly Vidal
*Director of the United States Patent and Trademark Office*